OTHER PUBLICATIONS

United States Patent [19]
Paoletti
[11] Patent Number: 5,225,336
[45] Date of Patent: Jul. 6, 1993
[54] RECOMBINANT POXVIRUS HOST RANGE SELECTION SYSTEM
[75] Inventor: En

Franke, C. A., Rice, C. M., Strauss, J. H., and D. E. Hruby, Mol. Cell. Biol., 5, 1918–1924 (1985).

Gangemi, J. D. and D. G. Sharp, Virology, 85, 262–270 (1978).

Gemmell, A. and F. Fenner, Virology, 11, 219–235 (1960).

Gillard, S., Spehner, D., and R. Drillien, J. Virol., 53, 316–318 (1985).

Gillard, S., Spehner, D., Drillien, R., and A. Kirn, Proc. Natl. Acad. Sci. USA, 83, 5573–5577 (1986).

Graham, F. L. and A. J. Van der Eb, Virology, 54, 536–539 (1973).

Hruby, D. E., Lynn, D. L., Condit, R., and J. R. Kates, J. Gen. Virol., 47, 485–488 (1980).

Kieny, M. P., Lathe, R., Drillien, R., Spehner, D., Skory, S., Schmitt, D., Wictor, T., Koprowski, H., and J. P. Lecocq, Nature, (London), 312, 163–166 (1984).

Lake, J. R. and P. D. Cooper, J. Gen. Virol., 48, 135–147 (1980).

Mackett, M., Smith, G. L. and B. Moss, Proc. Natl. Acad. Sci. USA, 79, 7415–7419 (1982).

Mackett, M. and J. R. Arrand, EMBO, 4, 3229–3235 (1985).

Mayr, A., Hochstein-Mintzel, V., and H. Stickl, Infection, 3, 6–14 (1975).

McClain, M. E., Aust. J. Exp. Biol. Med. Sci., 43, 31–44 (1965).

Moyer, R. W. and C. T. Rothe, Virology, 102, 119–132 (1980).

Nakano, E., Panicali, D., and E. Paoletti, Proc. Natl. Acad. Sci. USA, 79, 1593–1596 (1982).

Panicali, D., Davis, S. W., Mercer, S. R., and E. Paoletti, J. Virol., 37, 1000–1010 (1981).

Panicali, D. and E. Paoletti, Proc. Natl. Acad. Sci. USA, 79, 4927–4931 (1982).

Panicali, D., Grzelecki, A., and C. Huang, Gene, 47, 193–199 (1986).

Perkus, M. E., Panicali, D., Mercer, S., and E. Paoletti, Virol., 152, 285–297 (1986).

Perkus, M. E., Piccini, A., Lipinskas, B. R., and E. Paoletti, Science, 229, 981–984 (1985).

Piccini, A., Perkus, M. E., and E. Paoletti, In: Methods in Enzymology, vol. 153, ed. Wu, R. and L. Grossman, (Academic Press), pp. 545–563 (1987).

Rosel, J. L., Earl, P. L., Weir, J. P., and B. Moss, J. Viol., 60, 436–449 (1986).

Shapira, S. K., Chou, J., Richaud, F. V., and M. J. Casadaban, Gene, 25, 71–82 (1983).

Southern, P. H. and P. Berg, J. Mol. Appl. Genet., 1, 327–341 (1982).

Tagaya, I., Kitamura, T., and Y. Sano, Nature, (London), 192, 381–382 (1961).

Wachsman, M., Aurelian, L., Smith, C. C., Lipinskas, B. R., Perkus, M. E., and E. Paoletti, J. Inf. Dis., 155, 1188–1197 (1987).

Wilson, E. M., Hodges, W. M., and D. E. Hruby, Gene, 49, 207–213 (1986).

Yuen, L. and B. Moss, Proc. Natl. Acad. Sci. USA, 84, 6417–6421 (1987).

Kotwal, G. J. and B. Moss, Virology, 167, 524–537 (1988).

Taylor, J. Weinberg, R., Kawaoda, Y., Webster, R. G., and E. Paoletti, Vaccine, 6, 504–508 (1988).

Taylor, J. Weinberg, R., Languet, B., Desmettre, P., and E. Paoletti, Vaccine, 6, 497–503 (1988).

Pickup, D. J., Ink, B. S., Hu, W., Ray, C. A., and W. K. Joklik, Proc. Natl. Acad. Sci. USA, 83, 7698–7702 (1986).

Southern, E. M., J. Mol. Biol., 98, 503–517 (1975).

Kotwal, G. J. and B. Moss, J. Virol., 63, 600–606 (1989).

Tabor, S. and C. C. Richardson, Proc. Natl. Acad. Sci. USA, 84, 4767–4771 (1987).

Patel, D. D. and D. J. Pickup, EMBO, 6, 3787–3794 (1987).

Patel, D. D., Ray, C. A., Drucker, R. P., and D. J. Pickup, Proc. Natl. Acad. Sci. USA, 85, 9431–9435 (1988).

Bertholet, C., Drillien, R., and R. Wittek, Proc. Natl. Acad. Sci. USA, 82, 2096–2100 (1985).

Guo, P., Goebel, S., Davis, S. Perkus, M. E., Languet, B., Desmettre, P., Allen, G., and E. Paoletti, J. Virol., 63, 4189–4198 (1989).

Tamin, A., Villarreal, E. C., Weinrich, S. L., and D. E. Hruby, Virology, 165, 141–150 (1988).

Boursnell, M. E. G., Foulds, I. J., Campbell, J. I., and M. M. Binns, J. Gen. Virol., 69, 2995–3003 (1988).

Mandecki, W., Proc. Natl. Acad. Sci. USA, 83, 7177–7181 (1986).

(List continued on next page.)

OTHER PUBLICATIONS

Spehner, D., Gillard, S., Drillien, R., and A. Kirn, J. Virol., 62, 1297–1304 (1988).

Altenburger, W., Suter, C.-P., and J. Altenburger, Arch. Virol., 105, 15–27 (1989).

Hruby, D. E., Maki, R. A., Miller, D. B., and L. A. Ball, Proc. Natl. Acad. Sci. USA, 80, 3411–3415 (1983).

Robbins, A. K., Dorney, D. J., Wathen, M. W., Whealy, M. E., Gold, C., Watson, R. J., Holland, L. E., Weed, S. D., Levine, M., Giorioso, J. C., and L. W. Enquist, J. Virol., 61, 2691–2701 (1987).

Robbins, A. K., Watson, R. J., Whealy, M. E., Hays, W. W., and L. W. Enquist, J. Virol., 58, 339–347 (1986).

Wathen, M. W. and L. M. K. Wathen, J. Virol., 51, 57–62 (1984).

Mettenleiter, T. C., Lukacs, N., Thiel, H.-J., Schreurs, C., and H. J. Rziha, Virology, 152, 66–75 (1986).

Petrovskis, E. A., Timmins, J. G., Armentrout, M. A., Marchioli, C. C., Yancey, Jr., R. J., and L. E. Post, J. Virol., 59, 216–223 (1986).

Schmitt, J. F. C. and H. G. Stunnenberg, J. Virol., 62, 1889–1897 (1988).

Vos, J. C. and H. G. Stunnenberg, EMBO, 7, 3487–3492 (1988).

Bucher, D., Popple, S., Baer, M., Mikhail, A., Gong, Y.-F., Whitaker, C., Paoletti, E., and A. Judd, J. Virol., 63, 3622–3633 (1989).

Saiki, R. K., Gelfand, D. H., Stoffel, S. Scharf, S. J. Higuchi, R., Horn, G. T., Mullis, K. B., and H. A. Erlich, Science, 239, 487–491 (1988).

Kaplan, J. M., Mardon, G., Bishop, J. M., and H. E. Varmus, Mol. Cell. Biol., 8, 2435–2441 (1988).

Baroudy, B. M., Venkatesan, S., and B. Moss, Cell, 28, 315–324 (1982).

Wittek, R. and B. Moss, Cell, 21, 277–284 (1980).

Wittek, R., Muller, H. K., Menna, A., and R. Wyler, FEBS Letters, 90, 41–46 (1978).

Slabaugh, M., Roseman, N., Davis, R., and C. Mathews, J. Virol., 62, 519–527 (1988).

Mulligan, R. C. and P. Berg, Science, 209, 1422–1427 (1980).

Pratt, D. and S. Subramani, Nuc. Acids Res., 11, 8817–8823 (1983).

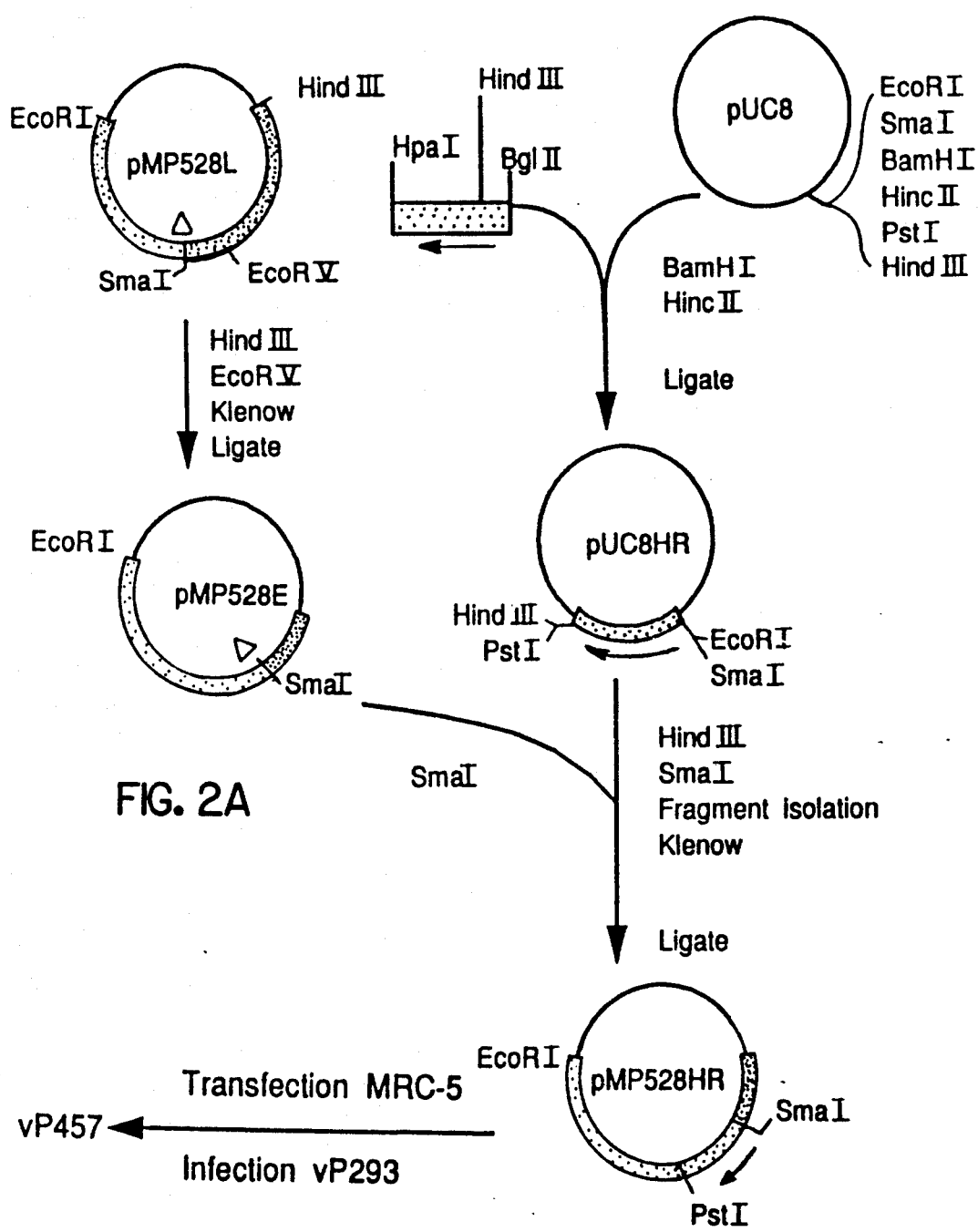
FIG. 2A
FIG. 2B
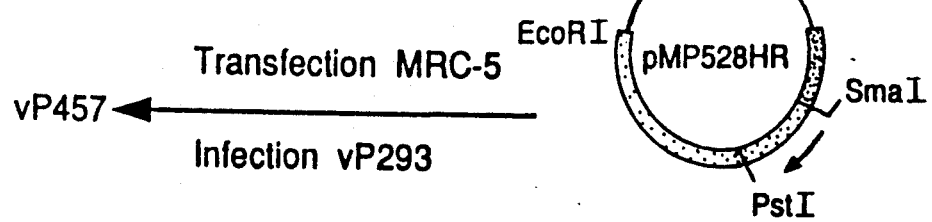
FIG. 2C
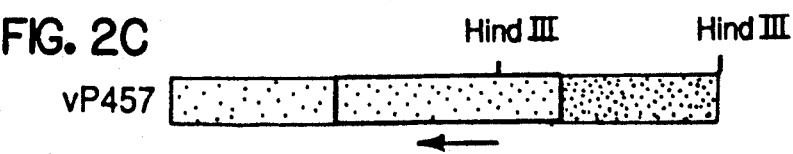

FIG. 3B TTCTTTATTCTATACTTAAAAAGTGAAAATAAATACAAAGGTTCTTGAGGGTGTGTTAAAT
TGAAAGGCGAGAAATAATCATAAATTATTCATTATCGCGATATCCGTTAAGTTGTATCGTA

FIG. 3C [CTCGAGGGGTACCCCCGGG]
　　　　　 Xhol　Kpnl　Smal

FIG. 3D [ATG-GGA-TCC-CCG-GGT-ACC-GAG-CTC-TCG-AGT-AAA-TAA-ATA-ATTTTTAT]
　　　　　 BamHI　　Kpnl　　Sacl　Xhol　STOP　　　term

FIG. 3E [ATG-GGG-ATC-CCC-GGG-TAC-CGA-GCT-CTC-GAG-TAA-ATA-AAT-AATTTTTAT]
　　　　　 BamHI　Kpnl　Smal　　Sacl　Xhol　STOP　　　term

FIG. 3F [ATG-GGG-GAT-CCC-CGG-GTA-CCG-AGC-TCT-CGA-GTA-AAT-AAA-TAATTTTTAT]
　　　　　 BamHI　Smal　Kpnl　Sacl　Xhol　STOP　　　term

FIG. 3G [CTCGAGGGATCCCGGGTACCGAGCTCTAAATAAATAATTTTTAT]
　　　　　 Xhol　BamHI　Smal　Kpnl　Sacl　STOP　　term

FIG. 4B

```
         ClaI           BamHI              KpnI
HRL15  5' CGATTACTATG-GGA-TCC-CCG-GGT-AC 3'
HRL16  3'   TAATGATAC-CCT-AGG-GGC-C     5'
                              SmaI

ClaI           BamHI              KpnI
HRL17  5' CGATTACTATG-GGG-ATC-CCC-GGG-TAC 3'
HRL18  3'   TAATGATAC-CCC-TAG-GGG-CC     5'
                              SmaI

ClaI           BamHI              KpnI
HRL19  5' CGATTACTATG-GGG-GAT-CCC-CGG-GTA-C 3'
HRL20  3'   TAATGATAC-CCC-CTA-GGG-GCC      5'
                              SmaI

ClaI    BamHI    KpnI
HRL21  5' CGATTACTGGATCCCCGGGTAC 3'
HRL22  3'   TAATGACCTAGGGGCC     5'
                     SmaI
```

FIG. 5 pHES31

```
     NcoI
AAGCTTCCATGGAAAAACGAAAGTAGTATAAAAGTAATAAACAAAAAGAATATAAAAAT
HindIII                                                  -250

TTATAGCTACTTTCTTGAGGACTGTTTCCTGAAGGAAATGAACCTCTGGAATTAGTTAGATA
                        -200

TATAGAATTAGTATACACGTTAGATTATTCTCAAACTCCTAATTATGACAGACTACGTAGACTG
        -150

TTTATACAAGATTGAAATTATATTCTTTTTTTATAGAGTGTGGTAGTGTTACGGATATCTAATA
-100                                                      -50

ClaI    -1
TTAATATTAGACTATCTCTATCGCGCTACACGACCAATATCGATTACT
``` pHES32

```
 BamHI         KpnI                    XhoI
[ATG-GGA-TCC-CCG-GGT-ACC-GAG-CTC-TCG-AGT-AAA-TAAATAATTTTTAT]
          SmaI         SacI
``` pHES33

```
 BamHI           KpnI                    XhoI
[ATG-GGG-ATC-CCC-GGG-TAC-CGA-GCT-CTC-GAG-TAAATAAATAATTTTTAT]
           SmaI         SacI
``` pHES34

```
 BamHI            KpnI                      XhoI
[ATG-GGG-GAT-CCC-CGG-GTA-CCG-AGC-TCT-CGA-GTA-AAT-AAA-TAATTTTTAT]
            SmaI          SacI
``` pHES34

```
 BamHI    KpnI         XhoI
[GGATCCCCGGGTACCGAGCTCTCGAGTAAATAAATAATTTTTAT]
       SmaI       SacI
```

FIG.6B

```
         HindIII
HRL33 5' AGCTTAGATCTACGATCTTATAATTACACGATTGTAGTTAAGTTTGAATAAAATTTTTT
HRL34 3'     ATCTAGATGCTAGAATATTAATGTGCTAACATCAATTCAAACTTATTTTAAAAAA
                               BamHI
                         ATAATAAATG-G         3'  HRL33
                         TATTATTTAC-CCT-AG    5'  HRL34

HindIII
HRL35 5' AGCTTAGATCTACGATCTTATAATTACACGATTGTAGTTAAGTTTGAATAAAATTTTTT
HRL36 3'     ATCTAGATGCTAGAATATTAATGTGCTAACATCAATTCAAAACTTATTTAAAAAA
                               BamHI
                         ATAATAAATG-GG        3'  HRL35
                         TATTATTTAC-CCC-TAG   5'  HRL36

HindIII
HRL37 5' AGCTTAGATCTACGATCTTATAATTACACGATTGTAGTTAAGTTTGAATAAAATTTTTT
HRL38 3'     ATCTAGATGCTAGAATATTAATGTGCTAACATCAATTCAAAACTTATTTAAAAAA
                               BamHI
                         ATAATAAATG-GGG       3'  HRL37
                         TATTATTTAC-CCC-CTA-G 5'  HRL38

HindIII
HRL39 5' AGCTTAGATCTACGATCTTATAATTACACGATTGTAGTTAAGTTTGAATAAAATTTTTT
HRL40 3'     ATCTAGATGCTAGAATATTAATGTGCTAACATCAATTCAAAACTTATTTAAAAAA
                               BamHI
                         ATAATAAG             3'  HRL39
                         TATTATTCCTAG         5'  HRL40
```

FIG. 7

```
              HindIII                        -50                                                        -1
pHES61   AAGCTTAGATCTACGATCTTATAATTACACGATTGTAGTTAAGTTTGAATAAATTTTTATAATAA
              BamHI      KpnI           XhoI
         [ATG-GGA-TCC-CCG-GGT-ACC-GAG-CTC-TCG-AGT-AAA-TAAATAATTTTTAT]
                   SmaI            SacI BamHI      KpnI           XhoI
pHES62   [ATG-GGG-ATC-CCC-GGG-TAC-CGA-GCT-CTC-GAG-TAAATAAATAATTTTTAT]
                   SmaI            SacI BamHI      KpnI           XhoI
pHES63   [ATG-GGG-GAT-CCC-CGG-GTA-CCG-AGC-TCT-CGA-GTA-AAT-AAA-TAATTTTTAT]
                   SmaI            SacI BamHI   KpnI    XhoI
pHES64   [GGATCCCCGGGTACCGAGCTCTCGAGTAAATAAATAATTTTTAT]
                   SmaI    SacI
```

VTK⁻79 vP293

```
Sal1
  ∧
1 TCGACTGACGACAATAACAAAATCACAACATCGTTTTTGATATTATTATTTTTCTTGGTA
  <X  V  S  S  L  L  L  I  V  V  D  N  K  I  N  N  N  K  K  T

ACGTATGCCTTTAATGGAGTTTCACCATCATACTCATATAATGGATTTGCACCACTTTCT
   V  Y  A  K  L  P  T  E  G  D  Y  E  Y  L  P  N  A  G  S  E   26

121 ATCAATGATTGTGCACTGCTGGCATCGATGTTAAATGTTTTACAACTATCATAGAGTATC
   <I  L  S  Q  A  S  S  A  D  I  N  F  T  K  C  S  D  Y  L  I

TTATCGTTAACCATGATTGGTTGTTGATGCTATCGCATTTTTTGGTTTCTTTCATTTCAG
    K  D  N  V  M    <C9L 74.7kDa (fragment)

241 TTATGTATGGATTTAGCACGTTTGGGAAGCATGAGCTCATATGATTTCAGTACTGTAGTG
   <N  H  I  S  K  A  R  K  P  L  M  L  E  Y  S  K  L  V  T  T

TCAGTACTATTAGTTTCGATCAGATCAATGTCTAGATCTATAGAATCAAAACACGATAGG
    D  T  S  N  T  E  I  L  D  I  D  L  D  I  S  D  F  C  S  L   145

361 TCAGAAGATAATGAATATCTGTACGCTTCTTTTTGTACTGTAACTTCTCGTTTTGTTAGA
   <D  S  S  L  S  Y  R  Y  A  E  K  Q  V  T  V  E  R  K  T  L

TGTTTGCATCGTGCTTTAACATCAATGGTACAAATTTTATCCTCGCTTTGTGTATCATAT
    H  K  C  R  A  K  V  D  I  T  C  I  K  D  E  S  Q  T  D  Y   105

481 TCGTCCCTACTATAAAATTGTATATTCAGATTATCATGAGATGTGTATACGCTAACGGTA
   <E  D  R  S  Y  F  Q  I  N  L  N  D  H  S  T  Y  V  S  V  T

TCAATAAACGGAGCACACCATTTAGTCATAACCGTAATCCAAAAATTTTTAAAGTATATC
    D  I  F  P  A  C  W  K  T  M  V  T  I  W  F  N  K  F  Y  I   65

601 TTAACGAAAGAAGTTGTATCATCGTTAGGATTTGGTAAATCATTATCTACAGTGTATGGT
   <K  V  F  S  T  T  D  D  N  P  N  P  L  D  N  D  V  T  Y  P

ACTAGATCCTCATAAGTGTATATATCTAGAGTAATGTTTAATTTATCAAATGGTTGATAA
    V  L  D  E  Y  T  Y  I  D  L  T  I  N  L  K  D  F  P  Q  Y   25

721 TATGGATCCTCATGACAATTTCCGAAGATGGAAATGAGATATAGACATGCAATAAATCTA
   <Y  P  D  E  H  C  N  G  F  I  S  I  L  Y  L  C  A  I  F  R

ATCGAAGACATGGTTACTCCTTAAAAAAAATACGAATAATCACCTTGGCTATTTAGTAAGT
    I  S  S  M    <C8L 21.6kDa

841 GTCATTTAACACTATACTCATATTAATCCATGGACTCATAATCTCTATACGGGATTAACG
                      <D  M  S  E  Y  D  R  Y  P  I  L  P

GATGTTCTATATACGGGGATGAGTAGTTCTCTTCTTTAACTTTATACTTTTTACTAATCA
    H  E  I  Y  P  S  S  Y  N  E  E  K  V  K  Y  K  K  S  I  M   119

961 TATTTAGACTGATGTATGGGTAATAGTGTTTGAAGAGCTCGTTCTCATCATCAGAATAAA
   <N  L  S  I  Y  P  Y  Y  H  K  F  L  E  N  E  D  D  S  Y  I

TCAATATCTCTGTTTTTTGTTATACAGATGTATTACAGCCTCATATATTACGTAATAGA
    L  I  E  T  K  K  N  Y  L  H  I  V  A  E  Y  I  V  Y  Y  F   79
```

FIG.8A

```
1081 ACGTGTCATCTACCTTATTAACTTTCACCGCATAGTTGTTTGCAAATACGGTTAATCCTT
      <T  D  D  V  K  N  V  K  V  A  Y  N  N  A  F  V  T  L  G  K

TGACCTCGTCGATTTCCGACCAATCTGGGCGTATAATGAATCTAAACTTTAATTTCTTGT
        V  E  D  I  E  S  W  D  P  R  I  I  F  R  F  K  L  K  K  Y   39

1201 AATCATTCGAAATAATTTTTAGTTTGCATCCGTAGTTATCCCCTTTATGTAACTGTAAAT
      <D  N  S  I  I  K  L  K  C  G  Y  N  D  G  K  H  L  Q  L  N

TTCTCAACGCGATATCTCCATTAATAATGATGTCGAATTCGTGCTGTATACCCATACTGA
        R  L  A  I  D  G  N  I  I  I  D  F  E  H  Q  I  G  M   <C7L  18.0kDa

1321 ATGGATGAACGAATACCGACGGCGTTAATAGTAATTTACTTTTTCATCTTTACATATTGG

GTACTAGTTTTACTATCATAAGTTTATAAATTCCACAAGCTACTATGGAATAAGCCAACC

1441 ATCTTAGTATAACACACATGTCTTAAAGTTTATTAATTAATTACATGTTGTTTTATATAT

CGCTACGAATTTAAACAGAGAAATCAGTTTAGGAAAAAAAATTATCTATCTACATCATCA
                                                    <R  D  V  D  D   147

1561 CGTCTCTGTATTCTACGATAGAGTGCTACTTTAAGATGAGACATATCCGTGTCATCAAAA
      <R  R  Q  I  R  R  Y  L  A  V  K  L  H  S  M  D  T  D  D  F

ATATACTCCATTAAAATGATTATTCCGGCAGCGAACTTGATATTGGATATATCACAACCT
        I  Y  E  M  L  I  I  I  G  A  A  F  K  I  N  S  I  D  C  G   107

1681 TTGTTAATATCTACGACAATAGACAGCAGTCCCATGGTTCCATAAACAGTGAGTTTATCT
      <K  N  I  D  V  V  I  S  L  L  G  M  T  G  Y  V  T  L  K  D

TTCTTTGAAGAGATATTTTGTAGAGATCTTATAAAACTGTCGAATGACATCGCATTTATA
        K  K  S  S  I  N  Q  L  S  R  I  F  S  D  F  S  M  A  N  I   67

1801 TCTTTAGCTAAATCGTATATGTTACCATCGTAATATCTAACCGCGTCTATCTTAAACGTT
      <D  K  A  L  D  Y  I  N  G  D  Y  Y  R  V  A  D  I  K  F  T

TCCATCGCTTTAAAGACGTTTCCGATAGATGGTCTCATTTCATCAGTCATACTGAGCCAA
        E  M  A  K  F  V  N  G  I  S  P  R  M  E  D  T  M  S  L  W   27

1921 CAAATATAATCGTGTATAACATCTTTGATAGAATCAGACTCTAAAGAAAACGAATCGGCT
      <C  I  Y  D  H  I  V  D  K  I  S  D  S  E  L  S  F  S  D  A

TTATTATACGCATTCATGATAAACTTAATGAAAAATGTTTTTCGTTGTTTAAGTTGGATG
        K  N  Y  A  N  M     <C6L  17.4kDa

2041 AATAGTATGTCTTAATAATTGTTATTATTTCATTAATTAATATTTAGTAACGAGTACACT

CTATAAAAACGAGAATGACATAACTAGTTATCAAAGTGTCTAGGACGCGTAATTTTCATA
                                   <N  D  F  H  R  P  R  T  I  K  M   194
```

FIG.8B

```
2161 TGGTATAGATCCTGTAAGCATTGTCTGTATTCTGGAGCTATTTTCTCTATCGCATTAGTG
     <H  Y  L  D  Q  L  C  Q  R  Y  E  P  A  I  K  E  I  A  N  T

AGTTCAGAATATGTTATAAATTTAAATCGAATAACGAACATAACTTTAGTAAAGTCGTCT
      L  E  S  Y  T  I  F  K  F  R  I  V  F  M  V  K  T  F  D  D  154

2281 ATATTAACTCTTTTATTTTCTAGCCATCGTAATACCATGTTTAAGATAGTATATTCTCTA
     <I  N  V  R  K  N  E  L  W  R  L  V  M  N  L  I  T  Y  E  R

GTTACTACGATCTCATCGTTGTCTAGAATATCACATACTGAATCTACATCCAATTTTAGA
      T  V  V  I  E  D  N  D  L  I  D  C  V  S  D  V  D  L  K  L  114

2401 AATTGGTCTGTGTTACATATCTCTTCTATATTATTGTTGATGTATTGTCGTAGAAAACTA
     <F  Q  D  T  N  C  I  E  E  I  N  N  N  I  Y  Q  R  L  F  S

TTACGTAGACCATTTTCTTTATAAAACGAATATATAGTACTCCAATTATCTTTACCGATA
      N  R  L  G  N  E  K  Y  F  S  Y  I  T  S  W  N  D  K  G  I   74

2521 TATTTGCACACATAATCCATTCTCTCAATCACTACATCTTTAAGATTTTCGTTGTTAAGA
     <Y  K  C  V  Y  D  M  R  E  I  V  V  D  K  L  N  E  N  N  L

TATTTGGCTAAACTATATAATTCTATTAGATCATCAACAGAATCAGTATATATTTTTCTA
      Y  K  A  L  S  Y  L  E  I  L  D  D  V  S  D  T  Y  I  K  R   34

2641 GATCCAAAGACGAACTCTTTGGCGTCCTCTATAATATTCCCAGAAAAGATATTTTCGTGT
     <S  G  F  V  F  E  K  A  D  E  I  I  N  G  S  F  I  N  E  H

TTTAGTTTATCGAGATCTGATCTGTTCATATACGCCATGATTGTACGGTACGTTATGATA
      K  L  K  D  L  D  S  R  N  M  Y  A  M     <C5L 24.5kDa

2761 ACCGCATAAAATAAAAATCCATTTTCATTTTTAACCAATACTATTCATAATTGAGATTGA
     :                                              <E  Y  N  L  N  I

TGTAATACTTTGTTACTTTGAACGTAAAGACAGTACACGGATCCGTATCTCCAACAAGCA
      Y  Y  K  T  V  K  F  T  F  V  T  C  P  D  T  D  G  V  L  V  291

2881 CGTAGTAATCAAATTTGGTGTTGTTAAACTTCGCAATATTCATCAATTTAGATAGAAACT
     <Y  Y  D  F  K  T  N  N  F  K  A  I  N  M  L  K  S  L  F  K

TATACTCATCATCTGTTTTAGGAATCCATGTATTATTACCACTTTCCAACTTATCATTAT
      Y  E  D  D  T  K  P  I  W  T  N  N  G  S  E  L  K  D  N  D  251

3001 CCCAGGCTATGTTTCGTCCATCATCGTTGCGCAGAGTGAATAATTCTTTTGTATTCGGTA
     <W  A  I  N  R  G  D  D  N  R  L  T  F  L  E  K  T  N  P  L

GTTCAAATATATGATCCATGCATAGATCGGCAAAGCTATTGTAGATGTGATTTTTCCTAA
      E  F  I  H  D  M  C  L  D  A  F  S  N  Y  I  H  N  K  R  F  211

3121 ATCTAATATAAAACTCGTTTACTAGCAAACACTTTCCTGATTTATCGACCAAGACACATA
     <R  I  Y  F  E  N  V  L  L  C  K  G  S  K  D  V  L  V  C  I

TGGTTTCTAAATCTATCAAGTGGTGGGGATCCATAGTTATGACGCAGTAACATATATTAT
      T  E  L  D  I  L  H  H  P  D  M  T  I  V  C  Y  C  I  N  N  171
```

FIG.8C

```
3241 TACATTCTTGACTGTCGCTAATATCTAAATATTTATTGTTATCGTATTGGATTCTGCATA
     <C  E  Q  S  D  S  I  D  L  Y  K  N  N  D  Y  Q  I  R  C  I

TAGATGGCTTGTATGTCAAAGATATAGAACACATAACCAATTTATAGTCGCGCTTTACAT
      S  P  K  Y  T  L  S  I  S  C  M  V  L  K  Y  D  R  K  V  N  131

3361 TCTCGAATCTAAAGTTAAGAGATTTAGAAAACATTATATCCTCGGATGATGTTATCACTG
     <E  F  R  F  N  L  S  K  .S  F  M  I  D  E  S  S  T  I  V  T

TTTCTGGAGTAGGATATATTAAAGTCTTTACAGATTTCGTCCGATTCAAATAAATCACTA
      E  P  T  P  Y  I  L  T  K  V  S  K  T  R  N  L  Y  I  V  L  91

3481 AATAATATCCCACATTATCATCTGTTAGAGTAGTATCATTAAATCTATTATATTTTATGA
     <Y  Y  G  V  N  D  D  T  L  T  T  D  N  F  R  N  Y  K  I  F

AAGATATATCACTGCTCACCTCTATATTTCGTACATTTTTAAACTGTTTGTATAATATCT
      S  I  D  S  S  V  E  I  N  R  V  N  K  F  Q  K  Y  L  I  E  51

3601 CTCTGATACAATCAGATATATCTATTGTGTCGGTAGACGATACCGTTACATTTGAATTAA
     <R  I  C  D  S  I  D  I  T  D  T  S  S  V  T  V  N  S  N  I

TGGTGTTCCATTTTACAACTTTTAACAAGTTGACCAATTCATTTCTAATAGTATCAAACT
      T  N  W  K  V  V  K  L  L  N  V  L  E  N  R  I  T  D  F  E  11

3721 CTCCATGATTAAATATTTTAATAGTATCCATTTTATATCACTACGGACACAAAGTAGCTG
     <G  H  N  F  I  K  I  T  D  M     <C4L 37.2kDa

ACATAAACCATTGTATAATTTTTATGTTTTATGTTTATTAGCGTACACATTTTGGAAGTT
                                            <R  V  C  K  P  L  E  257

3841 CCGGCTTCCATGTATTTCCTGGAGAGCAAGTAGATGATGAGGAACCAGATAGTTTATATC
     <P  K  W  T  N  G  P  S  C  T  S  S  S  S  G  S  L  K  Y  G

CGTACTTGCACTTAAAGTCTACATTGTCGTTGTATGAGTATGATCTTTTAAACCCGCTAG
      Y  K  C  K  F  D  V  N  D  N  Y  S  Y  S  R  K  F  G  S  S  217

3961 ACAAGTATCCGTTTGATATTGTAGGATGTGGACATTTAACAATCTGACACGTGGGTGGAT
     <L  Y  G  N  S  I  T  P  H  P  C  K  V  I  Q  C  T  P  P  D

CGGACCATTCTCCTCCTGAACACAGGACACCAGAGTTACCAATCAACGAATATCCACTAT
      S  W  E  G  G  S  C  L  V  G  S  N  G  I  L  S  Y  G  S  N  177

4081 TGCAACTATAAGTTACAACGCTTCCATCGGTATAAAAATCCTCGTATCCGTTATGTCTTC
     <C  S  Y  T  V  V  S  G  D  T  Y  F  D  E  Y  G  N  H  R  G

CGTTGGATATAGATGGAGGGGATTGGCATTTAACAGATTCACAAATAGGTGCCTCGGGAT
      N  S  I  S  P  P  S  Q  C  K  V  S  E  C  I  P  A  E  P  N  137

4201 TCCATACCATAGATCCAGTAGATCCTAATTCACAATACGATTTAGATTCACCGATCAAAT
     <W  V  M  S  G  T  S  G  L  E  C  Y  S  K  S  E  G  I  L  H

GATATCCGCTATTACAAGAGTACGTTATACTAGAGCCAAAGTCTACTCCACCAATATCAA
      Y  G  S  N  C  S  Y  T  I  S  S  G  F  D  V  G  G  I  D  L  97
```

FIG.8D

```
4321 GTTGGCCATTATCGATATCTCGAGGCGATGGGCATCTCCGTTTAATACATTGATTAAAGA
     <Q  G  N  D  I  D  R  P  S  P  C  R  R  K  I  C  Q  N  F  L

GTGTCCATCCAGTACCTGTACATTTAGCATATATAGGTCCCATTTTTTGCTTTCTGTATC
      T  W  G  T  G  T  C  K  A  Y  I  P  G  M  K  Q  K  R  Y  G 57

4441 CAGGTAGACATAGATATTCTATAGTGTCTCCTATGTTGTAATTAGCATTAGCATCAGTCT
     <P  L  C  L  Y  E  I  T  D  G  I  N  Y  N  A  N  A  D  T  E

CCACACTATTCTTAAATTTCATATTAATGGGTCGTGACGGAATAGTACAGCATGATAGAA
      V  S  N  K  F  K  M  N  I  P  R  S  P  I  T  C  C  S  L  V 17

4561 CGCATCCTATTCCCAACAATGTCAGGAACGTCACGCTCTCCACCTTCATATTTATTTATC
     <C  G  I  G  L  L  T  L  F  T  V  S  E  V  K  M     <C3L 28.6kDa

CGTAAAAATGTTATCCTGGACATCGTACAAATAATAAAAAGCCCATATATGTTCGCTATT
                                                                  <Q 512

4681 GTAGAAATTGTTTTTCACAGTTGCTCAAAAACGATGGCAGTGACTTATGAGTTACGTTAC
     <L  F  Q  K  E  C  N  S  L  F  S  P  L  S  K  H  T  V  N  C

ACTTTGGAGTCTCATCTTTAGTAAACATATCATAATATTCGATATTACGAGTTGACATAT
      K  P  T  E  D  K  T  F  M  D  Y  Y  E  I  N  R  T  S  M  D 472

4801 CGAACAAATTCCAAGTATTTGATTTTGGATAATATTCGTATTTTGCATCTGCTATAATTA
     <F  L  N  W  T  N  S  K  P  Y  Y  E  Y  K  A  D  A  I  I  L

AGATATAATCACCGCAAGAACACACGAACATCTTTCCTACATGGTTAAAGTACATGTACA
      I  Y  D  G  C  S  C  V  F  M  K  G  V  H  N  F  Y  M  Y  L 432

4921 ATTCTATCCATTTGTCTTCCTTAACTATATATTTGTATAGATAATTACGAGTCTCGTGAG
     <E  I  W  K  D  E  K  V  I  Y  K  Y  L  Y  N  R  T  E  H  T

TAATTCCAGTAATTACATAGATGTCGCCGTCGTACTCTACAGCATAAACTATACTATGAT
      I  G  T  I  V  Y  I  D  G  D  Y  E  V  A  Y  V  I  S  H  H 392

5041 GTCTAGGCATGGGAGACTTTTTTATCCAACGATTTTTAGTGAAACATTCCACATCGTTTA
     <R  P  M  P  S  K  K  I  W  R  N  K  T  F  C  E  V  D  N  L

ATACTACATATTTTTCATACGTGGTATAAACTCCACCCATTACATATATATCATCGTTTA
      V  V  Y  K  E  Y  T  T  T  Y  V  G  G  M  V  Y  I  D  D  N  V 352

5161 CGAATACCGACGCGCCTGAATATCTAGGAGTAATTAAGTTTGGAAGTCTTATCCATTTCG
     <F  V  S  A  G  S  Y  R  P  T  I  L  N  P  L  R  I  W  K  S

AAGTGCCGTGTTTCAAATATTCTGCCACACCCGTTGAAATAGAAAATTCTAATCCTCCTA
      T  G  H  K  L  Y  E  A  V  G  T  S  I  S  F  E  L  G  G  I 312

5281 TTACATATAACTTTCCATCGTTAACACAAGTACTAACTTCTGATTTTAACGACGACATAT
     <V  Y  L  K  G  D  N  V  C  T  S  V  E  S  K  L  S  S  M  N

TAGTAACCGTTTTCCATTTTTTCGTTTCAAGATCTACCCGCGATACGGAATAAACATGTC
      T  V  T  K  W  K  K  T  E  L  D  V  R  S  V  S  Y  V  H  R 272
```

FIG.8E

```
5401 TATTGTTAATCATGCCGCCAATAATGTATAGACAATTATGTAAAACATTTGCATTATAGA
      <N  N  I  M  G  G  I  I  Y  L  C  N  H  L  V  N  A  N  Y  F

ATTGTCTATCTGTATTACCGACTATCGTCCAATATTCTGTCCTAGGAGAGTAATGGGTTA
       Q  R  D  T  N  G  V  I  T  W  Y  E  T  R  P  S  Y  H  T  I   232

5521 TTGTGGATATATAATCAGAGTTTTTAATGACTACTATATTATGTTTTATACCATTTCGTG
      <T  S  I  Y  D  S  N  K  I  V  V  I  N  H  K  I  G  N  R  T

TCACTGGCTTTGTAGATTTGGATATAGTTAATCCCAACAATGATATAGCATTGCGCATAG
        V  P  K  T  S  K  S  I  T  L  G  L  L  S  I  A  N  R  M  T  192

5641 TATTAGTCATAAACTTGGGATGTAAAATGTTGATGATATCTACATCGTTTGGATTTTTAT
      <N  T  M  F  K  P  H  L  I  N  I  I  D  V  D  N  P  N  K  H

GTATCCACTTTAATAATATCATAGCTGTAACATCCTCATGATTTACGTTAACGTCTTCGT
        I  W  K  L  L  I  M  A  T  V  D  E  H  N  V  N  V  D  E  H  152

5761 GGGATAAGATAGTTGTCAGTTCATCCTTTGATAATTTTCCAAATTCTGGATCGGATGTCA
      <S  L  I  T  T  L  E  D  K  S  L  K  G  F  E  P  D  S  T  V

CCGCAGTAATATTGTTGATTATTTCTGACATCGACGCATTATATAGTTTTTTAATTCCAT
        A  T  I  N  N  I  I  E  S  M  S  A  N  Y  L  K  K  I  G  Y  112

5881 ATCTTTTAGAAAAGTTAAACATCCTTATACAATTTGTGGAATTAATATTATGAATCATAG
      <R  K  S  F  N  F  M  R  I  C  N  T  S  N  I  N  H  I  M  T

TTTTTACACATAGATCTACTACAGGCGGAACATCAATTATTACGGCAGCAACTAGTATCA
        K  V  C  L  D  V  V  P  P  V  D  I  I  V  A  A  V  L  I  M  72

6001 TTTCTACATTGTTTATGGTGATGTTTATCTTCTTCCAGCGCATATAGTCTAATAGCGATT
      <E  V  N  N  I  T  I  N  I  K  K  W  R  M  Y  D  L  L  S  E

CAAACGCGTGATAGTTTATACCATTCAATATAATCGCTTCATCCTTTAGATGGTGATCCT
        F  A  H  Y  N  I  G  N  L  I  I  A  E  D  K  L  H  H  D  Q  32

6121 GAATGCGTTTAAAAAAATTATACGGAGACGCCGTAATAATTTCCTTATTCACTTGTATAA
      <I  R  K  F  F  N  Y  P  S  A  T  I  I  E  K  N  V  Q  I  I

TTTCCCCATTGATAGAAAATATCACGCTTTCCATTCTTGAAGTACTATAAGTAATTATAG
        E  G  N  I  S  F  I  V  S  E  M     <C2L 59.kDa

6241 TATAATGTAAAGGTTTATATATTCAATATTTTTTATAAAAAAATCATTTCGACATTAATT
                                                       <K  S  M  L  E

CCTTTTTAAATTTGCGTCTATCATCTATAGAAACATATTCTATGAATTTATAAAATGCTT
        K  K  F  K  R  R  D  D  I  S  V  Y  E  I  F  K  Y  F  A  K  200

6361 TTACGTGTCCTATCGTAGGCGATAGAACCGCTAAAAAGCCTATCGAATTTCTACAAAAGA
      <V  H  G  I  T  P  S  L  V  A  L  F  G  I  S  N  R  C  F  F

ATCTGTTATATGGTATAGGGAGAGTATAAAACATTAAATGTCCGTACTTATTAAAGTATT
        R  N  Y  P  I  P  L  T  Y  F  M  L  H  G  Y  K  N  F  Y  E  160
```

FIG.8F

```
6481 CAGTAGCCAATCCTAACTCTTTCGAATACTTATTAATGGCTCTTGTTCTGTACGAATCTA
      <T  A  L  G  L  E  K  S  Y  K  N  I  A  R  T  R  Y  S  D  I

TTTTTTTGAACAACGGACCTAGTGGTATATCTTGTTCTATGTATCTAAAATAATGTCTGA
       K  K  F  L  P  G  L  P  I  D  Q  E  I  Y  R  F  Y  H  R  V  120

6601 CTAGATCCGTTAGTTTAATATCCTCAGTCATCTTGTCTAGAATGGCAAATCTAACTGCGG
      <L  D  T  L  K  I  D  E  T  M  K  D  L  I  A  F  R  V  A  P

GTTTAGGCTTTAGTTTAGTTTCTATATCTACATCTATGTCTTTATCTAACACCAAAAATA
       K  P  K  L  K  T  E  I  D  V  D  I  D  K  D  L  V  L  F  I  80

6721 TAATAGCTAATATTTTATTACAATCATCCGGATATTCTTCTACGATCTCACTAACTAATG
      <I  A  L  I  K  N  C  D  D  P  Y  E  E  V  I  E  S  V  L  T

TTTCTTGGTTATACTAGTATAGTCACTATCGGACAAATAAAGAAAATCAGATGATCGAT
       E  K  T  I  S  T  Y  D  S  D  S  L  Y  L  F  D  S  S  R  H  40

6841 GAATAATACATTTAAATTCATCATCTGTAAGATTTTTGAGATGTCTCATTAGAATATTAT
      <I  I  C  K  F  E  D  D  T  L  N  K  L  H  R  M  L  I  N  N

TAGGGTTAGTACTCATTATCATTCGGCAGCTATTACTTATTTTATTATTTTTCACCATAT
       P  N  T  S  M  I  M  R  C  S  N  S  I  K  N  N  K  V  M  C1L 26.4kDa
                                                      <K  E  G  Y  114

6961 AGATCAATCATTAGATCATCAAAATATGTTTCAATCATCCTAAAGAGTATGGTGAATGAC
      <L  D  I  M  L  D  D  F  Y  T  E  I  M  R  F  L  I  T  F  S

TCTTCCCATCTAATTTCTGAACGTTCACCAATGTCTCTAGCCACTTTGGCACTAATAGCG
       E  E  W  R  I  E  S  R  E  G  I  D  R  A  V  K  A  S  I  A  74

7081 ATCATTCGCTTAGCGTCTTCTATATTATTAACTGGTTGATTCAATCTATCTAGCAATGGA
      <I  M  R  K  A  D  E  I  N  N  V  P  Q  N  L  R  D  L  L  P

CCGTCGGACAGCGTCATTCTCATGTTCTTAATCAATGTACATACATCGCCGTCATCTACC
       G  D  S  L  T  M  R  M  N  K  I  L  T  C  V  D  G  D  D  V  34

7201 AATTCATCCAACAACATAAGCTTTTTAAAATCATCATTATAATAGGTTTGATCGTTGTCA
      <L  E  D  L  L  M  L  K  K  F  D  D  N  Y  Y  T  Q  D  N  D

TTTCTCCAAAGAATATATCTAATAAGTAGAGTCCTCATGATTAGTTAACAACTATTTTTT
       N  R  W  L  I  Y  R  I  L  L  T  R  M    <N1L 14.0kDa

7321 ATGTTAAATCAATTAGTACACCGCTATGTTTAATACTTATTCATATTTTAGTTTTTAGGA

TTGAGAATCAATACAAAAATTAATGCATCATTAATTTTAGAAATACTTAGTTTCCACGTA
                                             <F  Y  K  T  E  V  Y  169

7441 GTTAATGAAACATTTGAACTCATCGTACAGGACGTTCTCGTACAGGACGTAACTATAAAC
      <N  I  F  C  K  F  E  D  Y  L  V  N  E  Y  L  V  Y  S  Y  V

CGGTTTATATTTGTTCAAGATAGATACAAATCCGATAACTTTTTTTACGAATTCTACGGG
       P  K  Y  K  N  L  I  S  V  F  G  I  V  K  K  V  F  E  V  P  129
```

FIG.8G

```
7561 ATCCACTTTAAAAGTGTCATACGGGGTTCTTTTTATTTTTTTAAACAGATCAATGGTGTG
     <D  V  K  F  T  D  Y  P  T  R  K  I  K  K  F  L  D  I  T  H

ATGTTGATTAGGTCTTTTACGAATTTGATATAGAATAGCGTTTACATATTCTCCATAATG
      H  Q  N  P  R  K  R  I  Q  Y  L  I  A  N  V  Y  E  G  Y  H   89

7681 GTCAATCGCCATTTGTTCGTATGTCATAAATTCTTTAATTATATGACACTGTGTATTGTT
     <D  I  A  M  Q  E  Y  T  M  F  E  K  I  I  H  C  Q  T  N  N

TAGTTCATCCTTGTTCATTGTTAGGAATCTATTCAAAATGGCAATTATACTAGAACTATA
      L  E  D  K  N  M  T  L  F  R  N  L  I  A  I  I  S  S  S  Y   49

7801 GGTGCGTTGTATACACATATTGATGTGTCTGTTTATACAATCCATGATATTTGGATCCAT
     <T  R  Q  I  C  M  N  I  H  R  N  I  C  D  M  I  N  P  D  M

GCTACTACCTTCGGGTAAAATTGTAGCATCATATACCATTTCTAGTACTTTAGGTTCATT
      S  S  G  E  P  L  I  T  A  D  Y  V  M  E  L  V  K  P  E  N   9

7921 GTTATCCATTGCAGAGGACGTCATGATCGAATCATAAAAAAATATATTATTTTTATGTTA
     <N  D  M  A  S  S  T  M     <N2L 20.8kDa

TTTTGTTAAAAATAATCATCGAATACTTCGTAAGATACTCCTTCATGAACATAATCAGTT
                    <F  Y  D  D  F  V  E  Y  S  V  G  E  H  V  Y  D  T   456

8041 ACAAAACGTTTATATGAAGTAAAGTATCTACGATTTTTACAAAAGTCCGGATGCATAAGT
     <V  F  R  K  Y  S  T  F  Y  R  R  N  K  C  F  D  P  H  M  L

ACAAAGTACGCGATAAACGGAATAATAATAGATTTATCTAGTTTATCTTTTTCTATAGCT
      V  F  Y  A  I  F  P  I  I  I  S  K  D  L  K  D  K  E  I  A   416

8161 TTCATAGTTAGATACATGGTCTCAGAAGTAGGATTATGTAACATCAGCTTCGATAAAATG
     <K  M  T  L  Y  M  T  E  S  T  P  N  H  L  M  L  K  S  L  I

ACTGGGTTATTTAGTCTTACACATTCGCTCATACATGTATGACCGTTAACTACAGAGTCT
      V  P  N  N  L  R  V  C  E  S  M  C  T  H  G  N  V  V  S  D   376

8281 ACACTAAAATGATTGAACAATAGATAGTCTACCATTGTTTCGTATTCAGATAGTACAGCG
     <V  S  F  H  N  F  L  L  Y  D  V  M  T  E  Y  E  S  L  V  A

TAGTACATAGCATCTTCACAAATTATATCATTGTCTAATAGATATTTGACGCATCTTATG
      Y  Y  M  A  D  E  C  I  I  D  N  D  L  L  Y  K  V  C  R  I   336

8401 GATCCCACTTCAACAGCCATCTTAAAATCGGTAGAATCATATTGCTTTCCTTTATCATTA
     <S  G  V  E  V  A  M  K  F  D  T  S  D  Y  Q  K  G  K  D  N

ATAATTTCTAGAACATCATCTCTATCATAAAAGATACAAATATTAACTGTTTGATCCGTA
      I  I  E  L  V  D  D  R  D  Y  F  I  C  I  N  V  T  Q  D  T   296

8521 ATAACATTGCTAGTCGATAGCAATTTGTTAATAAGATGCGCTGGGCTCAATGTCTTAATA
     <I  V  N  S  T  S  L  L  K  N  I  L  H  A  P  S  L  T  K  I

AGAAGTGTAAGAGGACTATCTCCGAATTTGTTTTGTTTATTAACATCCGTTGATGGAAGT
      L  L  T  L  P  S  D  G  F  K  N  Q  K  N  V  D  T  S  P  L   256
```

FIG.8H

```
8641 AAAAGATCTATAATGTCTACATTCTTGACTGTTTTAGAGCATACAATATGGAGAGGTGTA
     <L  L  D  I  I  D  V  N  K  V  T  K  S  C  V  I  H  L  P  T

TTTCCATCATGATCTGGTTTTGAGGGACTAATTCCTAGTTTCATCATCCATGAGATTGTA
      N  G  D  H  D  P  K  S  P  S  I  G  L  K  M  M  W  S  I  T   216

8761 GAAGCTTTTGGATTGTCTGACATAAGATGTCTATGAATATGATTTTTGCCAAATTTATCC
     <S  A  K  P  N  D  S  M  L  H  R  H  I  H  N  K  G  F  K  D

ACTATCCTGGCTTCGAATCCGATGGACATTATTTTTTAAACACTCTTTCTGAAGGATCT
      V  I  R  A  E  F  G  I  S  M  I  K  K  F  V  R  E  S  P  D   176

8881 GTACACGCCAACAACGGACCACATCCTTCTTCATCAACCGAGTTGTTAATCTTGGCTCCA
     <T  C  A  L  L  P  G  C  G  E  E  D  V  S  N  N  I  K  A  G

TACTGTACCAATAAATTTATTCTCTCTATGACTTCATCATCTGTTCCCGAGAGATAATAT
      Y  Q  V  L  L  N  I  R  E  I  V  E  D  D  T  G  S  L  Y  Y   136

9001 AGAGGTGTTTTATTATGTTTATCACACGCGTTTGGATCTGCGCCGTGCGTCAGCAGCATC
     <L  P  T  K  N  H  K  D  C  A  N  P  D  A  G  H  T  L  L  M

GCGACTATTCTATTATTATTAATTTTAGAAGCTATATGCAATGGATAATTTCCATCATCA
      A  V  I  R  N  N  N  I  K  S  A  I  H  L  P  Y  N  G  D  D    96

9121 TCCGTCTCATTTGGAGAGTATCCTCTATGAAGAAGTTCTTCGACAAATCGTTCATCTAGT
     <D  T  E  N  P  S  Y  G  R  H  L  L  E  E  V  F  R  E  D  L

CCTTTAATTCCACAATACGCATGTAGAATGTGATAATTATTTCCAGAAGGTTCGATAGCT
      G  K  I  G  C  Y  A  H  L  I  H  Y  N  N  G  S  P  E  I  A    56

9241 TGTAGCATATTCCTAAATACATCTAAATTTTTACTATTATATTTGGCATAAAGAGATAGA
     <Q  L  M  N  R  F  V  D  L  N  K  S  N  Y  K  A  Y  L  S  L

TAATACTCGGCCGACATAATGTTGTCCATTGTAGTATAAAAATTAATATTTCTATTTCTA
      Y  Y  E  A  S  M  I  N  D  M  T  T  Y  F  N  I  N  R  N  R    16

9361 TTTCTGTATATTTGCAACAATTTACTCTCTATAACAAATATCATAACTTAGTTCTTTTAT
     <N  R  Y  I  Q  L  L  K  S  E  I  V  F  I  M      <M1L 54.2kDa
                                         <E  R  Y  C  I  D  Y  S  L  E  K  I

GTCAAGAAGGCACTGGTTTAGTTCATCTATAAATGTCACGCCATAACTACCACGCATGCC
          D  L  L  C  Q  N  L  E  D  I  F  T  V  G  Y  S  G  R  M  G   189

9481 ATACTCAGAATTATGATAAAGATATTTATCCTTGGGGTGTAGGTAATGGGGATTAATCTT
     <Y  E  S  N  H  Y  L  Y  K  D  K  P  H  L  Y  H  P  N  I  K

TGTTGGATCAGTCTCTAAGTTAACACATGTCACACATGATCCATTTATAGTTATATCACA
      T  P  D  T  E  L  N  V  C  T  V  C  S  G  N  I  T  I  D  C   149

9601 CGATGATGATTTATGAATTGATTCCGGAAGATCGCTATCGTATTTTGTGGTTCCACAATT
     <S  S  S  K  H  I  S  E  P  L  D  S  D  Y  K  T  T  G  C  N

CATTTCCATACATGTTATTGTCACACTAATATTATGATGAACTTTATCTAGCCGCTGAGT
      M  E  M  C  T  I  T  V  S  I  N  H  H  V  K  D  L  R  Q  T   109
```

FIG.8 I

```
9721 GGTAAACAACAGAACAGATAGTTTATTATCTTTACCAACACCCTCAGCCGCTGCCACAAA
     <T  F  L  L  V  S  L  K  N  D  K  G  V  G  E  A  A  A  V  F

TCTCTGATCCGTATCCATGATGGTCATGTTTATTTCTAGTCCGTATCCAGTCAACACTAT
      R  Q  D  T  D  M  I  T  M  N  I  E  L  G  Y  G  T  L  V  I  69

9841 GTTAGCATTTCTGTCGATATAGCTTTCACTCATATGACACTCACCAATAATAGTAGAATT
     <N  A  N  R  D  I  Y  S  ·E  S  M  H  C  E  G  I  I  T  S  N

AATGTCGTAATTTACACCAATAGTGAGTTCGGCGGCAAAGTACCAATACCGGTAATCTTG
      I  D  Y  N  V  G  I  T  L  E  A  A  F  Y  W  Y  R  Y  D  Q  29

9961 TCGAGGAGGACATATAGTATTCTTGTATTCTACCGAATACCCGAGAGATGCGATACAAAA
     <R  P  P  C  I  T  N  K  Y  E  V  S  Y  G  L  S  A  I  C  F

GAGCAAGACTAATTTGTAAACCATCTTACTCAAAATATGTAACAATAGTACGATGCAATG
      L  L  V  L  K  Y  V  M  <M2L 25.1kDa

10081 AGTAAGACAATAGGAAATCTATCTTATATACACATAATTATTCTATCAATTTTACCAATT

AGTTAGTGTAATGTTAACAAAAATGTGGGAGAATCTAATTAGTTTTTCTTTACACAATTG
                                                        <N  K  K  V  C  N  278

10201 ACGTACATGAGTCTGAGTTCCTTGTTTTTGCTAATTATTTCATCCAATTTATTATTCTTG
      <V  Y  M  L  R  L  E  K  N  K  S  I  I  E  D  L  K  N  N  K

ACGATATCGAGATCTTTTGTATAGGAGTCAGACTTGTATTCAACATGCTTTTCTATAATC
       V  I  D  L  D  K  T  Y  S  D  S  K  Y  E  V  H  K  E  I  I  238

10321 ATCTTAGTTATTTCGGCATCATCCAATAGTACATTTTCCAGATTAACAGAGTAGATATTA
      <M  K  T  I  E  A  D  D  L  L  V  N  E  L  N  V  S  Y  I  N

ATGTCGTATTTGAACAGAGCCTGTAACATCTCAATGTCTTTATTATCTATAGCCAATTTA
       I  D  Y  K  F  L  A  Q  L  M  E  I  D  K  N  K  I  A  L  K  198

10441 ATGTCCGGAATGAAGAGAAGGGAATTATTGGTGTTTGTCGACGTCATATAGTCGAGCAAG
      <I  D  P  I  F  L  L  S  N  N  T  N  T  S  T  M  Y  D  L  L

AGAATCATCATATCCACGTGTCCATTTTTTATAGTGGTGTGAATACAACTAAGGAGAATA
       L  I  M  M  D  V  H  G  N  K  I  T  T  H  I  C  S  L  L  I  158

10561 GCCAGATCAAAAGTAGATGGTATTTCTGAAAGAAAGTATGATACAATACTTACATCATTA
      <A  L  D  F  T  S  P  I  E  S  L  F  Y  S  V  I  S  V  D  N

AGCATGACGGCATGATAAAATGAAGTTTTCCATCCAGTTTTCCCATAGAACATCAGTCTC
       L  M  V  A  H  Y  F  S  T  K  W  G  T  K  G  Y  F  M  L  R  118

10681 CAATTTTTCTTAAACAGTTTCACCGTTTGCATGTTACCACTATCAACCGCATAATACAAT
      <W  N  K  K  F  L  K  V  T  Q  M  N  G  S  D  V  A  Y  Y  L

GCGGTGTTTCCTTTGTCATCAAATTGTGAATCATCCATTCCACTGAATAGCAAAATCTTT
       A  T  N  G  K  D  D  F  Q  S  D  D  M  G  S  F  L  L  I  K  78
```

FIG.8J

```
10801 ACTATTTTGGTATCTTCTAATGTGGCTGCCTGATGTAATGGAAATTCATTCTCTAGAAGA
      <V  I  K  T  D  E  L  T  A  A  Q  H  L  P  F  E  N  E  L  L

TTTTTCAATGCTCCAGCGTTCAACAACGTACATACTAGACGCACGTTATTATCAGCTATT
       N  K  L  A  G  A  N  L  L  T  C  V  L  R  V  N  N  D  A  I  38

10921 GCATAATACAAGGCACTATGTCCATGGACATCCGCCTTAAATGTATCTTTACTAGAGAGA
      <A  Y  Y  L  A  S  H  G  H  V  D  A  K  F  T  D  K  S  S  L

AAGCTTTTCAGCTGCTTAGACTTCCAAGTATTAATTCGTGACAGATCCATGTCTGAAACG
       F  S  K  L  Q  K  S  K  W  T  N  I  R  S  L  D  M  <K1L 32.5kDa

11041 AGACGCTAATTAGTGTATATTTTTTCATTTTTTATAATTTTGTCATATTGCACCAGAATT

AATAATATCTCTAATAGATCTGATTAGTAGATACATGGCTATCGCAAAACAACATATACA

11161 CATTTAATAAAAATAATATTTATTAAGAAAATTCAGATTTCACGTACCCATCAATATAAA

TAAAATAATGATTCCTTCCACCGTATCCATAAACAATATTAAGGAGATTCTACCTTACCC
                                                    <P  S  E  V  K  G  364
11281 ATAAACAATATAAATCCAGTAATATCATGTCTAATGATGAACACAAATGGTGTATTAAAT
      <M  F  L  I  F  G  T  I  D  H  R  I  I  F  V  F  P  T  N  F

TCCAGTTTTTCAGGAGATGATCTCGCCGTAGCTACCATGATAGTAGATGCCTCTGCTACA
       E  L  K  E  P  S  S  R  A  T  A  V  M  I  T  S  A  E  A  V  324

11401 GTTCCTTGTTCGTCGACATCTATCTTTGCATTCTGAAACATTTTATAAATATATAATGGG
      <T  G  Q  E  D  V  D  I  K  A  N  Q  F  M  K  Y  I  Y  L  P

TCCCTAGTCATATGTTTAAACGACGCATTATCTGGATTAAACATACTAGGAGCCATCATT
       D  R  T  M  H  K  F  S  A  N  D  P  N  F  M  S  P  A  M  M  284

11521 TCGGCTATCGACTTAATATCCCTCTTATTTTCGATAGAAAATTTAGGGAGTTTAAGATTG
      <E  A  I  S  K  I  D  R  K  N  E  I  S  F  K  P  L  K  L  N

TACACTTTATTCCCTAATTGAAACGACCAATAGTCTAATTTTGCAGCCGTAATAGAATCT
       Y  V  K  N  G  L  Q  F  S  W  Y  D  L  K  A  A  T  I  S  D  244

11641 GTGAAATGGGTCATATTATCACCTATTGCCAGGTACATACTAATATTAGCATCCTTATAC
      <T  F  H  T  M  N  D  G  I  A  L  Y  M  S  I  N  A  D  K  Y

GGAAGGCGCACCATATCATATTCTTCGTCATCGATTGTGATTGTATTTCCTTGCAATTTA
       P  L  R  V  M  D  Y  E  E  D  D  I  T  I  T  N  G  Q  L  K  204

11761 GTAACTACGTTCATCATGGGAACCGTTTTCGTACCGTACTTATTAGTAAAACTAGCATTG
      <T  V  V  N  M  M  P  V  T  K  T  G  Y  K  N  T  F  S  A  N

CGTGTTTTAGTGATATCAAACGGATATTGCCATGTACCTTTAAAATATATAGTATTAATG
       R  T  K  T  I  D  F  P  Y  Q  W  T  G  K  F  Y  I  T  N  I  164
```

FIG.8K

```
11881 ATTGCCCATAGAGTATTATTGTCGAGCATATTAGAATCTACTACATTAGACATACCGGAT
      <I  A  W  L  T  N  N  D  L  M  N  S  D  V  V  N  S  M  G  S

CTACGTTCTACTATAGAATTAATTTTATTAACCGCATCTCGTCTAAAGTTTAATCTATAT
       R  R  E  V  I  S  N  I  K  N  V  A  D  R  R  F  N  L  R  Y  124

12001 AGGCCGAATCTATGATATTGTTGATAATACAACGGTTTAATGCACACAGTATTATCTACG
      <L  G  F  R  H  Y  Q  Q  Y  Y  L  P  K  I  C  V  T  N  D  V

AAACTTTGATAAGTTAGATCAGTGTACGTATATTTAGATGTTTTCAGCTTAGCTAATCCT
       F  S  Q  Y  T  L  D  T  Y  T  Y  K  S  T  K  L  K  A  L  G  84

12121 GATATTAATTCTGTAAATGCTGGACCCAGATCTCTTTTTCTCAAATCCATAGTCTTCAAT
      <S  I  L  E  T  F  A  P  G  L  D  R  K  R  L  D  M  T  K  L

AATTCTATTCTAGTATTACCTGATGCAGGCAATAGCGACATAAACATAGAAAACGAATAA
       L  E  I  R  T  N  G  S  A  P  L  L  S  M  F  M  S  F  S  Y  44

12241 CCAAACGGTGAGAAGACAATATTATCATCTTGAATATTTTTATACGCTACTATACCGGCA
      <G  F  P  S  F  V  I  N  D  D  Q  I  N  K  Y  A  V  I  G  A

TTGGTAAATCCTTGCAGACGATAGGTAGACACTGAACACGTTAACGATAGTATCAATAAC
       N  T  F  G  Q  L  R  Y  T  S  V  S  C  T  L  S  L  I  L  L  4

12361 GCAATCATGATTTTATGGTATTAATAATTAACCTTATTTTTATGTTCGGTATAAAAATTA
      <A  I  M     <K2L  42.3kDa

TTGATGTCTACACATCCTTTTGTAATTGACATCTATATATCCTTTTGTATAATCAACTCT
      <Q  H  R  C  M  R  K  Y  N  V  D  I  Y  G  K  T  Y  D  V  R  69

12481 AATCACTTTAACTTTTACAGTTTTCCCTACCAGTTTATCCCTATATTCAACATATCTATC
      <I  V  K  V  K  V  T  K  G  V  L  K  D  R  Y  E  V  Y  R  D

CATATGCATCTTAACACTCTCTGCCAAGATAGCTTCAGAGTGAGGATAGTCAAAAAGATA
       M  H  M  K  V  S  E  A  L  I  A  E  S  H  P  Y  D  F  L  Y  29

12601 AATGTATAGAGCATAATCCTTCTCGTATACTCTGCCCTTTATTACATCGCCCGCATTGGG
      <I  Y  L  A  Y  D  K  E  Y  V  R  G  K  I  V  D  G  A  N  P

CAACGAATAACAAAATGCAAGCATCTTGTTAACGGGCTCGTAAATTGGGATAAAAATTAT
       L  S  Y  C  F  A  L  M     <K3L  10.5kDa

12721 GTTTTTATATCTATTTTATTCAAGAGAATATTCAGGAATTTCTTTTTCCGGTTGTATCTC
                                <E  L  S  Y  E  P  I  E  K  E  P  Q  I  E

ATCGCAGTATATATCATTTGTACATTGTTTCATATTTTTTAATAGTTTACACCTTTTAGT
       D  C  Y  I  D  N  T  C  Q  K  M  N  K  L  L  K  C  R  K  T  391

12841 AGGACTAGTATCGTACAATTCATAGCTGTATTTTGAATTCCAATCACGCATAAAAATATC
      <P  S  T  D  Y  L  E  Y  S  Y  K  S  N  W  D  R  M  F  I  D

TTCCAATTGTTGACGAAGACCTAATCCATCATCCGGTGTAATATTAATAGATGCTCCACA
       E  L  Q  Q  R  L  G  L  G  D  D  P  T  I  N  I  S  A  G  C  351
```

FIG.8L

```
12961 TGTATCCGTAAAAGTAATTTCCTGTCCAATTTGAGGTACCTATATAGGCCGTTTTATCGGT
      <T  D  T  F  Y  N  G  T  W  N  S  T  G  I  Y  A  T  K  D  T

TACCATATATTTGGCATGGTTTACCCTAGAATACGGAATGGGAGGATCAGCATCTGGTAC
       V  M  Y  K  A  H  N  V  R  S  Y  P  I  P  P  D  A  D  P  V   311

13081 AATAAATAGCTTTACTTCTATATCTATGTTTTTAGATTTTAGCATAGCGATAGATCTTAA
      <I  F  L  K  V  E  I  D  I  N  K  S  K  L  M  A  I  S  R  L

AAAGTTTCTCATGATAAACGAAGATCGTTGCCAGCAACTAATCAATAGCTTAACGGATAC
       F  N  R  M  I  F  S  S  R  Q  W  C  S  I  L  L  K  V  S  V   271

13201 TTGTCTGTCTATAGCGGATCTTCTTAATTCATCTTCTATATAAGGCCAAAACAAAATTTT
      <Q  R  D  I  A  S  R  R  L  E  D  E  I  Y  P  W  F  L  I  K

ACCCGCCTTCGAATAAATAATAGGGATAAAGTTCATAACAGATACATAAACGAATTTACT
       G  A  K  S  Y  I  I  P  I  F  N  M  V  S  V  Y  V  F  K  S   231

13321 CGCATTTCTAATACATGACAATAAAGCGGTTAAATCATTGGTTCTTTCCATAGTACATAG
      <A  N  R  I  C  S  L  L  A  T  L  D  N  T  R  E  M  T  C  L

TTGTTGCGGTGCAGAAGCAATAAATACAGAGTGTGGAACACCACTTACGTTAATACTAAG
       Q  Q  P  A  S  A  I  F  V  S  H  P  V  G  S  V  N  I  S  L   191

13441 AGGATGATCTGTATTATAATACGACGGATAAAAGTTTTTCCAATTATATGGTAGATTGTT
      <P  H  D  T  N  Y  Y  S  P  Y  F  N  K  W  N  Y  P  L  N  N

AACTCCAAGATACCAGTATACCTCAAAAATTTGAGTGAGATCCGCTGCCAAGTTCCTATT
       V  G  L  Y  W  Y  V  E  F  I  Q  T  L  D  A  A  L  N  R  N   151

13561 ATTGAAGATCGCAATACCCAATTCTTTGACCTGAGTTAGTGATCTCCAATCCATGTTAGC
      <N  F  I  A  I  G  L  E  K  V  Q  T  L  S  R  W  D  M  N  A

GCTTCCTAAATAAATATGTGTATTATCAGATATCCAAAATTTTGTATGAAGAACTCCTCC
       S  G  L  Y  I  H  T  N  D  S  I  W  F  K  T  H  L  V  G  G   111

13681 TAGGATATTTGTAATATCTATGTATCGTACTTCAACTCCGGCCATTTGTAGTCTTTCAAC
      <L  I  N  T  I  D  I  Y  R  V  E  V  G  A  M  Q  L  R  E  V

ATCCTTTAATGGTTTGTTAGATTTATTGACGGCTACTCTAACTCGTACTCCTCTTTTGGG
       D  K  L  P  K  N  S  K  N  V  A  V  R  V  R  V  G  R  K  P    71

13801 TAATTGTACAATCTCGTTTAATATTATCGTGCCGAAATTCGTACCCACTTCATCCGATAA
      <L  Q  V  I  E  N  L  I  I  T  G  F  N  T  G  V  E  D  S  L

ACTCCAATAAAAAGATGATATATCTAGTGTTTTTGTGGTATTGGATAGAATTTCCCTCCA
       S  W  Y  F  S  S  I  D  L  T  K  T  T  N  S  L  I  E  R  W    31

13921 CATGTTAAATGTAGACAAATATACTTTATCAAATTGCATACCTATAGGAATAGTCTCTGT
      <M  N  F  T  S  L  Y  V  K  D  F  Q  M  G  I  P  I  T  E  T

AATCACTGCGATTGTATTATCCGGATTCATTTTATTTGTTAAAAGAATAATCCTATATCA
       I  V  A  I  T  N  D  P  N  M       <K4L 48.9kDa
```

FIG.8M

```
14041 CTTCACTCTATTAAAAATCCAAGTTTCTATTTCTTTCATGACTGATTTTTTAACTTCATC

CGTTTCCTTATGAAGATGATGTTTGGCACCTTCATAAATTTTTATTTCTCTATTACAATT
                                                    <K  E  I  V  I   132
14161 TGCATGTTGCATGAAATAATATGCACCTGAAACATCACTAATCTCATTGTTTGTTCCCTG
      <Q  M  N  C  S  I  I  H  V  Q  F  M  V  L  R  M  T  Q  E  R

GAGTATGAGAGTCGGGGGGTGTTAATCTTGGAAATTATTTTTCTAACCTTGTTGGTAGCC
       S  Y  S  L  R  P  T  N  I  K  S  I  I  K  R  V  K  N  T  A   92
14281 TTCAAGACCTGACTAGCAAATCCAGCCTTAATTTTTTCATGATTGATTAATGGGTCGTAT
      <K  L  V  Q  S  A  F  G  A  K  I  K  E  H  N  I  L  P  D  Y

TGGTATTTATAAACTTTATCCATATCTCTAGATACTGATTCTGGACATAGCTTTCCGACT
       Q  Y  K  Y  V  K  D  M  D  R  S  V  S  E  P  C  L  K  G  V  52
14401 GGCGCATTTGGTGTGATGGTTCCCATAAGTTTGGCAGCTAGCAGATTCAGTCTTGAAACA
      <P  A  N  P  T  I  T  G  M  L  K  A  A  L  L  N  L  R  S  V
              *************

GCATCTGCATTAACTAGAGGAGACATTAGAATCATTGCTGTAAACAAGTTTGGATTATCG
       A  D  A  N  V  L  P  S  M  L  I  M  A  T  F  L  N  P  N  D   12
14521 TAAGAGGCTAGTATAGAAATTGTTGCTCCCATGGAATGACCCAATAAGTAGATTTAATAG
      <Y  S  A  L  I  S  I  T  A  G  M    <K5L 15.2KDa            <Y

TTACCACGTGCTGTACCAAAGTCATCAATCATCATTTTTTCACCATTACTTCTTCCATGT
       N  G  R  A  T  G  F  D  D  I  M  M  K  E  G  N  S  R  G  H   61
14641 CCAATATGATCATGTGAGAATACTAAAATTCCTAACGATGATATGTTTTCAGCTAGTTCG
      <G  I  H  D  H  S  F  V  L  I  G  L  S  S  I  N  E  A  L  E

TCATAACGTCCAGAATGTTTACCAGCTCCATGACTTATGAATACTAATGCCTTAGGATAT
       D  Y  R  G  S  H  K  G  A  G  H  S  I  F  V  L  A  K  P  Y   21
14761 GTAATAGGTTTCCAATATATGTAATCATTGTCCAGATTGAACATACAGTTTGCACTCATG
      <T  I  P  K  W  Y  I  Y  D  N  D  L  N  F  M  C  N  A  S  M

ATTCACGTTATATAACTATCAATATTAACAGTTCGTTTGATGATCATATTATTTTTATGt
      <K6L 9.1kDa

14881 TTTATTGATAATTGTAAAAACATACAATTAAATCAATATAGAGGAAGGAGACGGATACTG
          K7R> 17.5kDa   M  A  T  K  L  D  Y  E  D  A  V  F  Y  F>
      TCTTTTGTGAGATAGTCATGGCGACTAAATTAGATTATGAGGATGCTGTTTTTTACTTTG

V  D  D  D  K  I  C  S  R  D  S  I  I  D  L  I  D  E  Y  I
15001 TGGATGATGATAAAATATGTAGTCGCGACTCCATCATCGATCTAATAGATGAATATATTA
                                                          <Y  I  F  I  N

T  W  R  N  H  V  I  V  F  N  K  D  I  T  S  C  G  R  L  Y>
      CGTGGAGAAATCATGTTATAGTGTTTAACAAAGATATTACCAGTTGTGGAAGACTGTACA
       R  P  S  I  M  N  Y  H  K  V  F  I  N  G  T  T  S  S  Q  V   40
```

FIG.8N

```
         K  E  L  M  K  F  D  D  V  A  I  R  Y  Y  G  I  D  K  I  N
15121 AGGAATTGATGAAGTTCGATGATGTCGCTATACGGTACTATGGTATTGATAAAATTAATG
      <L  F  Q  H  L  E  I  I  D  S  Y  P  V  I  T  N  I  F  N  I

E  I  V  E  A  M  S  E  G  D  H  Y  I  N  F  T  K  V  H  D>
      AGATTGTCGAAGCTATGAGCGAAGGAGACCACTACATCAATTTTACAAAAGTCCATGATC
      L  N  D  F  F  S  H  A  F  S  V  V  D  I  K  C  F  D  M  <K8L 7.5kDa

Q  E  S  L  F  A  T  I  G  I  C  A  K  I  T  E  H  W  G  Y
15241 AGGAAAGTTTATTCGCTACCATAGGAATATGTGCTAAATCACTGAACATTGGGGATACA

K  K  I  S  E  S  R  F  Q  S  L  G  N  I  T  D  L  M  T  D>
      AAAAGATTTCAGAATCTAGATTCCAATCATTGGGAAACATTACAGATCTGATGACCGACG

D  N  I  N  I  L  L  F  L  E  K  K  L  N>
15361 ATAATATAAACATCTTGATACTTTTTCTAGAAAAAAAATTGAATTGATGATATAGGGGTC

TTCATAACGCATAATTATTACGTTAGCATTCTATATCCGTGTTAAAAAAAATTATCCTAT

15481 CATGTATTTGAGAGTTTTATATGTAGCAAACATGATAGCTGTGATGCCAATAAGCTT
```

FIG.80

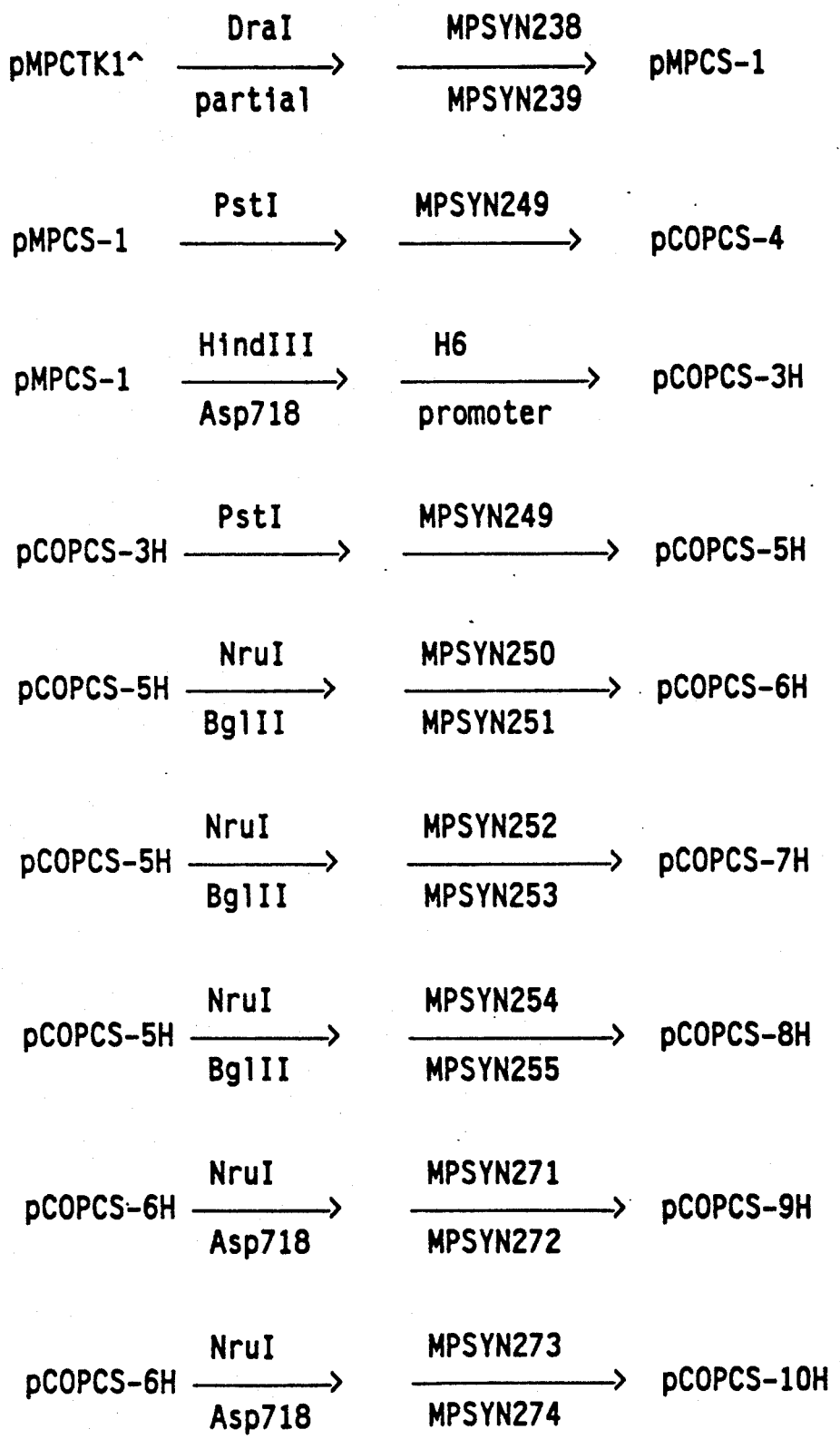

FIG. 16-1

```
           HindIII        Asp718         SalI           BglII
MPSYN238 5' AAGCTTCTCGAGGTACCCGGGTCGACTCTAGAGATCTGCAGTAAATAATAATTTTATTT 3'
MPSYN239 3' TTTCGAAGAGCTCCATGGGCCCAGCTGAGATCTAGAGATCTAGAGCTCATTATTATTATTAAAAATAAA 5'
                 XhoI          SmaI                    XbaI  PstI
```

```
           NruI                   Asp718                              PstI
MPSYN250 5' CGATATCCGTTAAGTTTGTATCGTAATG-GTA-CCC-TCG-AGC-TGC-AGC-CCG-GGG- 3'
MPSYN251 3' GCTATAGGCAATTCAAACATAGCATTAC-CAT-GGG-AGC-TCG-ACG-TCG-GGC-CCC- 5'
                                                XhoI              SmaI
```

```
           SalI               BglII
MPSYN250 5' TCG-ACT-CTA-GAA              3'        MPSYN250
MPSYN251 3' AGC-TGA-GAT-CTT-CTA-G        5'        MPSYN251
                   XbaI
```

```
           NruI                   Asp718                              PstI
MPSYN252 5' CGATATCCGTTAAGTTTGTATCGTAATG-GGT-ACC-CTC-GAG-CTG-CAG-CCC-GGG- 3'
MPSYN253 3' GCTATAGGCAATTCAAACATAGCATTAC-CCA-TGG-GAG-CTC-GAC-GTC-GGG-CCC- 5'
                                                XhoI              SmaI
```

FIG. 16-2

```
              SalI      SstII
              GTC-GAC-TCT-AGA-CCG-CGG-A                              3'  MPSYN252
              CAG-CTG-AGA-TCT-GGC-GCC-TCT-AG                         5'  MPSYN253
                        XbaI    BglII

NruI                                  Asp718              PstI
MPSYN254  5'  CGATATCCGTTAAGTTTGTATCGTAATG-GGG-TAC-CCT-CGA-GCT-GCA-GCC-CGG-
MPSYN255  3'  GCTATAGGCAATTCAAACATATAGCATTAC-CCC-ATG-GGA-GCT-CGA-CGT-CGG-GCC-
                                                             XhoI              SmaI

SalI      SnaBI                     Asp718
              GGT-CGA-CTC-TAG-ATA-CGT-AA                             3'  MPSYN254
              CCA-GCT-GAG-ATC-TAT-GCA-TTC-TAG                        5'  MPSYN255
                        XbaI    BglII

NruI                                 Asp718
MPSYN271  5'  CGATATCCGTTAAGTTTGTATCGTAATG-AGT-ACT-G                 3'
MPSYN272  3'  GCTATAGGCAATTCAAACATAGCATTAC-TCA-TGA-CCA-TG            5'
                                                      ScaI

NruI                                 Asp718
MPSYN273  5'  CGATATCCGTTAAGTTTGTATCGTAATG-ACC-GCG-GG                3'
MPSYN274  3'  GCTATAGGCAATTCAAACATAGCATTAC-TGG-CGC-CCC-ATG           5'
                                                      SstII
```

FIG. 17-1 pMPCS-1
```
HindIII   Asp718     SalI       BglII
AAGCTTCTCGAGGTACCCGGGTCGACTCTAGATCTGCAGTAAATAAATAATTTTATTT
          XhoI   SmaI        XbaI   PstI
``` pMPCS-4
```
HindIII   Asp718     SalI       BglII
AAGCTTCTCGAGGTACCCGGGTCGACTCTAGATCTATAAATAAATAATTTTATTT
          XhoI   SmaI        XbaI
``` pCOPCS-3H
```
HindIII                                        -100
AAGCTTCTTTATTCTATACTTAAAAAGTGAAAATAAATACAAAGGTTCTTGAGGTTGTGTTAA
                     -50
                                 NruI                      -1
ATGAAAGCCGAGAATAATCATAAATTATTTCATTTATCGCGATATCCGTTAAGTTTGTATCGTA Asp718     SalI       BglII
[CTCGAGGGTACCCGGGTCGACTCTAGATCTGCAGTAAATAAATAATTTTATTT]
 XhoI   SmaI        XbaI   PstI
```

FIG. 17-2 pCOPCS-5H  [CTCGAGGGTACCCGGGTCGACTCTAGATCTATAAATAAATTTTATTT]
            XhoI    SmaI      XbaI
            Asp718  SalI  BglII pCOPCS-6H  [ATG-GTA-CCC-TCG-AGC-TGC-AGC-CCG-GGG-TCG-ACT-CTA-GAA-GAT-CTA-TAA-
            Asp718   XhoI   PstI      SmaI  SalI     XbaI     BglII
ATAAATAATTTTATTT]

pCOPCS-7H  [ATG-GGT-ACC-CTC-GAG-CTG-CAG-CCC-GGG-GTC-GAC-TCT-AGA-CCG-CGG-
            Asp718   XhoI   PstI      SmaI  SalI     XbaI    SstII
AGA-TCT-ATA-AAT-AAA-TAATTTTTATTT]
BglII

FIG. 17-3 pCOPCS-8H

```
    Asp718                    PstI                    SalI              SnaBI
[ATG-GGG-TAC-CCT-CGA-GCT-GCA-GCC-CGG-GGT-CGA-CTC-TAG-ATA-CGT-
              XhoI                    SmaI              XbaI

AAG-ATC-TAT-AAA-TAAATAATTTTTATTT]
BglII
``` pCOPCS-9H

```
         Asp718                    PstI              SalI
[ATG-AGT-ACT-GGT-ACC-CTC-GAG-CTG-CAG-CCC-GGG-GTC-GAC-TCT-AGA-
    ScaI              XhoI              SmaI              XbaI

SstII
CCG-CGG-AGA-TCT-ATA-AAT-AAA-TAATTTTTATTT]
         BglII
``` pCOPCS-10H

```
         Asp718                    PstI                    SalI
[ATG-ACC-GCG-GGG-TAC-CCT-CGA-GCT-GCA-GCC-CGG-GGT-CGA-CTC-TAG-
         SstII              XhoI              SmaI              XbaI

SnaBI
ATA-CGT-AAG-ATC-TAT-AAA-TAAATAATTTTTATTT]
              BglII
```

```
10321 AACAGATATTCCAGTATCAGATTATGCGTCCAGAGGGAGATGGGTTACACGGTGACTGTTGATATTGACGGTATGTATTGTAGATGCTCTCATGGTTATAC
        T  D  I  P  A  I  R  L  C  G  P  P  E  G  D  D  G  Y  C  L  H  G  D  C  I  H  A  R  D  I  D  G  M  Y  C  R  C  S  H  G  Y >
                                                             C11R (19K VGF)                                                      >

10441 AGGCATTAGATGTCAGCATGTAGTATTAGACTATCAACGTTCAGAAAAACCCAACTACAAAACGTTCATATATCCCATCTCCCGGTATTATGCTTGTATTAGTAGGCATTATTATTAT
        G  I  R  C  Q  H  V  V  L  V  D  Y  Q  R  S  E  N  P  N  T  T  S  Y  I  P  S  P  G  I  M  L  V  G  I  I  I  I >
                                                          C11R (19K VGF)                                                        >

10561 TATTACGTGTTGTCTATTATCGTGTTTATAGGTTCACTCGAAGAACTAATAAACTACCTCTACAAGATAATGGTTGTGCCATAATTTTTATAAATTTTTTTATGAGTATTTTTACAAAAAT
        I  T  C  C  L  L  S  V  Y  R  F  T  R  R  T  N  K  L  P  L  Q  D  M  V  V  P >
                        C11R (19K VGF)                                              >                           >Xba1

10681 GTATAAAGTGTATGTCTTATGTATATTTATAAAAATGCTAAATATGCGATGTATCTATGTTATTTATCTAAACAATACCTCTACCTCTAGATATTATACAAAAATTTTTTATTT
                                                                                                                        <K
                                                                                                                        <

10801 CAGCATATTAAAGTAAAATCTAGTTACCTTGAAAATGAATACAGTGGGTGGTTCCGTATCACCAGTAAGAACATAATAGTCGATTGAGATTTTGCATACAATACTAG
      <L  M  N  F  Y  F  R  T  V  K  F  I  F  V  T  P  P  E  T  D  G  T  L  V  Y  Y  D  F  V  T  D  S  Q  S  K  A  Y  L  V  L
      <                                              C10L (42K)
      >Xba1

10921 TCTAGAAAGAATTTGTAATCATCTTCTGTGACGGAGTCCATATATCTGTAGTTTATCAGTGTCCCATGCTATATTCCTGTATCATCATTAGTTAATGAAAATAACTC
      <R  S  L  F  K  Y  D  D  E  T  V  P  P  T  W  I  D  T  D  D  D  L  K  D  T  D  W  A  I  N  R  N  D  D  N  T  L  S  F  L  E
      <                                              C10L (42K)                                                                   >Bgl2

11041 TCGTGCTTCAGAAAAGTCAAATATTGTATCCATACATACATCTCCAAAACTATCGCTTATCTTTAACGATACCTAGATGGTTATTTACTAACAGACATTTTCCAGA
      <R  A  E  S  F  F  D  F  I  T  D  M  C  V  D  G  F  S  D  S  I  R  K  D  K  V  I  G  I  G  L  N  N  N  V  L  L  C  K  G  S
      <                                              C10L (42K)
```

FIG. 19L

```
11161 TCTATTGACTATAACTCCTAGTTTCCACATCAACCAAGTAATGATCATCTATTGTTATATAACATAACTCTTTCCGTTTTATCAGTATGTATATCTATATTAACGTCGTC
      <R  N  V  I  V  G  I  T  E  V  D  V  L  Y  H  D  D  I  T  I  Y  C  C  L  E  E  K  G  N  K  D  T  H  I  D  I  N  V  D  D
                                                      C10L (42K)
                                                                            >Xbal
                                                               >Xbal                    >Dral
11281 GTGTAGTGAATAGTAGTTATTGATCTATTATATGAAACGGATATGTCTAGAACGGCAATTGTTTACGTCCAGTTAACACTTCTCTTGATTTAAAGTCTAGAGTCTTGCAAACATAAT
      <N  Y  H  I  T  T  I  S  R  N  Y  S  V  S  I  D  L  V  A  I  T  K  R  G  T  L  V  K  K  S  K  F  D  L  T  K  A  F  M  I
                                                      C10L (42K)                                            C10L (42K)
                                                                       >Hpal                                                                  >Kpn1
11401 ATCCTTATCCGACTTTATATTTCCTGAGGGTGGTATAATTTTATTTTGCCTCCCACATATCGGTGTTTCCAAATATATTACTAGACAATATTCCATAGTTATTAGTTAAGGGTACCCA
      <D  K  D  S  K  I  N  G  T  P  H  Y  L  K  I  K  G  G  C  I  P  T  E  L  Y  I  I  V  L  C  Y  E  M  Y  N  N  T  L  P  P  W
                                                      C10L (42K)
                                                                             >Clal                          ORF E
11521 ATTAGAACACGTACGCTTATTATCATCATTGGATCGTATTTCATAAAGTTATTGTACTATCGATGTCAACACATTCTACATTTTTTAATCGTCTATATAGTATTTTCTGATATTTC
                                                                          M  S  T  H  S  T  F  F  F  N  R  L  Y  S  I  F  L  I  F  S>
      <N  S  C  T  R  K  N  D  D  N  P  D  Y  K  M  F  T  I  I  T  S  D  I  D  V  C  E  V  N  K  L  R  R  Y  L  I  K  R  I  N  E
                                                      C10L (42K)
                                                    >Dral
                                                                            ORF F
11641 TATAATATCAGAATTGTCTTCCATCGGAAGTTGTATACTATCAGAATCAGTTTAAATAATTCTCTGATGTCATTCCTTATACAATCAAATTCATTATTAAACAGTTAATAGT
                                                  ORF E  K  F  L  E  R  I  D  N  R  I  C  D  F  E  N  N  F  L  K  I  T
      <I  I  D  S  N  D  E  M  P  L  Q  I  S  D  S  D  T  V  H  K
                                                      C10L (42K)                    N  N  S  L  M  S  F  L  I  Q  S  N  S  L  I  V>
      <I  I  S  E  L  S  S  I  G  S  C  I  L  S  E  S  V  T  C  L
```

```
12961 ATCAATATACGGCTTACAAAGTTTAGTATCGATAACAACATCCAACTCACGGCATAGAGAAGGTAGGGAATAATGGCATAATATTTATTAGGTTATCATCATTGTCATTATCTACAACTAA
      <D  I  Y  P  K  C  L  K  L  I  S  L  V  D  L  E  R  M  S  F  T  P  F  L  P  M  I  N  I  L  N  D  D  N  D  N  D  V  V  L
                   >ClaI                                                           C9L (77K) [SPLIT]
                                    >DraI
13081 GTTTCCATTTTTAAAATATACTCGACAACTTTAGGATCTCTATTGCCAAATTTTTGAAAATATTTATTTATATGCTTAAATCTATATAATGTAGCTCCTTCATCAATCATACATTTAAT
      <N  G  N  K  L  I  Y  E  V  V  K  P  D  R  N  G  F  K  Q  F  Y  K  N  I  H  K  F  R  Y  L  T  A  G  E  D  I  M  C  K  I
                                                              C9L (77K) [SPLIT]
                                    >BglII
13201 AACATTGATGTATACTGTATGATGATAAGATACATATTCTAACAATAGATCTTGTATAGAAACTGTATATCTTTAAGAATTGTGGATATTAGGATATTATTACGTAAACTATTACAATTC
      <V  N  I  Y  V  T  H  Y  S  V  Y  E  L  L  L  L  D  Q  I  S  V  T  Y  R  K  L  I  T  S  I  I  N  N  R  L  S  N  C  L  E
                                                              C9L (77K) [SPLIT]
                                    >ClaI
13321 TAAAATATAAAACGTATCACGGTCGAATAATAGTTGATCAACTATATAAATTCGATTTTGTGATTTTCTCCTAAACTGTTACGTAATAAATAGTTAGATAGAATATTCATTAGTTCATG
      <L  I  Y  F  T  D  R  D  F  L  L  Q  D  D  V  I  Y  N  D  I  K  H  N  K  K  R  F  Q  K  R  L  Y  N  S  L  I  N  M  L  E  H
                                                              C9L (77K) [SPLIT]
13441 ACCACTAGTAGTTACTATCGAATAACGGTCAAATATTTCCCGTTTAATATCGCATTGTCAAGATAATAGTTGGTATGTTCACGATAAGTATAATAACGCATCTCTTTTTGTG
      <G  S  S  Y  N  S  D  F  L  A  D  F  I  E  R  K  I  D  C  K  D  L  Y  Y  L  T  T  H  E  R  Y  T  Y  R  M  E  K  K  H
                                                              C9L (77K) [SPLIT]
13561 TGAAATTAAATAGTTATTACGTCCAAAGATGTAGACCATCTTGTGACCTAGTAATAATAATATAATAGAGAACTGTTTACCCATTCTATCATCATCTATCATAATCAGTGGTGTAGTCGTA
      <S  I  L  Y  N  I  V  D  L  S  T  A  Y  G  D  Q  S  R  T  I  I  Y  Y  L  V  T  K  G  M  R  D  D  Y  D  T  T  Y  D  Y
                                                              C9L (77K) [SPLIT]
```

FIG.190

```
13681 ATCGTAATCGTCTAATTCATCATCCCAATTATAATATTCACCAGCACGTCTAATCTGTTCTATTTTGATCTTGTATCCATACTGTATGTTGCTACATGTAGGTATTCCTTTATCCAATAA
     <D  Y  D  D  L  E  D  D  W  N  Y  Y  E  G  A  R  R  I  Q  E  I  K  Y  G  Y  Q  I  N  S  C  T  P  I  G  K  D  L  L
                                                    C9L (77K) [SPLIT]                  M  L  H  V  G  I  P  L  S  N  N>
        >DraI                                                                              ORF D

13801 TAGTTTAAAACACATCTACATTGGGATTTGATGTTGTAGCGTATTTCTCTACAATATTAATACCATTTTGATACTATTTATTTCTATACCTTTCGAATTAGTAATTCAATAAGTCTAT
     <L  K  F  V  D  V  N  P  N  S  T  T  A  Y  K  E  V  I  N  N  G  N  K  I  S  N  I  E  I  G  K  S  I  L  L  K  L  D  I
     S  L  N  T  S  T  L  G  F  D  D  V  V  A  Y  F  S  T  I  L  P  F  L  I  L  F  F  I  S  N  I  E  I  G  K  S  I  L  L  K  L  D  I
                                                    ORF D                                  C9L (77K) [SPLIT]
        >ClaI                                                                                          >SalI

13921 ATCGATGTTATCAGAACATAGATATTCGAATATATCAAAATCATTGATATTTTATAG
     <D  I  N  D  S  C  L  Y  E  F  I  D  F  D  N  I  N  K  Y
     S  M  L  S  E  H  R  Y  S  N  I  S  K  S  L  I  F  L>
                     C9L (77K) [SPLIT]
                     ORF D
```

FIG. 19P

```
  1 TAGATATTCACGGCGTGCTAGTGTTAGGATGGTATTATCTGGTGGTGAAATGTCCGTTATATAATCTACAAAACAATCATCGCATATAGTATGCGATAGTAGTAAACATTTTATAGT
    <L  Y  E  R  T  S  T  N  P  I  T  N  D  P  P  S  I  D  T  I  Y  D  V  F  C  D  D  C  I  T  H  S  L  L  T  F  M  K  I  T
                                                       F1L [SPLIT]

121 TTTTACTGGATTCATACATCGTCTACCCAATTCGGTTATAAATGAAATTGTGCCAATCTTACACCCAACCCTTGTATCATTAGTATAGTATTAACTTCGTTATTTATGTCATAAAC
    <K  V  P  N  M  C  R  R  G  L  E  T  I  F  S  I  T  A  L  R  V  G  L  G  K  N  D  M  L  I  T  N  V  E  N  N  I  D  Y  V
                                                       F1L [SPLIT]

241 TGTAAATGATTTGTAGATGCCATATCATCATGATATTCATGTCCCTATTAACTTATCACAATATGTTGATAATATCTATATGATCTAGTCTTTGTGGGCAA
    <T  F  S  K  T  S  A  M  D  Y  M  I  N  M  D  R  N  Y  D  N  S  Y  K  D  C  Y  I  N  I  D  I  Y  S  R  T  K  T  P  L
                                                       F1L [SPLIT]

361 CTGTCTATACAAGTCGTCTAAACGTTGTTTACTCATATAGTATCGAACAGCCATCATTACATGGTCCCGTTCGTGATAGATAATGAGTAGTTAGTGGACTTGTCAAATCTATATAC
    <Q  R  Y  L  D  D  L  R  Q  K  S  M  Y  Y  R  V  A  M  M  V  H  D  R  E  T  S  L  Y  D  L  I  N  T  S  K  D  F  R  Y  V
                                                       F1L [SPLIT]

481 CATATTTCTGGAAGTGGATATACAAGTCGTGATCAACATTATTGCTAGCCTCATCTTCTATATCCTGTACTACCATTATCATCTACGATATTATTACACAT
    <M  N  E  P  L  P  Y  V  V  Y  D  H  D  V  N  N  S  A  E  I  D  Q  V  I  G  N  D  I  D  D  V  Y  D  V  I  N  N  C  M
                                                       F1L [SPLIT]
                                                                                              >XbaI
601 AAACATCGACAACAACATACTATTGTTTATTATCTAAGTCCTGTTGATCCAAACCCTGATCTCCTCTATTGTACTATCTAGAGATTGTACTTCTTCCAGTTCTGGATAATATACGTTGA
    <F  M  S  L  M
      F1L [SP]
                   <R  L  G  T  S  G  F  G  Q  D  G  R  N  T  S  D  L  S  Q  V  E  E  L  E  P  Y  Y  I  R  Q
                      <                                              F2L

721 TAGATTAGCTGAGCTATTCTATCTCCAGTATTCTATCCATTATTAAACGTACATTTCCATTATTAATAAGAATGACTCCTATGTTTCCCCTATAATCTTGTCTATTACACCACCTCTATCA
    <Y  I  L  Q  A  I  R  D  G  T  N  V  N  F  T  C  K  G  N  N  I  L  I  V  G  I  N  G  R  Y  D  E  D  I  V  G  G  G  I  D
      <                                                                F2L

841 ATGCCTTTAGTGACAGACCAGACCTAGGAGCTATTCTACCATGACATAACTTAGGCATGGACATAATATCTCTTAATTAACTGTCTTTCTCCTGGAGGGATAGTATAATCGTAA
    <I  G  K  L  S  L  G  S  R  P  A  I  R  G  Y  C  I  K  P  M  S  M  S  I  D  T  K  I  L  Q  R  E  G  P  P  I  T  Y  D  Y
      <                                    F2L                        F2L
```

RECOMBINANT POXVIRUS HOST RANGE SELECTION SYSTEM

This invention was made with Government support under contract DAMD17-85-C-5232 awarded by the Department of the Army. The Government has certain rights in this invention.

CROSS REFERENCE TO RELATED APPLICATIONS

This application is a continuation of application Ser. No. 07/478,179, filed Feb. 14, 1990, now abandoned which is a continuation-in-part of application Ser. No. 07/320,471, filed Mar. 8, 1989, now U.S. Pat. No. 5,155,020.

FIELD OF THE INVENTION

The present invention relates to modified recombinant viruses, methods for expressing gene products in a host using such modified recombinant viruses, and to vaccines comprising such modified recombinant viruses.

The present invention also relates to modified poxvirus, particularly modified vaccinia virus, and to methods of making and selecting for the same. More in particular, the invention relates to a selection system for the cloning and expression of an open reading frame in recombinant poxvirus, particularly recombinant vaccinia virus.

Several publications are referenced in this application by arabic numerals within parentheses. Full citation to these references is found at the end of the specification immediately preceding the claims. These references describe the state-of-the-art to which this invention pertains.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (32).

Specifically, the recombinant poxviruses are constructed in two steps known in the art and analogous to the methods for creating synthetic recombinants of the vaccinia virus described in U.S. Pat. No. 4,603,112, the disclosure of which patent is incorporated herein by reference.

First, the DNA gene sequence to be inserted into the virus, particularly an open reading frame from a non-pox source, is placed into an E. coli plasmid construct into which DNA homologous to a section of nonessential DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a nonessential region of pox DNA. The resulting plasmid construct is then amplified by growth within E. coli bacteria (4) and isolated (5,22).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Unperturbed, successful recombination occurs at a frequency of approximately 0.1%.

A basic screening strategy for recovering those viruses modified by a successful recombination involves in situ hybridization of recombinants on replica filters with a radiolabeled probe homologous to the inserted sequences (26,28). A number of modifications have been reported to increase the efficiency of recombination itself o to facilitate the identification of recombinants. Among these modifications are included: using single stranded donor DNA (38); identification of recombinants expressing unique enzymatic functions such as $^{125}$Iododeoxycytidine incorporation into DNA via expression of the Herpes simplex virus thymidine kinase (28); chromogenic substrates for (co)expression of foreign genes along with B galactosidase (3,29); selection for thymidine kinase expression (20,28); antibody based reactions to visualize recombinant plaques (21); use of conditional lethal ts or drug mutants (9,18); selection of recombinants using the neomycin resistance gene from Tn5 and the antibiotic G418 (11); or selection pressures with mycophenolic acid and the E. coli gpt gene (2,8).

Disadvantageously, these known methods for identifying or selecting recombinant poxvirus all involve tedious multi-step identification of the recombinants, the introduction of radiochemicals, chromogenic substrates, biochemicals useful for selection such as mycophenolic acid and bromodeoxyuridine which may be detrimental (mutagenic) to the viral genome itself, use of serological reagents that may introduce contaminants, and typically the presence of an exogenous gene in the final recombinant in addition to the foreign genetic element of interest.

It can thus be appreciated that provision of a method of making and selecting for poxvirus recombinants, particularly vaccinia recombinants, which method avoids the previously discussed problems, would be a highly desirable advance over the current state of technology.

Methods have been developed in the prior art that permit the creation of recombinant vaccinia viruses and avipox viruses by the insertion of DNA from any source (e.g. viral, prokaryotic, eukaryotic, synthetic) into a nonessential region of the vaccinia or avipox genome, including DNA sequences coding for the antigenic determinants of a pathogenic organism. Recombinant vaccinia viruses created by these methods have been used to induce specific immunity in mammals to a variety of mammalian pathogens, all as described in U.S. Pat. 4,603,112, incorporated herein by reference. Recombinant avipox viruses created by these methods have been used to induce specific immunity in avian species (41) and in non-avian species (42).

Unmodified vaccinia virus has a long history of relatively safe and effective use for inoculation against smallpox. However, before the eradication of smallpox, when unmodified vaccinia was widely administered, there was a modest but real risk of complications in the form of generalized vaccinia infection, especially by those suffering from eczema or immunosuppression. Another rare but possible complication that can result from vaccinia inoculation is post vaccination encephalitis. Most of these reactions resulted from inoculating individuals with skin diseases such as eczema or with impaired immune systems, or individuals in households with others who had eczema or impaired immunological responses. Vaccinia is a live virus, and is normally harmless to a healthy individual. However, it can be transmitted between individuals for several weeks after inoculation. If an individual with an impairment of the normal immune response is infected either by inoculation or by contagious transmission from a recently inoculated individual, the consequences can be serious.

Suitably modified virus mutants carrying exogenous genes which are expressed in a host as an antigenic determinant eliciting the production by the host of antibodies to a host pathogen with restricted replication of the virus in the host represent novel vaccines which avoid the drawbacks of conventional vaccines employing killed or attenuated live organisms. Thus, for instance, the production of vaccines from killed organisms requires the growth of large quantities of the organisms followed by a treatment which will selectively destroy their infectivity without affecting their antigenicity. On the other hand, vaccines containing attenuated live organisms present the possibility of a reversion of the attenuated organism to a pathogenic state. In contrast, when a recombinant poxvirus suitably modified is used as a vaccine, the possibility of reversion to a pathogenic organism is avoided since the poxvirus contains only the gene coding for the antigenic determinant of the disease-producing organism and not those genetic portions of the organism responsible for the replication of the pathogen.

Thus, it can be appreciated that a method which confers on the art the advantages of live virus inoculation but which reduces or eliminates the previously discussed problems would be a highly desirable advance over the current state of technology. This is even more important today with the advent of the disease known as acquired immune deficiency syndrome (AIDS). Victims of this disease suffer from severe immunological dysfunction and could easily be harmed by an otherwise safe live virus preparation if they came in contact with such virus either directly or via contact with a person recently immunized with a vaccine comprising such a live virus.

OBJECTS OF THE INVENTION

It is therefore an object of the present invention to provide a vaccine for inducing an immunological response in a host which has the advantages of a live virus vaccine, and which has few or none of the disadvantages of either a live virus vaccine or a killed virus vaccine as enumerated above.

It is a second object of this invention to provide modified recombinant viruses for use in such vaccines.

It is an additional object of this invention to provide a method for expressing a gene product in a host by inoculating the host with a modified recombinant virus which codes for and expresses the gene product in the host with restricted replication of the virus in the host.

It is also an object of the invention to provide methods for expressing a gene product in a cell cultured in vitro, which method comprises introducing into the cell a modified recombinant virus containing DNA which codes for and expresses the gene product with restricted replication of the virus in the cell.

It is a further object of this invention to provide modified recombinant viruses, which modified recombinant viruses express gene products in a host with restricted replication of the viruses in the host, and to provide a method of making such modified recombinant viruses.

It is a further object of this invention to provide rapid one-step identification of recombinant viruses and rapid screening for expression of the foreign open reading frames in the recombinants.

It is a further object of this invention to provide a method of making and selecting for a recombinant poxvirus, particularly recombinant vaccinia virus, and to provide DNA sequences, produced or involved as intermediates in the method.

It is a still further object of this invention to provide a selection system for the cloning and expression of an open reading frame in recombinant poxvirus, particularly recombinant vaccinia virus, wherein the recombinant virus contains no foreign gene other than the open reading frame of interest.

These and other objects and advantages of the present invention will become more readily apparent after consideration of the following.

STATEMENT OF THE INVENTION

In one aspect, the present invention relates to a modified recombinant virus having host range genes deleted therefrom so that the virus has restricted replication in a host, wherein the modified recombinant virus contains DNA which codes for and expresses a gene product in the host with restricted replication of the virus in the host. The virus according to the present invention is advantageously a poxvirus, particularly a vaccinia virus.

In another aspect, the present invention relates to a method for expressing a gene product in a host by inoculating the host with a modified recombinant virus having host range genes deleted therefrom so that the virus has restricted replication in the host. The modified recombinant virus contains DNA which codes for and expresses the gene product in the host even with restricted replication of the virus in the host. The virus used in the method according to the present invention is advantageously a poxvirus, particularly a vaccinia virus. The gene product expressed in the host is advantageously an antigen. More in particular, the host is a vertebrate and the antigen induces an immunological response in the vertebrate.

In yet another aspect, the present invention relates to a vaccine for inducing an immunological response in a host inoculated with the vaccine, said vaccine including a carrier and a modified recombinant virus having host range genes deleted therefrom so that the virus has restricted replication in the host. The modified recombinant virus contains DNA which codes for and expresses a gene product in the host even with restricted replication of the virus in the host. The Virus used in the vaccine according to the present invention is advantageously a poxvirus, particularly a vaccinia virus.

In a further aspect, the invention relates to a method for selecting for a recombinant poxvirus in a host by combining donor DNA and a modified poxvirus to form a recombinant poxvirus and identifying the recombinant poxvirus by its ability to replicate in the host. In a still further aspect, the invention relates to a method for cloning and expressing an open reading frame in a recombinant poxvirus in a host by combining donor DNA and a modified poxvirus to form a recombinant poxvirus, replicating the recombinant poxvirus in the host and expressing the open reading frame. According to the present invention, the modified poxvirus has a host range gene deleted therefrom so that the modified poxvirus does not replicate in the host and the donor DNA contains an open reading frame from a non-pox source and the host range gene for permitting the recombinant poxvirus to replicate in the host.

In still another aspect, the invention relates to a donor plasmid for making the recombinant poxvirus of the selection system. The donor plasmid contains an open reading frame from a non-pox source and a host range gene for permitting the recombinant poxvirus to replicate in the host. Advantageously, the donor plasmid may also contain a promoter upstream from the poxvirus host range gene, a translation initiation codon downstream from the promoter followed by unique multiple restriction sites, translational termination signal sequences and an early transcription termination signal sequence.

BRIEF DESCRIPTION OF THE DRAWINGS

A better understanding of the present invention will be had by referring to the accompanying drawings, in which:

FIG. 2A schematically shows a method for cloning of the host range gene K1L into the plasmid pMP528L and its insertion into vP293 to generate vaccinia virus vP457;

FIG. 2B is a map of the left end of vP293 through HindIII K;

FIG. 2C is a map of the left end of vP457 through HindIII K;

FIG. 3B shows the DNA sequence of the synthetic H6 promoter and downstream restriction sites present in pMP528HRH;

FIG. 3C shows the DNA sequence (with restriction sites, stop codons and early transcriptional termination signal) which replaces the bracketed sequence of FIG. 3B in plasmid pHES1;

FIG. 3D shows the DNA sequence (with restriction sites, stop codons and early transcriptional termination signal) which replaces the bracketed sequence of FIG. 3B in plasmid pHES2;

FIG. 3E shows the DNA sequence (with restriction sites, stop codons and early transcriptional termination signal) which replaces the bracketed sequence of FIG. 3B in plasmid pHES3;

FIG. 3F shows the DNA sequence (with restriction sites, stop codons and early transcriptional termination signal) which replaces the bracketed sequence of FIG. 3B in plasmid pHES4;

FIG. 4B shows the DNA sequences of the synthetic oligonucleotides HRL15-22;

FIG. 5 shows the DNA sequence of the vaccinia u promoter present in plasmids pHES31-34. Additionally, FIG. 5 shows in bracketed sequence the restriction sites, stop codons and early transcriptional termination signals present in pHES31-34 and the initiation codons present in pHES31-33;

FIG. 6B shows the DNA sequences of the synthetic oligonucleotides HRL33-40;

FIG. 7 shows the DNA sequence of the synthetic ATI promoter present in plasmids pHES61-64. Additionally, FIG. 7 shows in bracketed sequence the restriction sites, stop codons and early transcriptional termination signals present in pHES61-64 and the initiation codons present in pHES61-63;

FIG. 8, PARTS A-O, shows the DNA sequence (with restriction sites) of 15,537 bp located near the left end of the Copenhagen strain of vaccinia;

FIG. 15 schematically shows a method for the construction of a series of plasmids derived from pMPCTK1Δ;

FIG. 16 shows the DNA sequences of synthetic oligonucleotides MPSYN238, MPSYN239, MPSYN250-255 and MPSYN271-274;

FIGS. 17-1, 17-2, and 17-3 show the synthetic DNA sequence containing restriction sites, stop codons and early transcriptional termination signals present in plasmids pMPCS-1 and pMPCS-4. Additionally, FIG. 17 shows the synthetic H6 promoter region present in pCOPCS-3H and pCOPCS-5H through pCOPCS-10H. Additionally, FIG. 17 shows in bracketed sequence the restriction sites, stop codons and early transcriptional termination signals present in pCOPCS-3H and pCOPCS-5H through pCOPCS-10H and the initiation codons present in pCOPCS-6H through pCOPCS-10H;

FIG. 19, PARTS A-P, shows the DNA 13,978 bp sequence from HindIII C of the vaccinia virus Copenhagen genome, including coding sequences located to the left of the sequence presented in FIG. 8;

FIG. 20, PARTS A-R, shows the complete DNA sequence for HindIII F located immediately to the right of HindIII K in FIG. 8; and FIG. 21, PARTS A-U, shows the DNA sequence contained in HindIII B near the right terminus of the vaccinia virus genome.

DETAILED DESCRIPTION OF THE INVENTION

Figure 3A:
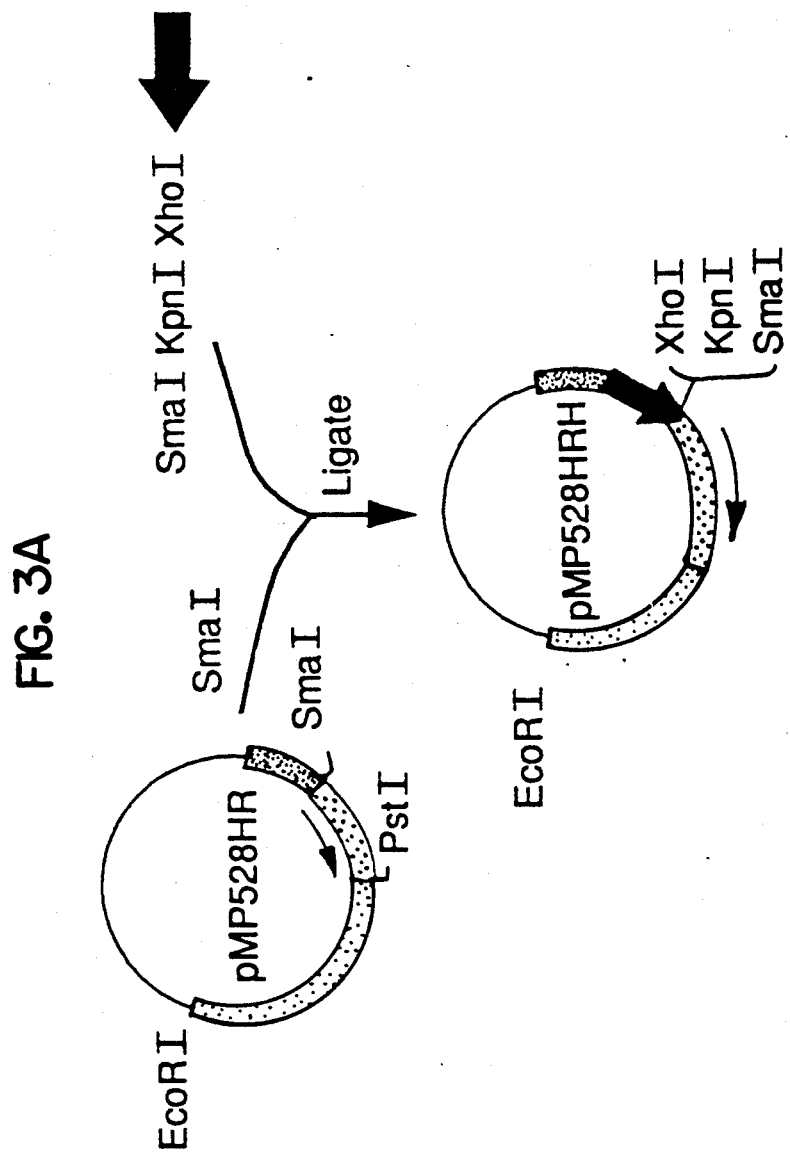
FIG. 3A schematically shows a method for the construction of plasmids pMP528HRH and pHES1-4.
Figure 4A:
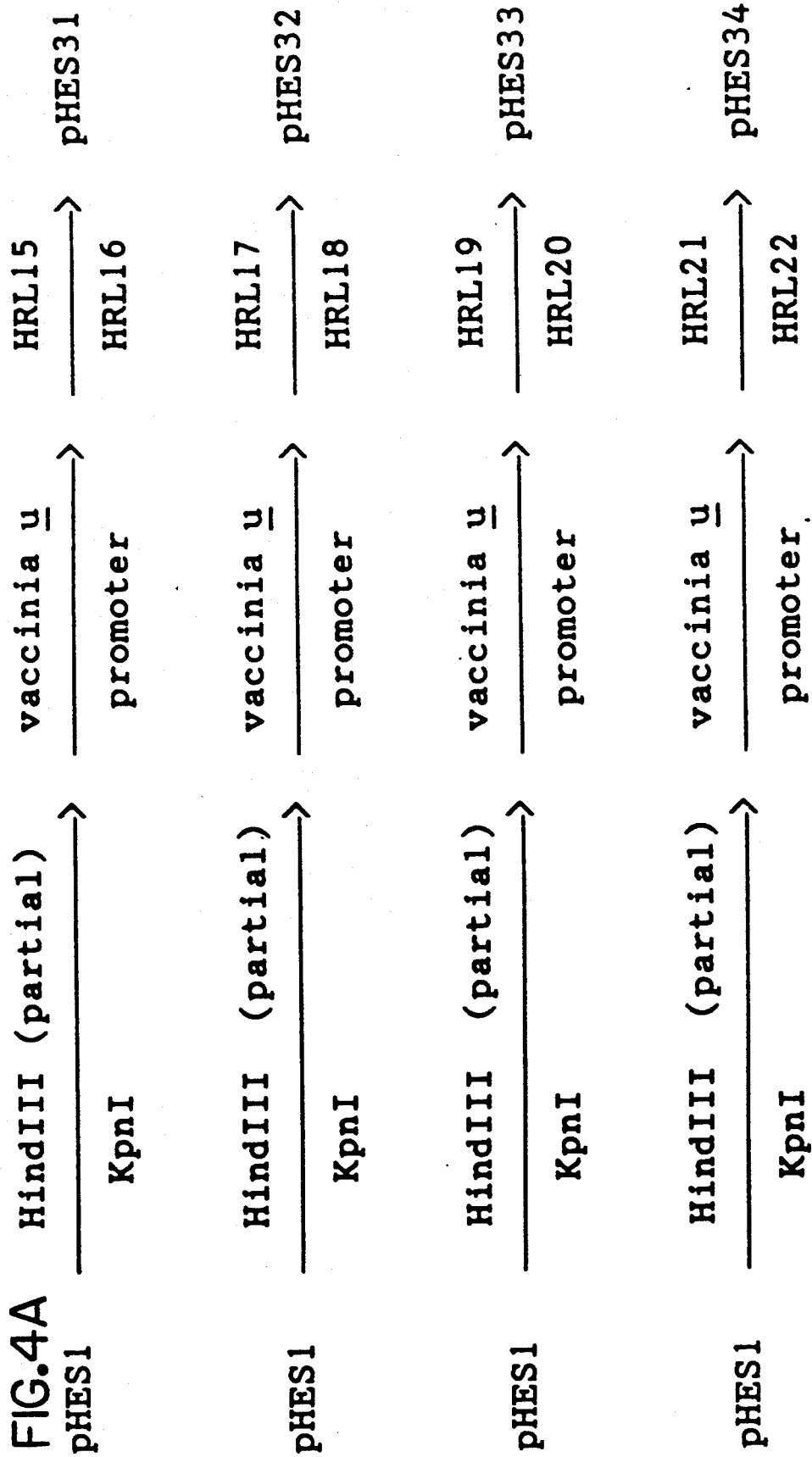
FIG. 4A schematically shows a method for the construction of plasmids pHES31-34.

The invention is directed to modified recombinant viruses having host range genes deleted therefrom so that the virus has restricted replication in the host and containing DNA which codes for and expresses a gene product in the host with restricted replication of a virus in the host. The invention is also directed to a selection system for poxvirus recombinants, particularly vaccinia recombinants, and for the cloning and expression of an open reading frame in poxvirus, particularly vaccinia virus, using a conditional lethal host range mutant of the poxvirus.

Host range mutants of rabbitpox virus (24,13) and vaccinia virus (6,7,12,17,23,36) are known.

Host range mutants of rabbitpox virus are believed to be defective in some control function required for virus replication (10). Subsequent genomic analysis of these rabbitpox virus mutants demonstrated extensive terminal deletions (up to 30 Kb) of DNA (19,25).

Nitrous acid mutagenesis of the Copenhagen strain of vaccinia virus allowed Drillien et al. (6) to isolate a host range mutant defective in replication in most human cells. Genomic analysis of this mutant revealed an extensive deletion of approximately 18 Kb toward the left terminus (6). Additional analysis by marker transfer studies mapped the genetic function responsible for host range to a 5.2 Kb EcoRI fragment (14) and finally to an 855 bp open reading frame overlapping the HindIII M/K fragments (15).

The host range gene of the WR strain of vaccinia virus (27,30) is located between 24 and 25.2 Kb from the left end of the vaccinia genome. This host range gene, transcribed leftward from HindIII K into HindIII M, is described herein as the K1L gene following the nomenclature recommended by Rosel et al. (33).

A host range gene deletion mutant of the vaccinia WR strain was generated by insertion of the neomycin resistance gene from transposon Tn5 and selection with the antibiotic G418. This deletion/recombinant, vP293, lacks approximately 21.7 Kb of DNA beginning 3.8 Kb from the left end of the genome. vP293 is capable of plaquing on primary chick embryo fibroblasts (CEF), two monkey cell lines (BSC-40 or VERO) but is defective in replication in the human cell line MRC-5.

Insertion of the host range gene, K1L, into vP293 restores the ability for growth on MRC-5 cells.

A series of plasmids were constructed which in addition to the K1L host range gene contain a vaccinia early/late promoter, H6, preferably followed by unique polylinker sequence multicloning restriction sites, translational initiation and termination codons, and an early transcription termination signal. These plasmids, pMP528HRH and pHES1-4, allow for the rapid single step, cloning and expression of any open reading frame when recombined with vP293 and scored for growth on MRC-5 cells.

Insertion of a foreign open reading frame into these plasmids followed by recombination with vP293 will simultaneously restore the host range function (K1L gene) and introduce the foreign open reading frame into the rescuing virus, vP293. The recombinant viruses are identified by their ability to plaque on MRC-5 cells.

Advantages of this system include the absence of any non-vaccinia exogenous gene in the final recombinant other than the genetic element of interest, no genetic reversion of the virus since vP293 is a deletion mutant of K1L, and the rapid one step identification of recombinants. This single step can also be used for rapid screening of expression of the foreign gene, for example, for epitope mapping.

Additional plasmids containing the K1L host range gene have been constructed where the H6 early/late promoter has been replaced with either a strictly early or a strictly late vaccinia promoter. With such additional plasmids the subtleties of temporal regulation of expression of foreign genetic elements can be studied.

The host range restricted systems of the present invention advantageously ar used in vaccines for inducing an immunological response in a host inoculated with the vaccine. In this respect, the vaccine comprises a carrier and a modified recombinant virus. The modified recombinant virus has host range genes deleted therefrom so that the virus has restricted replication in the host. In addition, the modified recombinant virus contains DNA which codes for and expresses a gene product in the host with restricted replication of a virus in the host. Modified recombinant viruses have been constructed which express gene products, particularly antigens, with restricted replication of the virus due to the deletion of the host range genes in the virus. In one embodiment, the host is a vertebrate and the antigen induces an immunological response in the vertebrate. In another embodiment, the host is a cell cultured in vitro.

One can readily appreciate that additional viruses and species beyond those cited in this application can be scored for host range restriction. Moreover, one can readily appreciate that additional "host range genes" exist in poxvirus. Furthermore, one can readily appreciate that a variety of foreign genes can be utilized in these host range mutants.

A better understanding of the present invention and of its many advantages will be had from the following examples, given by way of illustration.

In some of these examples, the WR strain of vaccinia virus was utilized. Its origin and conditions of cultivation have been previously described (27). In some of these examples, the Copenhagen strain of vaccinia virus was utilized. Its origin and conditions of cultivation have been previously described (50). Primary chick embryo fibroblasts (CEF), monkey cell lines (VERO [ATCC# CCL81] and BSC40), and the human cell line MRC-5 (ATCC# CCL171) were cultivated in Eagle's minimal essential medium (MEM) containing 5% (VERO and BSC40) or 10% (MRC-5, CEF) fetal bovine serum (FBS).

Plasmids were constructed, screened, and grown by standard procedures (22,31,32).

EXAMPLE 1

CONSTRUCTION OF PLASMID pMP528PiN AND GENERATION OF vP293

Figures 1A, 1B, 1C:
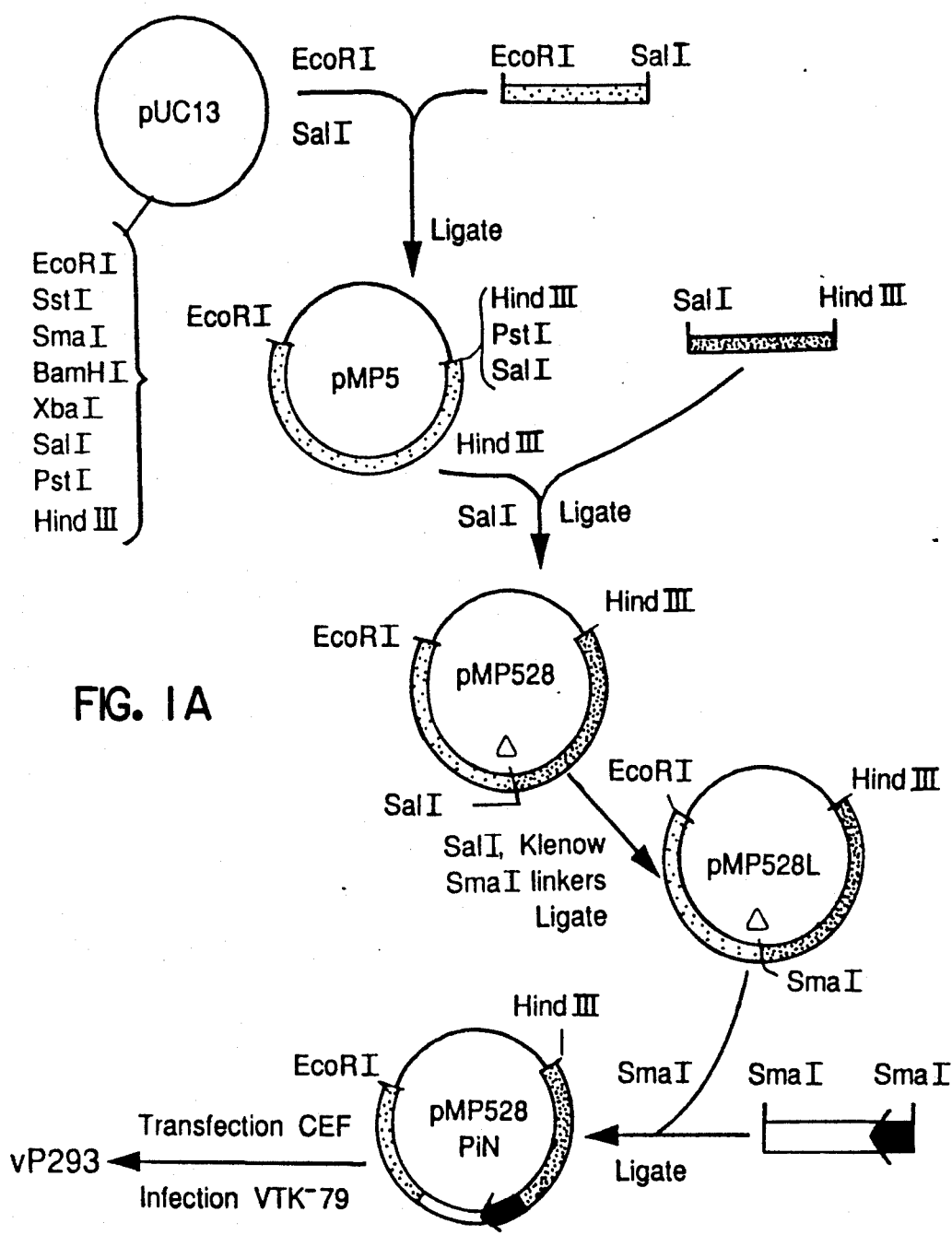
FIG. 1A schematically shows a method for the construction of the vaccinia virus deletion/recombinant vP293.
FIG. 1B is a map of the left end of the rescuing vaccinia virus VTK$^-$79 through HindIII K.
FIG. 1C is a map of the left end of the vaccinia virus deletion/recombinant vP293 through HindIII K.

Referring to FIG. 1A, an EcoRI/SalI fragment comprising the left terminal 3.8 Kb of vaccinia DNA was isolated from pAG5 (30) and inserted into pUC13 previously cut with EcoRI and SalI. The resulting plasmid, pMP5, was digested with HindIII and SalI and ligated with a 3.8 HindIII/SalI fragment containing vaccinia sequences corresponding to the right end of the vaccinia HindIII fragment K. The resulting plasmid pMP528 thus contains the 3.8 Kb of the left terminus of the vaccinia genome and 3.8 Kb from the right end of the HindIII K fragment deleting the intervening 21.7 Kb between the SalI sites at 3.8 and 25.5 Kb from the left end of the genome. The unique SalI site in pMP528 was changed to a SmaI site by addition of synthetic linkers (commercially available from Collaborative Research, Inc., Bedford, Mass.) producing pMP528L. A 1.4 Kb SmaI fragment containing the gene for neomycin phosphotransferase from transposon Tn5 (1) was isolated from pSV2-neo (35, ATCC# 37149) and put under the control of an early vaccinia promoter (designated here as Pi).

The Pi promoter, from the AvaI H region of vaccinia, has been described (37). More in particular, this promoter is derived from the AvaI H (XhoI G) fragment of the L-variant WR vaccinia strain, in which the promoter directs transcription from right to left. The map location of the promoter is approximately 1.3 Kb from the left end of AvaI H, approximately 12.5 Kb from the left end of the vaccinia genome, and about 8.5 Kb left of the HindIII C/N junction. The promoter was located by standard transcriptional mapping analysis. The Pi DNA sequence corresponds to the region upstream from an open reading frame coding for a 5kDa glycine-rich protein recently described (40). This promoter element has been shown to express foreign genes in vaccinia recombinants at early times after infection (37).

A SmaI ended Pi promoter/neo gene cassette was ligated into the SmaI site of pMP528L producing pMP528PiN. pMP528PiN contains 0.4 Kb of vaccinia sequences derived from a Sau3A subclone of AvaI H containing the Pi promoter region followed by 1 Kb of Tn5 sequences from the BglII through SmaI sites (1).

pMP528PiN was transfected into primary CEF and coinfected with the rescuing vaccinia virus, VTK⁻79, by standard procedures (28). Recombinant virus was selected and grown on primary CEF in the presence of 300 ug/ml G418 (1,11,35).

The genomic configurations of recombinant vaccinia vP293 were confirmed by Southern blot hybridization analysis. The recombinant vaccinia vP293 had been deleted of 21.7 Kb of vaccinia as predicted and contained the foreign gene encoding $neo^r$. The restriction map of the left terminus of the rescuing virus VTK⁻79 and of the recombinant virus vP293 expressing the $neo^r$ gene and selected on primary CEF in the presence of G418 are indicated in FIGS. 1B and 1C.

In the absence of the antibiotic G418, vP293 produced large plaques on primary CEF and plaqued well on BSC40 or VERO cells although vP293 plaques were detectably smaller than the parent VTK⁻79 on VERO cells. Significantly, vP293 gave no measurable replication and failed to form plaques on the human cell line MRC-5.

EXAMPLE 2

RECONSTRUCTION OF vP293 WITH THE HOST RANGE GENE, K1L

To demonstrate that the host range gene, K1L, when reconstituted into the deletion mutant vP293 of the WR strain of vaccinia would allow the virus to replicate on human cells, the host range gene, K1L, was cloned into the plasmid pMP528L and inserted into vP293.

Referring now to FIG. 2A, the vaccinia DNA sequence composing the right arm of pMP528L (FIGS. 1A and 2A) was shortened to eliminate unwanted restriction sites and to facilitate future cloning steps. pMP528L was cut by EcoRV/HindIII, blunt ended with the Klenow fragment of the *E. coli* polymerase and self ligated. In this manner, the right arm of the resulting plasmid pMP528E was reduced in length to 0.4 Kb of DNA.

An 891 bp vaccinia BglII (partial)/HpaI fragment containing the entire coding sequence and promoter from the K1L host range gene (15) was prepared from pSD452VC, a subclone of Copenhagen strain vaccinia containing sequences from HindIII M and K. The K1L containing fragment was cloned into the polylinker region of pUC8 for the sole purpose of flanking the gene with convenient restriction sites. The resulting plasmid pUC8HR was digested with HindIII and SmaI to isolate the K1L containing fragment. The HindIII end was filled in with the Klenow fragment of the E. coli DNA polymerase and the fragment cloned in the SmaI site of pMP528E. A plasmid pMP528HR with the orientation of the K1L host range gene reading leftward as shown in FIG. 2A was isolated by standard procedures.

Procedures for recombination and hybridization on nitrocellulose filters were as known in the art and as previously described (28) with the following modifications.

The donor plasmid pMP528HR was introduced by electroporation into either VERO or MRC-5 cells each coinfected with vP293. Subconfluent monolayers of VERO or MRC-5 cells were infected with rescuing virus for 1 hour. The cells were harvested with trypsin, washed with Hepes buffered saline (HeBS) (16), and electroporated in the presence of 25 ug of plasmid DNA in HeBS. Virus-infected cells were electroporated using a Bio-Rad Gene Pulser equipped with a Bio-Rad Gene Pulser Capacitance Extender. The cell suspension (0.8 ml) was placed on ice for 10 minutes in a Bio-Rad gene pulser cuvette, then pulsed at 200 volts (capacitance 960 uFD) and placed on ice for another 10 minutes. The cells were then diluted in 8 ml MEM+5% FBS, plated in 60 mm dishes containing corresponding VERO or MRC-5 cell monolayers (4 ml per dish), and incubated at 37° C. overnight.

Progeny was harvested and plated on either VERO or MRC-5 cells. The number of plaques obtained on VERO cells was 10 to 100 times greater than the number of plaques obtained on MRC-5 cells. Isolated plaques (of uniform size) were picked from MRC-5 and from VERO cell cultures (both large and small sized plaques). These plaque isolates were replated on VERO cells and after three days the resulting plaques were lifted onto nitrocellulose filter disks and prepared for in situ hybridization (26). All the plaques originating from MRC-5 cells and all the larger plaques but not the smaller sized plaques derived from VERO cells gave positive hybridization signals when probed with a $^{32}P$ labeled probe to the K1L coding sequences. This data is consistent with restoration of host range functions contained in the K1L coding sequence.

An isolate obtained from MRC-5 cells was further purified and designated vP457. In vP457 the K1L gene had been restored and was situated within the deletion in its native orientation reading from right to left. The K1L sequences had replaced the Pi promoter/neomycin phosphotransferase gene cassette present in vP293 as shown in FIGS. 2B and 2C. Compared to the genome of the L variant vaccinia (30,27) vP457 contains a 291 bp deletion to the right of the K1L gene and a 20.2 Kb deletion to the left of the K1L gene.

EXAMPLE 3

CONSTRUCTION OF PLASMIDS pMP528HRH AND pHE81-4

To demonstrate that the conditional lethal mutation in vP293 could be exploited for constructing donor plasmids into which additional open reading frames could be cloned, a series of plasmids, pMP528HRH and pHES1-4, were constructed. Recombination of exogenous open reading frames present in a plasmid containing the K1L host range gene into vP293 would yield a simple method for generating vaccinia recombinants by virtue of host range restriction.

A vaccinia promoter, H6, was added upstream from the K1L gene in pMP528HR. This early/late promoter was previously identified by standard transcriptional mapping and DNA sequence analysis. It has the sequence (positions −125 to +3) ATTCTTTATT-CTATACTTAAAAAAT-GAAAATAAATACAAAGGTTCTT-GAGGGTTGTGTTAAATTG AAAGC-GAGAAATAATCATAAATTATTTCATTATCG-CGATATCCGTTAAGTTTGTATCGTAATG. The sequence is that described as being upstream of open reading frame H6 by Rosel et al. (33).

Referring now to FIG. 3, DNA corresponding to positions −124 to −1 (with position −102 changed from A to G in order to prevent the introduction of any potential initiation codons) and followed by XhoI, KpnI, and SmaI restriction sites was synthesized chemically (FIG. 3B) and cloned into the SmaI site of pMP528HR producing pMP528HRH (FIG. 3A). Thus, pMP528HRH contains the H6 promoter upstream from the K1L gene which is expressed under the control of the K1L endogenous promoter. Both are in a right to left orientation with respect to vaccinia arms (genome). The H6 promoter in pMP528HRH is immediately upstream of unique XhoI, KpnI, and SmaI restriction sites.

To increase further the utility of the system a series of plasmids pHES1-4 were derived from pMP528HRH. pHES1 was constructed by the following procedure: pMP525HRH was cut with XhoI and XmaI, and the oligonucleotides HRL1 5'(TCGACCATG-GGATCCCCGGGTACCGAGCTCTCGAG-TAAATAAATAATTTTTAT)3' and HRL2 5'(CCGGATAAAAATTATTTATTTACT-CGAGAGCTCGGTACCCGGGGATC-CCATGG)3' cloned into this site. pHES2, pHES3 and pHES4 were similarly constructed. pHES2 was constructed with the oligonucleotides HRL3 5'(TCGAC-CATGGGGATCCCCGGGTACCGAGCTCT-CGAGTAAATAAATAATTTTTAT)3' and HRL4 5'(CCGGATAAAAATTATTTATTTACT-CGAGAGCTCGGTACCCGGGGATCC-CCATGG)3', pHES3 was constructed with the oligonucleotides HRL5 5'(TCGACCATGGG-GGATCCCCGGGTACCGAGCTCTCGAG-TAAATAAATAATTTTTAT)3' and HRL6 5'(CCGGATAAAAATTATTTATTTACT-CGAGAGCTCGGTACCCGGGGATCCC-CCATGG)3' and pHES4 was constructed with the oligonucleotides HRL7 5'(TCGAGGATCCCGG-GTACCGAGCTCTAAATAAATAATTTTTAT)3' and HRL8 5'(CCGGATAAAAATTATTTATT-TAGAGCTCGGTACCCGGGATCC)3'.

The pertinent DNA sequence elements, restriction sites, and transcriptional and translational signals of pMP528HRH and pHES1-4 are as follows.

The sequence of the synthetic H6 promoter (positions −124 through −1, with the altered base at position −102 underlined) and downstream restriction sites present in pMP528HRH are shown in FIG. 3B.

The bracketed sequence is replaced in plasmids pHES1-4, with restriction sites, stop codons, and early transcriptional termination signal as indicated, as shown in FIG. 3C for pHES1, in FIG. 3D for pHES2, in FIG. 3E for pHES3, and in FIG. 3F for pHES4.

In addition to the elements contained in pMP528HRH, each plasmid, pHES1-3, contains a translation initiation codon downstream from the H6 promoter followed by unique multiple restriction sites, translational termination signal sequences, and a specific vaccinia early transcription termination signal sequence (39). Each plasmid, pHES1-3, contains a translation initiation codon in one of the three reading frames. Therefore any DNA sequence which contains an open reading frame can be expressed when cloned into one of these plasmids and recombined into vaccinia virus.

The fourth plasmid, pHES4, does not contain a translation initiation codon but does contain unique multiple restriction sites, translational termination sequences, and an early transcription termination signal sequence. A DNA sequence which contains an open reading frame and an initiation codon can be expressed when cloned into pHES4 and recombined into vaccinia virus.

EXAMPLE 4

INCORPORATION OF THE BACTERIAL LACZ GENE INTO VACCINIA VIRUS AND SELECTION OF THE RECOMBINANT VIRUSES ON THE BASIS OF HOST RANGE RESTRICTION

To demonstrate the utility of the pHES1-4/VP293 host range selection system, a recombinant vaccinia virus containing the *E. coli* lacZ gene encoding B galactosidase was constructed.

A BamHI fragment containing codons 8 through the end of the lacZ gene was obtained from pMC1871(34).

This lacZ BamHI fragment was cloned into the unique BamHI site of the plasmids pHES1-4.

Recombination between the resulting plasmids pHESLZ1-4 transfected individually into VERO cells coinfected with the host range mutant vP293 was performed.

After 24 hours post infection, progeny virus was harvested by three freeze/thaw cycles and plated on either VERO (Table 1A) or MRC-5 (Table 1B and 1C) cells.

VERO and MRC-5 monolayers (Table 1A and 1B), stained with neutral red, were lifted after 3 days onto nitrocellulose filters and prepared for in situ hybridization (26) using a $^{32}P$ labeled lacZ gene probe. VERO (data not shown) and MRC-5 monolayers (Table 1C) were exposed to X-gal (5-bromo-4-chloro-3-indolyl-B-D-galactopyranocide, Boehringer Mannheim) and blue color development scored after 8 hours.

When progeny was plated on VERO cells and expression of B galactosidase assayed in the presence of X-gal no blue plaques were observed in cells transfected with pHESLZ1, 2 or 4. Significantly, approximately 20% of the plaques generated with plasmid pHESLZ3 gave blue plaques in the presence of X-gal (data not shown).

When progeny was plated on VERO cells and recombinant viruses screened by in situ hybridization, 12 to 22% of the plaques gave positive hybridization signals to lacZ (Table 1A). When analyzed by in situ DNA hybridization (26) every plaque on MRC-5 demonstrated the presence of the lacZ gene (Table 1B). B galactosidase activity, however, was seen only in those plaques on MRC-5 which were derived from pHESLZ3 (Table 1C). Only the plasmid construct pHESLZ3 had the lacZ gene in frame with the translational initiation codon.

toic membrane (CAM) has been reported (43). This gene, u, is highly expressed at early times post infection. The u gene maps to a 1465 bp NcoI-HaeIII fragment.

The region of the Copenhagen strain vaccinia virus genome containing the equivalent of the cowpox u gene was determined by Southern blot analysis (44) using cloned cowpox DNA as a probe. The Copenhagen equivalent of the cowpox u gene maps to HindIII B, and corresponds to the location of the u gene in WR strain vaccinia virus recently reported (45).

In cowpox, the u promoter region is located downstream from an NcoI site at −294 (43). DNA containing the Copenhagen u gene equivalent and promoter was sequenced (46). The Copenhagen u gene equivalent is nonfunctional, resulting in white pock formation for Copenhagen vaccinia virus grown on CAM due to frameshift mutations within the coding region. The upstream region is highly homologous to the cowpox promoter region and functional. Recombinant vaccinia containing *E. coli* beta-galactosidase expressed under the control of the Copenhagen vaccinia u promoter form blue plaques in the presence of the chromogenic substrate X-gal. As in cowpox, the Copenhagen genome contains the NcoI site upstream from the u promoter region.

To move the Copenhagen u promoter region to the pHES system, a HindIII site was added to the NcoI site upstream from the u promoter by ligation with self annealed oligonucleotide HRL14 (5' CATGGAAGCTTC 3'; HindIII site underlined). A 299 bp HindIII-ClaI fragment containing the u promoter region from the NcoI site through the ClaI site at −6 was isolated. The H6 promoter was removed from pHES1 (Example 3) by partial HindIII digestion, followed by digestion with KonI. Referring now to FIG. 4, the 7.8 kb HindIII-KpnI vector fragment was isolated from an

TABLE 1

Analysis of recombinant lacZ/vaccinia virus generated with plasmids pHESLZ1-4 and vP293 vaccinia virus

| | Donor Plasmid | | | |
|---|---|---|---|---|
| | pHESLZ1 | pHESLZ2 | pHESLZ3 | pHESLZ4 |
| A. Total Plaques | 1056 | 637 | 793 | 1344 |
| Hybridization Positive | 153 | 141 | 95 | 269 |
| Percent Positive | 14.5 | 22 | 12 | 20 |
| B. Total Plaques | 60 | 56 | ND | 71 |
| Hybridization Positive | 60 | 56 | ND | 71 |
| Percent Positive | 100 | 100 | | 100 |
| C. Total Plaques | 60 | 55 | 59 | 70 |
| X-gal Positive | 0 | 0 | 59 | 0 |
| Percent Positive | 0 | 0 | 100 | 0 |

EXAMPLE 5

CONSTRUCTION OF PLASMIDS pHES31-34 AND pHES61-64

To demonstrate that the conditional lethal mutation of vP293 could be exploited for constructing further donor plasmids, and to extend the vaccinia WR vP293-based host range selection system, the pHES plasmid series (Example 3) was expanded by replacing the H6 early/late vaccinia promoter with other temporally regulated promoters. Plasmids pHES31-34 and plasmid series pHES61-64 were generated to regulate expression of foreign genes early or late, respectively.

The localization and sequence of the gene for a 38 kDa protein in cowpox virus required for (hemorrhagic) red pock formation on the chicken chorioallanagarose gel (FIG. 4A). To replace promoter sequences downstream from the ClaI site and polylinker sequences through the KpnI site, eight oligonucleotides, HRL15 through HRL22, were synthesized (FIG. 4B). Pairs of oligonucleotides were annealed and ligated with the 7.8 kb HindIII-KpnI vector fragment from pHES1 and the HindIII-ClaI u promoter fragment generating plasmids pHES31-34 (FIG. 4A).

Referring now to FIG. 5, the resulting plasmids, pHES31 through pHES34, contain polylinker regions downstream from the Copenhagen u promoter region (FIG. 5). The 0.3 kb DNA sequence specifying the u promoter is indicated in FIG. 5 for plasmid pHES31 only. The identical sequence is present in plasmids pHES32 through pHES34. The bracketed sequence following the promoter region in pHES31 is replaced by the bracketed sequences indicated for pHES32 through pHES34. Restriction sites are indicated. In pHES31 through pHES33, the polylinker region is located downstream from the initiating ATG in the three different reading frames. Plasmid pHES34 does not contain an initiating ATG. In all members of the pHES31 through pHES34 series, the polylinker region is followed by translational stop codons in all three reading frames, underlined, followed by the sequence TTTTTAT, overlined, which has been shown to specify transcriptional termination for early genes in vaccinia (39).

As with the pHES1 through pHES4 series of plasmids (Example 3) the pHES31 through pHES34 series allows expression of foreign coding sequences inserted into the polylinker region. Foreign coding sequences containing an initiation codon are expressed under the control of the vaccinia u promoter by insertion into pHES34. Foreign coding sequences devoid of an initiation codon are expressed in the appropriate reading frame by insertion into pHES31, pHES32 or pHES33. As with the original pHES series, pHES31 through pHES34 contain the K1L human host range gene (15). Recombination between vaccinia deletion mutant vP293 (Example 1) and all plasmid derivatives of the pHES series generate recombinant vaccinia virus which are selected by their ability to grow on human cells.

To further adapt the pHES plasmid system to allow expression of foreign genes in recombinant vaccinia at late times post infection, the promoter for the 160 kDa ATI gene of cowpox was chosen (47). The 533 bp region immediately upstream from the cowpox ATI gene, when inserted into vaccinia virus, has been shown to direct high levels of expression of foreign genes at late times after infection (48). The 63 bp cowpox DNA region extending from the upstream BglII site to the initiation codon is sufficient to act as a promoter for the expression of foreign genes in vaccinia. DNA specifying this promoter region was synthesized and inserted into the pHES system as detailed below.

Figure 6A:
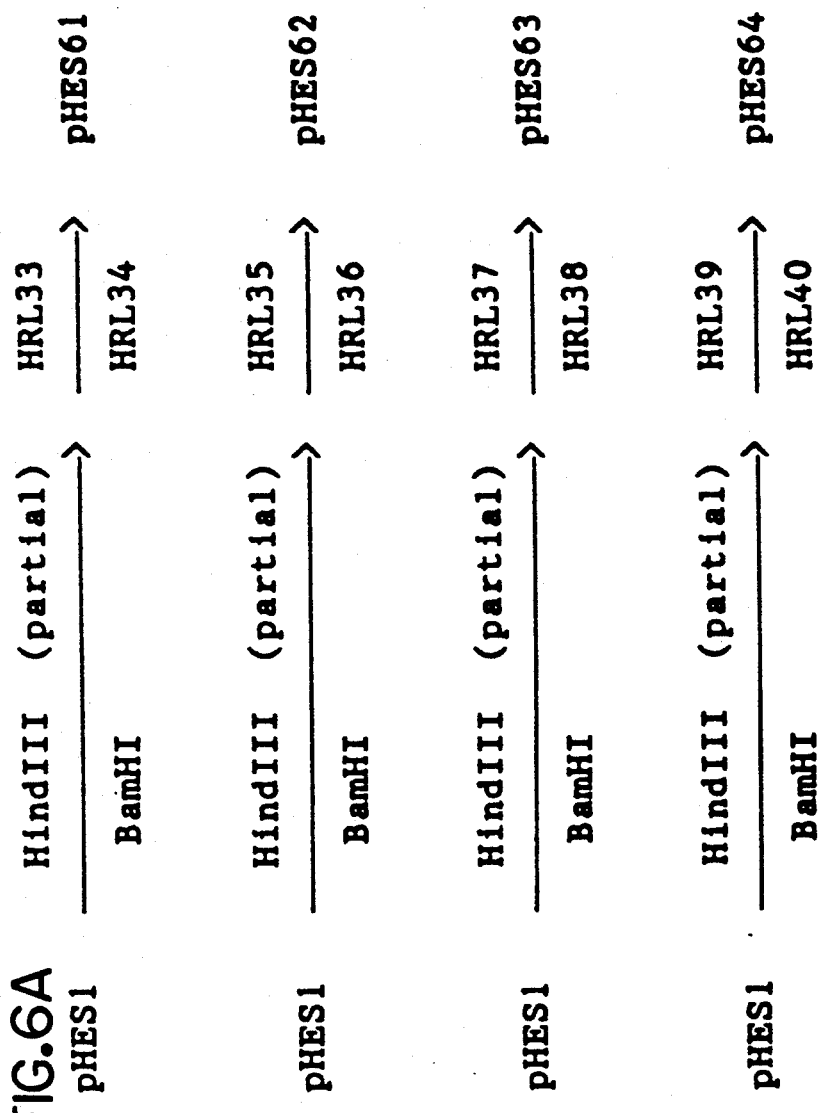
FIG. 6A schematically shows a method for the construction of plasmids pHES61-64.

The H6 promoter was removed from pHES1 (Example 3) by partial HindIII digestion, followed by digestion with BamHI. Referring now to FIG. 6, the 7.8 kb HindIII-BamHI vector fragment was isolated from an agarose gel (FIG. 6A). To replace H6 promoter sequences with cowpox ATI promoter sequences and BamHI linkage to polylinker sequences, eight oligonucleotides, HRL33 through HRL40, were synthesized (FIG. 6B). Pairs of oligonucleotides were annealed and ligated with the 7.8 kb HindIII-BamHI vector fragment from pHES1 generating plasmids pHES61-64. Each annealed pair of oligonucleotides contains the 63 bp synthetic cowpox ATI promoter region flanked by HindIII and BamHI restriction sites as indicated.

Referring now to FIG. 7, the resulting plasmids, pHES61 through pHES64, contain polylinker regions downstream from the cowpox ATI late promoter region (FIG. 7). The identical sequence for the cowpox ATI promoter, which is present in pHES61 through pHES64, is indicated here for pHES61 only. The bracketed sequence following the promoter region in pHES61 is replaced by the bracketed sequences indicated for pHES62 through pHES64. Restriction sites are indicated. In pHES61 through pHES63, the polylinker region is located downstream from the ATG initiation codon in the three different reading frames. Plasmid pHES64 does not contain an ATG initiation codon.

As in the pHES plasmid series containing other promoters, all members of the pHES61 through pHES64 plasmid series contain polylinker regions followed by translational (underlined) and transcriptional termination signals (overlined). Since derivatives of the pHES61 through 64 series contain the vaccinia K1L human host range gene, recombinant vaccinia progeny virus generated by recombination of these plasmids with vP293 are selected by their ability to grow on human cells.

EXAMPLE 6

CONSTRUCTION OF RECOMBINANTS vP548 AND vP661

The sequence of 15,537 bp of DNA located near the left end of the Copenhagen genome is shown from left to right in FIG. 8. The sequence includes 7218 bp between the rightmost SalI site in HindIII C and the HindIII C/N junction, and extends through the entire sequences for HindIII N (1544 bp; positions 7219-8762), HindIII M (2219 bp; positions 8763-10981) and HinDIII K (4551 bp; positions 10982-15532). For clarity, coding sequences and restriction sites are designated by base positions as indicated in FIG. 8. By conventional nomenclature, vaccinia open reading frames (ORFs) are designated by numbering from left to right within each HindIII fragment (33). Since different vaccinia strains contain significant differences toward the left end of HindIII C (the left terminus of the vaccinia genome), ORFs located within the vaccinia HindIII C fragment are designated herein by numbering from right to left starting at the HindIII C/N junction. By this nomenclature, ORF C1L is the rightmost ORF beginning in the HindIII C fragment of Copenhagen vaccinia DNA (see FIG. 8).

Figures 1, 9:
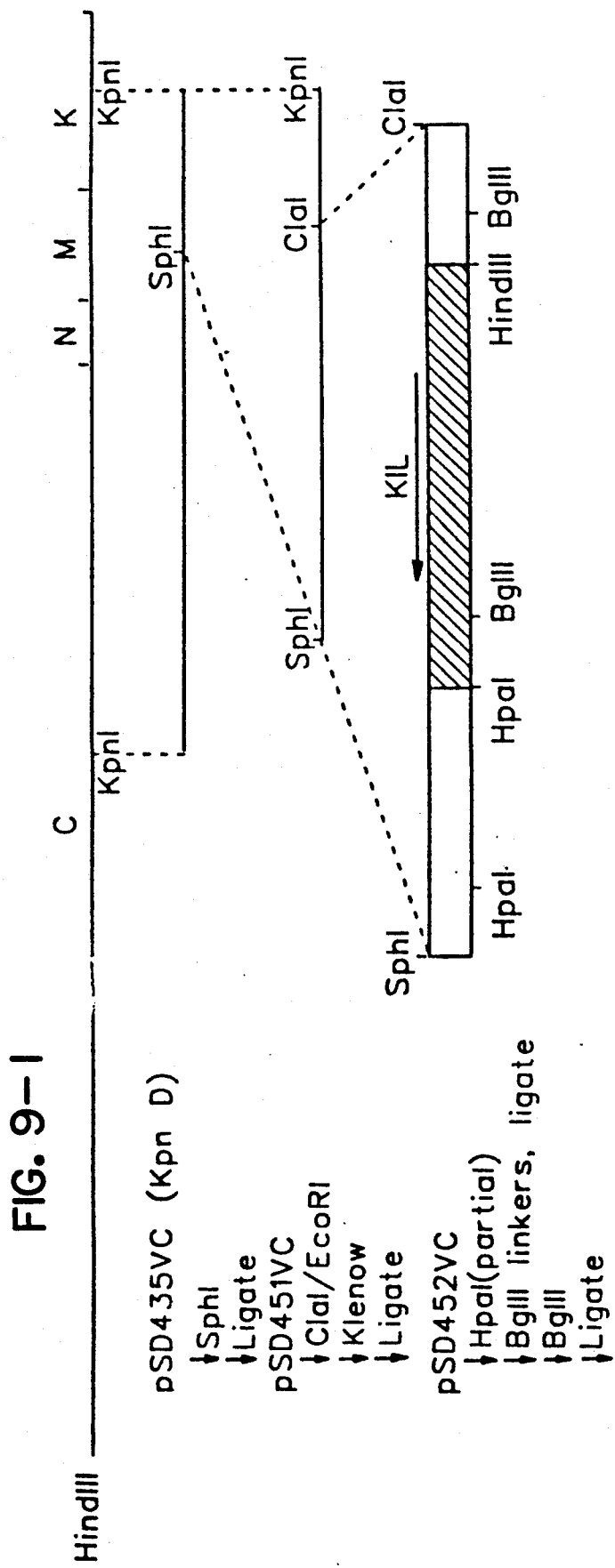
FIGS. 9-1 and 9-2 schematically show a method for the construction of recombinants vP548 and vP661.
Figures 2, 9:
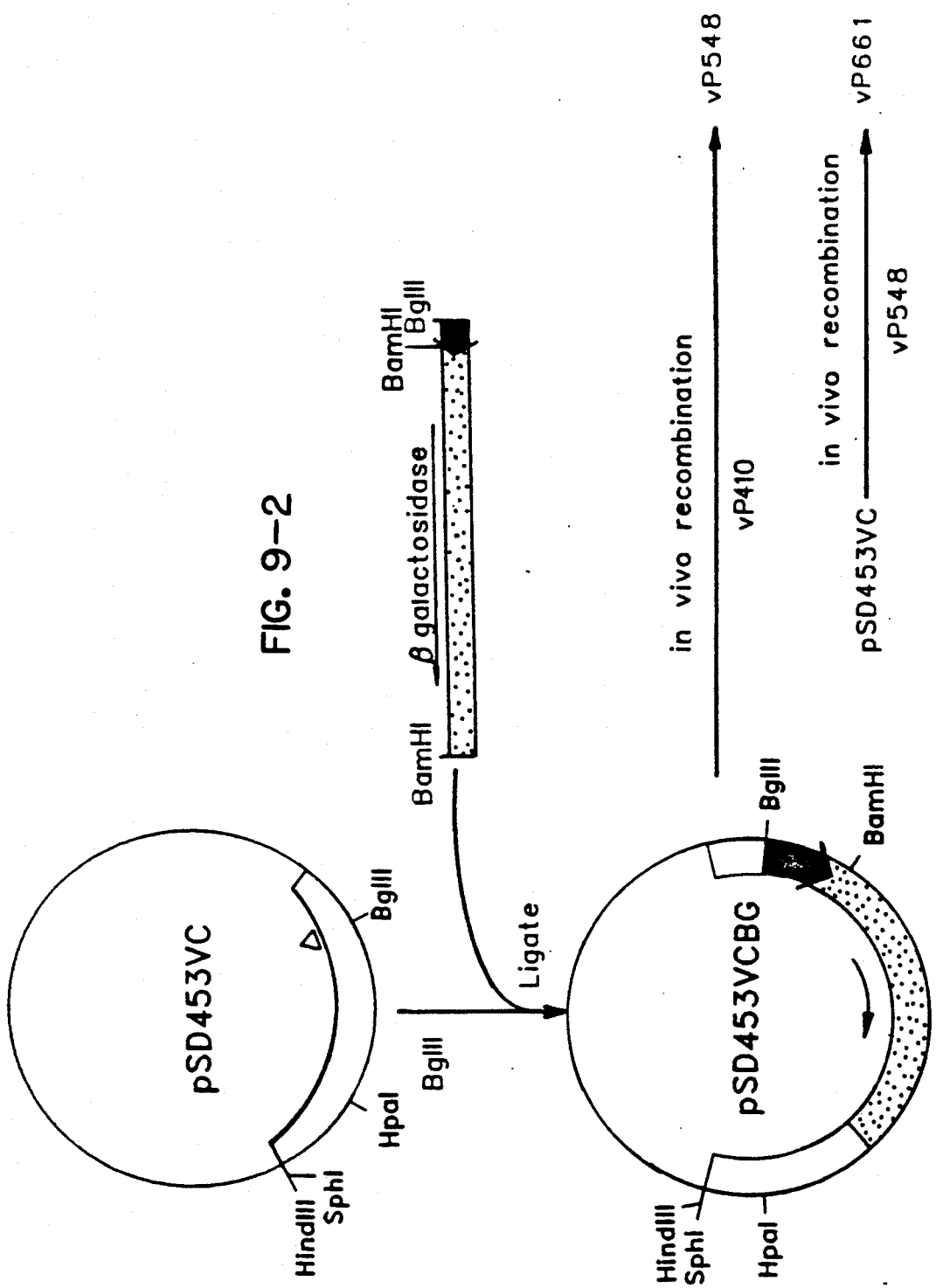
Figure 10:
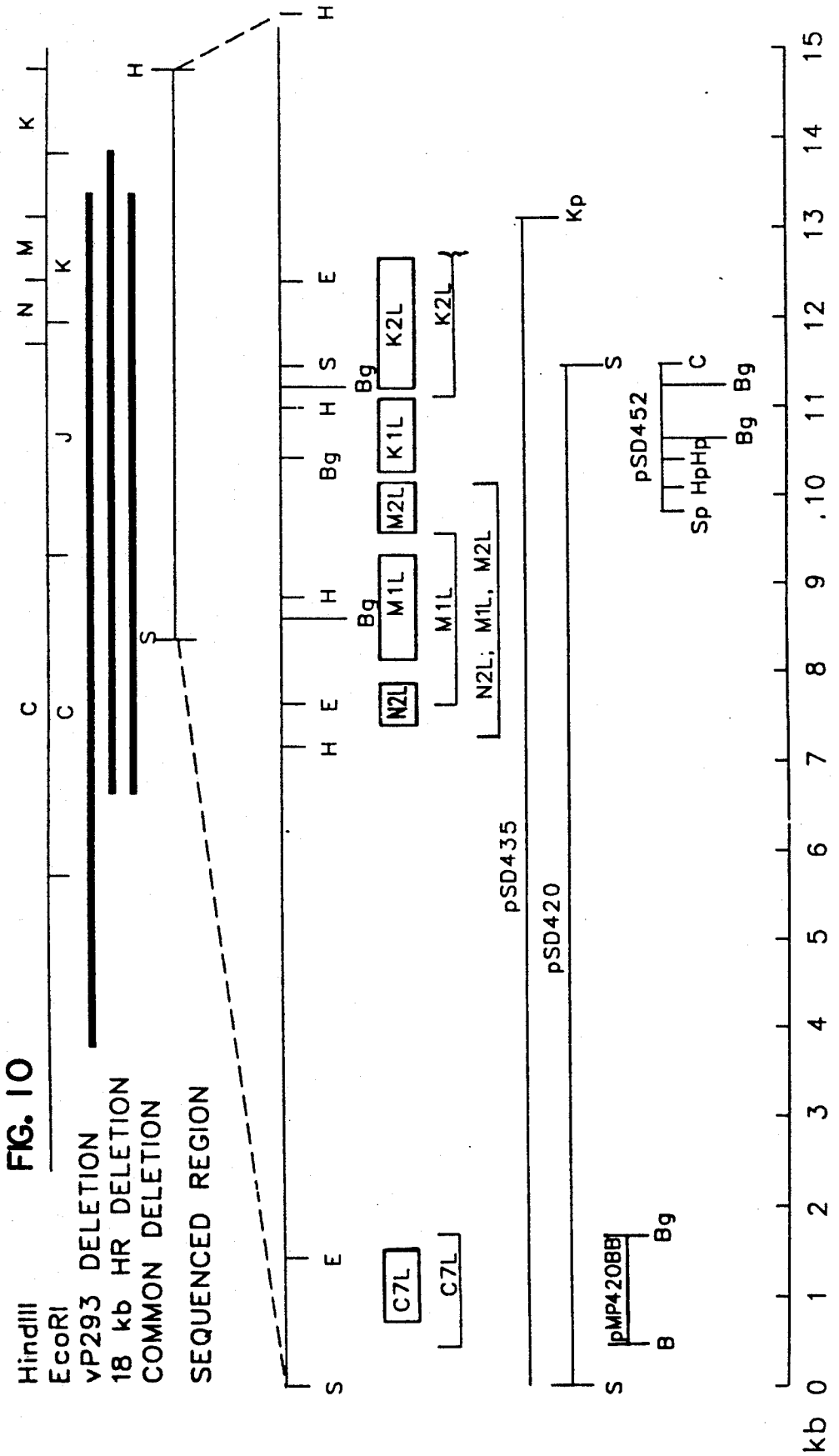
FIG. 10 is a map of the left end of the vaccinia virus genome.

Referring now to FIG. 9, plasmids were constructed to delete the K1L human host range gene (15) from Copenhagen virus in the expectation that removal of the K1L gene would result in loss of the ability of the resultant virus to replicate on human cells. Copenhagen KonI fragment D, which includes approximately 2.5 kb of DNA to the left of the sequence presented in FIG. 8 and extends rightward through position 12998, was cloned into the KonI site of pUC18, resulting in pSD435 (FIG. 9). (Note: in FIG. 9 plasmids in the pSD series containing vaccinia Copenhagen inserts appear with the optional "VC" designation. Thus, pSD435 is equivalent to pSD435VC. The "VC" designation is omitted in FIG. 10.) The Kpn D fragment contains the K1L gene (pos. 11030-10179). For ease of manipulation of the K1L gene and its flanking region, pSD452, a subclone of pSD435 which includes sequences between the SohI site (pos. 9478) in HindIII and the ClaI site in HindIII K (pos. 11731) was constructed (FIG. 9). The K1L gene is indicated by a striped block, direction of transcription indicated by an arrow. pSD452, which contains two HpaI sites (pos. 9561, 10155) was linearized by partial digestion with HpaI and BglII linkers were ligated into the HpaI site (pos. 10155) immediately downstream from the K1L gene. The resulting plasmid was cut with BglII and self-ligated, generating pSD453. In pSD453, the K1L gene and its promoter are deleted. The site of deletion is indicated by a triangle (FIG. 9).

A fragment containing the coding sequences of beta-galactosidase (stippled block, direction of gene indicated by an arrow) under the control of the vaccinia 11 kDa late promoter (dark arrow) (49) was inserted into the BglII site of pSD453, generating pSD453BG (FIG. 9). pSD453BG was used as donor plasmid for recombination with vP410, a thymidine kinase minus derivative of Copenhagen strain vaccinia virus (50). Progeny virus were assayed in the presence of X-gal. Blue plaques were picked and purified by growth on VERO cells. As expected, the resulting recombinant, vP548, was shown to be missing the K1L gene when probed with $^{32}$P-labelled K1L sequences. Surprisingly, vP548 plaqued on MRC-5 cells.

To test whether the presence of the gene for B-galactosidase in vP548 was instrumental in its ability to plaque on MRC-5 cells, the 11 kDa/B-galactosidase cassette was removed from vP548 by recombination with donor plasmid pSD453. The resulting vaccinia deletion recombinant, vP661, also plaqued on MRC-5 cells.

EXAMPLE 7

IDENTIFICATION OF THE C7L HOST RANGE GENE FROM COPENHAGEN STRAIN OF VACCINIA VIRUS

The results described in Example 6 suggest that K1L is not the only vaccinia host range gene capable of conferring growth on human cells. The possibility was investigated that the deleted regions of vaccinia virus vP293 (Example 3) and the host range 18kb deletion mutant vaccinia virus (14) were deleted for another gene which like K1L confers the ability to grow on human cells. FIG. 10 presents the restriction map of the left end of the vaccinia virus genome showing locations of potential host range genes. The HindIII and EcoRI maps of the left end of the vaccinia virus genome are shown at the top. Only the relevant EcoRI sites are indicated. The extent of the host range deletions in vaccinia virus deletion mutants vP293 (Example 3) and the 18 kb host range deletion (14), as well as the deleted region common to both deletion mutants are shown by heavy lines. The 15537 bp sequenced region (FIG. 8) from the rightmost SalI site through the HindIII K fragment is expanded. Only the relevant restriction sites are indicated. The locations of genes discussed here are indicated within open boxes. The locations of fragments used to test genes for host range capability are indicated above troughs. The locations of vaccinia inserts in plasmids described herein, along with relevant restriction sites, are also indicated. Code: S =SalI; E =EcoRI; H=HindIII; Bg=BglII; Kp=KpnI; B=BamHI; Sp=SphI; C=ClaI; Hp=HpaI.

As indicated in FIG. 10, the deletion region common to the 18 kb host range deletion and the deletion in vP293 extends from an undetermined point in EcoRI C to the SalI site n HindIII K (pos. 11412). It has been determined that a host range function mapped to the EcoRI K (pos. 7550–12875) fragment (14) and a host range gene, K1L (positions 11030–10179), has been identified in a 846 bp BglII D fragment (pos. 10271–11116) from within EcoRI K (15). The BglII A fragment (pos. 8645–10270) from EcoRI K did not restore growth on human cells. However, in these analyses possible host range genes in the EcoRI K fragment which are situated between the EcoRI (pos. 7749) and BglII (pos. 8644) sites, or between the BglII (pos. 11116) and ClaI (pos. 11731) sites, would have been missed. Also, genes which cross the EcoRI (pos. 7749), BglII (pos. 8644) or ClaI (pos. 11731) sites of EcoRI K, or the EcoRI junction (pos. 1295) between EcoRI C and J would have been missed.

Analysis of the amino acid translation of the 15.5 kb sequence described herein reveals four potential genes which would not have been tested earlier (14,15). All four open reading frames are oriented right to left. The positions of these four ORFs, C7L (pos. 1314–863), N2L (pos. 7943–7416), M1L (pos. 9329–7985) and K2L (pos. 12367–11258) are indicated in FIG. 0. The first ATG in the M1L ORF is located at position 9403. Since this location is upstream from (to the right of) the published locations for transcriptional start sites for M1L (51) and within coding sequences for the M2L gene, one can interpret the ATG at position 9329 as the true translational start of the M1L gene.

Of the four potential genes, M1L initially seemed the most likely candidate as a host range gene. $^{32}P$-labelled DNA probe for K1L cross reacts weakly with M1L sequences on a Southern blot (44) (data not shown).

The M1L gene sequence in Copenhagen strain of vaccinia described herein differs at the amino terminus from the published M1L sequence in WR strain of vaccinia (51). Insertion of two bases (pos. 9307, 9312) in the present sequence relative to the published sequence result in frame shift mutations. In the sequence described herein, translation begins at the ATG at pos. 9329. In the reported sequence (51) potential translation from this ATG would be terminated by an in frame stop codon at pos. 9278 and translation of M1L would begin at pos. 9247. In the sequence described herein, translation from pos. 9329 is continuous to the stop codon of M1L previously reported (pos. 7987). The net result is that the M1L gene described herein contains 27 extra amino acids at the amino terminus as well as two amino acid substitutions relative to the reported M1L gene (51). The sequence for the WR N2L gene has also been published (51). The Copenhagen N2L gene described herein has four amino acid substitutions relative to the published sequence.

Computer analysis of the protein encoded by the Copenhagen vaccinia virus M1L ORF described herein reveals a higher level of similarity to the Copenhagen vaccinia virus K1L protein (15) than to any other protein in the PIR or Swiss-Prot data bases (data not shown). This data, coupled to the data derived by Southern blot analysis, suggests that the M1L gene product might serve a similar host range function as the K1L gene product.

Therefore, of the four potential human host range genes, the M1L gene was tested first in the vaccinia virus vP293 host range selection system to assay for its ability to allow growth of vaccinia virus on human cells. To recombine the gene for M1L and subsequent genes into the vP293 selection system, pMP528 (Example 1) and its derivative pMP528E (Example 2) were utilized as vector plasmids. pMP528 is the original vaccinia deletion plasmid from which vaccinia recombinant vP293 was derived. pMP528 contains a SalI site at the deletion junction between vaccinia flanking arms derived from vaccinia DNA regions HindIII C/HindIII K. In pMP528E the right flanking arm derived from vaccinia HindIII K DNA has been shortened, and a SmaI site has been substituted for the original SalI site at the HindIII C/HindIII K deletion junction.

Testing of potential vaccinia host range genes in the vP293 system is presented schematically in FIG. 11. The HindIII map of the left end of the vaccinia virus genome is given on the top line. Locations of genes are indicated within boxes, direction of transcription indicated by arrows. Location of vaccinia fragments used to test host range activity of genes are indicated by troughs.

Figure 11:
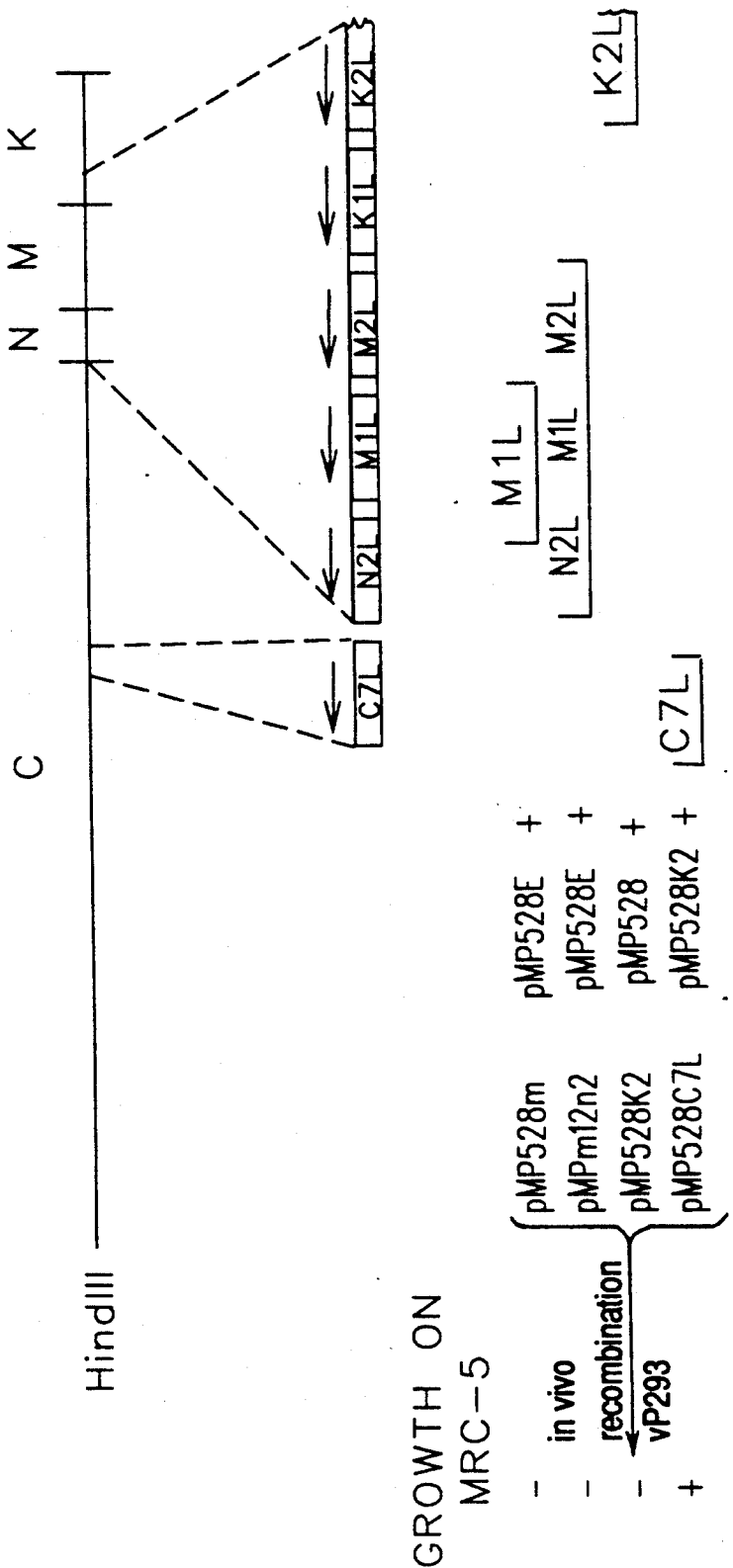
FIG. 11 schematically shows a method for the testing of potential vaccinia host range genes in the vP293 system.
Figure 12:
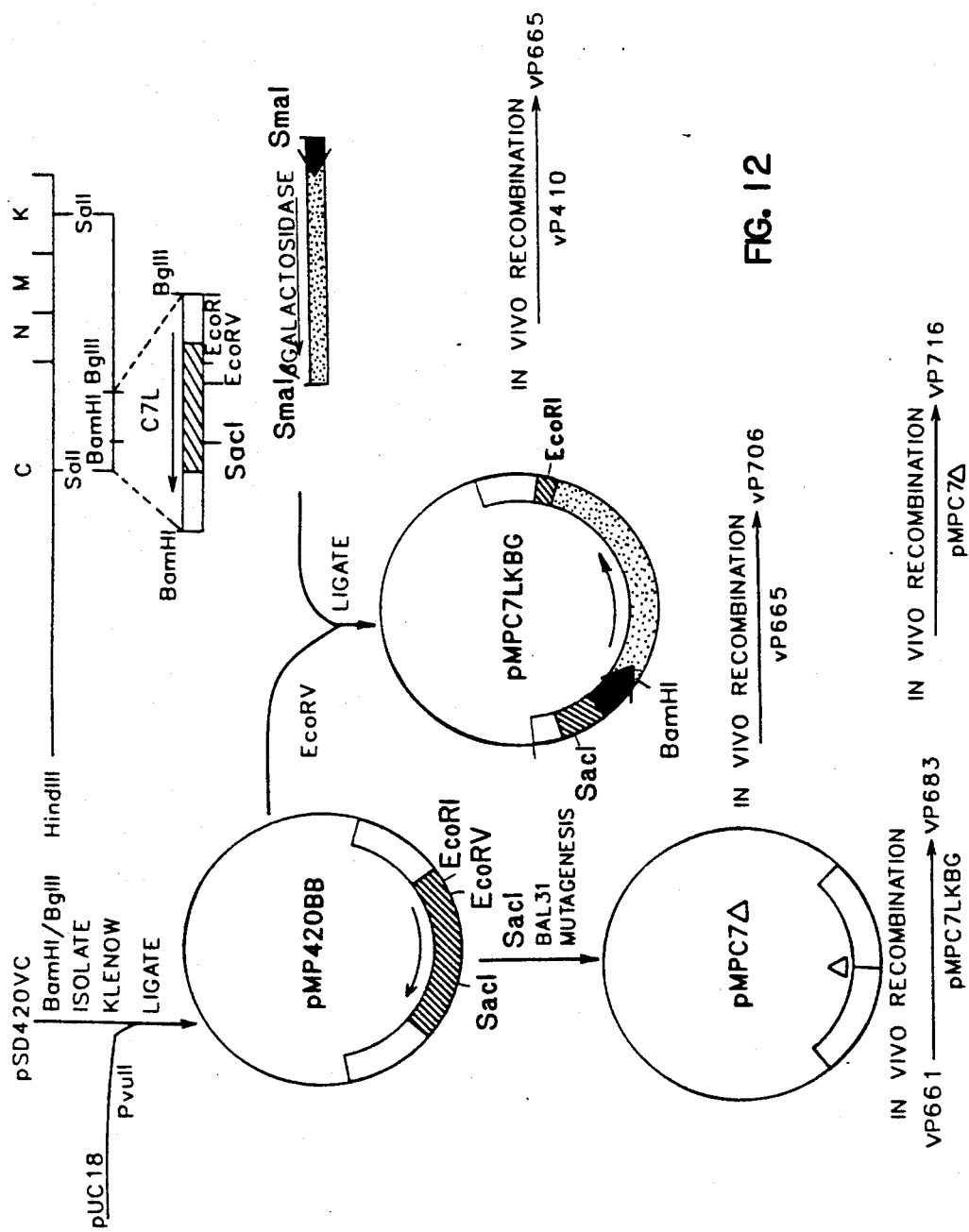
FIG. 12 schematically shows a method for the construction of recombinants vP665, vP683, vP706 and vP716.

A DNA fragment extending from the 3' end of M2L (pos. 9384, 55 bases upstream from the M1L initiation codon) through the ScaI site (pos. 7906) downstream from M1L was ligated into pMP528E cut with SmaI (FIG. 11). The resulting plasmid, pMP528m, was used as donor plasmid for recombination with vaccinia virus vP293. Although analysis with $^{32}$P-labelled DNA probe for the M1L gene revealed that M1L sequences were inserted into vaccinia, progeny virus does not plaque on MRC-5 cells.

Since the size of the promoter region necessary for initiation of transcription of the M1L gene is unknown, it is possible that the 55 bases upstream from M1L coding sequences in plasmid pMP528M were not sufficient to specify transcription of the M1L gene. Therefore, a larger fragment of Copenhagen strain vaccinia virus DNA containing the entire genes for M2L, M1L and N2L was tested. A 2849 bp HpaI fragment (pos. 7307-10155) was obtained by partial HpaI digestion of pSD420, a SalI clone of Copenhagen vaccinia virus DNA (pos. 1-10477). This HpaI fragment contains the entire genes for M2L (pos. 10043-9381), M1L (pos. 9329-7985) and N2L (pos. 7943-7416). The HpaI fragment was cloned into pMP528E cut with SmaI (FIG. 11). The resulting plasmid, designated pMPm12n2 in FIG. 3, was used as donor plasmid for recombination with vP293. Although analysis with $^{32}$P-labelled DNA probes indicated that the three genes were inserted into vaccinia, recombinant viral progeny did not plaque on MRC-5 cells. This indicated that M1L and N2L were not the presumptive host range gene(s). M2L was not expected to be the host range gene, since the gene for M2L is wholly contained in the BglII A fragment of EcoRI K previously tested (15).

The remaining possible vaccinia virus human host range genes were K2L, which is missing in the 18 kb host range mutant and truncated in vP293, and C7L, an ORF in HindIII C which spans the EcoRI C/J junction and has the coding capacity for an 18 kDa protein.

The K2L gene described herein corresponds to the "ORF K1L" previously reported (52) for WR strain vaccinia, differing by two amino acid substitutions. Vaccinia virus deletion mutant vP293 contains the bulk of the coding sequences for K2L immediately to the right of the deletion junction in HindIII K (equivalent to the SalI site at position 11412). To test the K2L gene (pos. 12367-11258) for its ability to permit vaccinia viral growth on human cells, the 3' end of the vaccinia K2L gene was restored to plasmid pMP528. Synthetic polylinkers MPSYN52 (5' ATTATTTTTATAAGCTTGGATCCCTCGAGGGTACCCCCGGGGAGCTCGAATTCT 3') and MPSYN53 (5' AGAATTCGAGCTCCCCGGGGGTACCCTCGAGGGATCCAAGCTTATAAAAATAAT 3') were annealed and ligated into the SsoI site (pos. 11177) downstream from the K2L gene in a plasmid subclone of Copenhagen HindIII K, and a XhoI/SalI fragment containing the 3' end of the K2L gene was isolated. Plasmid pMP528 was cut with SalI, and the XhoI/SalI fragment containing the 3' end of the K2L gene was inserted in the correct orientation (FIG. 11). The resulting plasmid, pMP528K2, was used as donor plasmid for recombination with vaccinia virus vP293. Once again, recombinant vaccinia viral progeny were unable to plaque on MRC-5 cells, indicating that K2L was not a human host range gene.

The Copenhagen vaccinia C7L gene described herein corresponds exactly on the amino acid level with the WR 18 kDa gene previously reported (40). To test the C7L gene (pos. 1314-863) for its host range ability, plasmid pSD420 was cut with BamHI and BglII and a 1040 bp fragment extending from the BamHI site at position 724 to the BglII site at position 1764 was isolated. This BglII/BamHI fragment, which contains the entire gene for C7L, was ligated into pMP528K2 which had been cut with BamHI (FIG. 11). When the resulting plasmid, pMP528C7L, was used as donor plasmid for recombination with vaccinia virus vP293, viral progeny were produced which plaque on MRC-5 cells. This indicated that C7L, like K1L, was a host range gene capable of specifying growth on human cells. Since the C7L gene spans the EcoRI C/J junction, it had not been tested previously (14).

EXAMPLE 8

DELETION OF THE C7L GENE FROM COPENHAGEN STRAIN OF VACCINIA VIRUS

Since, like K1L, the vaccinia virus C7L gene was capable of restoring the ability of the WR strain vaccinia vP293 deletion mutant to plaque on human cells, the effect of deleting the C7L gene from the Copenhagen strain of vaccinia, both as a single deletion and as a double deletion with the other host range gene, K1L, was investigated.

The construction of plasmids for the deletion of the gene for C7L and the generation of vaccinia recombinants deleted for C7L are presented schematically in FIG. 12. A HindIII map of the left end of the vaccinia genome is presented on the top line. The C7L gene is indicated by a striped box, direction of transcription indicated by an arrow. The BamHI-BglII DNA fragment (pos 725–1764) derived from plasmid pSD420 was blunt ended with Klenow fragment of *E. coli* polymerase and ligated into pUC18 which had been cut with PvuII, generating plasmid pMP420BB (FIG. 12). pMP420BB was linearized with EcoRV, which cuts within coding sequences for C7L, and a 3.2 kb SmaI ended DNA fragment consisting of the vaccinia 11 kDa promoter (dark arrow)/B galactosidase (dark stippled box, direction of gene indicated by an arrow) cassette was inserted. The resulting plasmid, pMPC7LKBG, contains the 11 kDa promoter/B-galactosidase cassette in a left to right orientation relative to vaccinia sequences. Recombination was performed using donor plasmid pMPC7LKBG and rescuing Copenhagen vaccinia virus, vP410, resulting in vaccinia recombinant, vP665, which was identified as a blue plaque in the presence of X-gal.

To delete the C7L gene from pMP420BB, the plasmid was linearized by cutting at the unique SacI (pos. 999) site in the C7L gene, followed by digestion with Bal 31 exonuclease. Mutagenesis (53) was performed on the double stranded template using a synthetic 46-mer oligonucleotide MPSYN234 (5' TGTCATTTAACACTATACTCATATACTGAATGGATGAACGAATACC 3'). In the resulting plasmid, pMPC7Δ, the C7L gene is deleted (site of deletion indicated by a triangle, FIG. 12), leaving flanking vaccinia arms of 140 bp to the left and 400 bp to the right. pMPC7Δ was used as donor plasmid to remove the interrupted C7L gene/11 kDa promoter/B galactosidase sequences from vP665, generating vP706, which was identified as a colorless plaque in the presence of X-gal. Both vP665 and vP706 grow on MRC-5 cells. This is expected, since these recombinants still contain the K1L host range gene.

To create a virus devoid of the genes for both K1L and C7L, pMPC7LKBG was used as donor plasmid for recombination with the K1L-deleted vaccinia virus recombinant vP661. The resulting virus, vP683, was selected as a blue plaque in the presence of X-gal. The C7L gene was deleted from vaccinia recombinant virus vP683 by recombination with donor plasmid pMPC7LΔ. The resulting double deletion recombinant vaccinia virus, vP716, was selected as a colorless plaque in the presence of X-gal. Both vP683 and vP716 fail to plaque on MRC-5 cells, indicating that the deletion of the two genes, K1L and C7L, is sufficient to prevent growth of vaccinia virus on human cells.

Table 2 compares the ability of vaccinia virus genes to restore host range functions to vaccinia virus deletion mutant, vP293. What is compared is the relative ability to replicate on human or monkey cells after the noted genes have been reintroduced into vaccinia virus vP293 by recombination.

TABLE 2

| Virus | Genes Inserted | Titer (pfu/ml) VERO | MRC-5 |
| --- | --- | --- | --- |
| vP293 | M1L | $1.7 \times 10^5$ | 0 |
| vP293 | K2L | $2.5 \times 10^5$ | 0 |
| vP293 | M2L, M1L, N2L | $1.5 \times 10^5$ | 0 |
| vP293 | K1L | $1.7 \times 10^5$ | $4.7 \times 10^3$ |
| vP293 | C7L | $1.4 \times 10^5$ | $5.9 \times 10^3$ |

EXAMPLE 9

COWPOX GENE ENCODING A 77 kDa PRODUCT

Unlike vaccinia virus, cowpox virus is capable of growth on Chinese Hamster ovary (CHO) cells. A region of the cowpox genome that permits vaccinia virus replication on CHO cells has been identified (54). The cowpox gene and promoter map to a 2.3 kb Hpa I fragment. The gene encodes a predicted translation product of 77 kDa. The cowpox gene has no significant homology at the DNA or protein level to either of the two vaccinia virus human host range genes; K1L (54) or C7L described herein.

Figure 13:
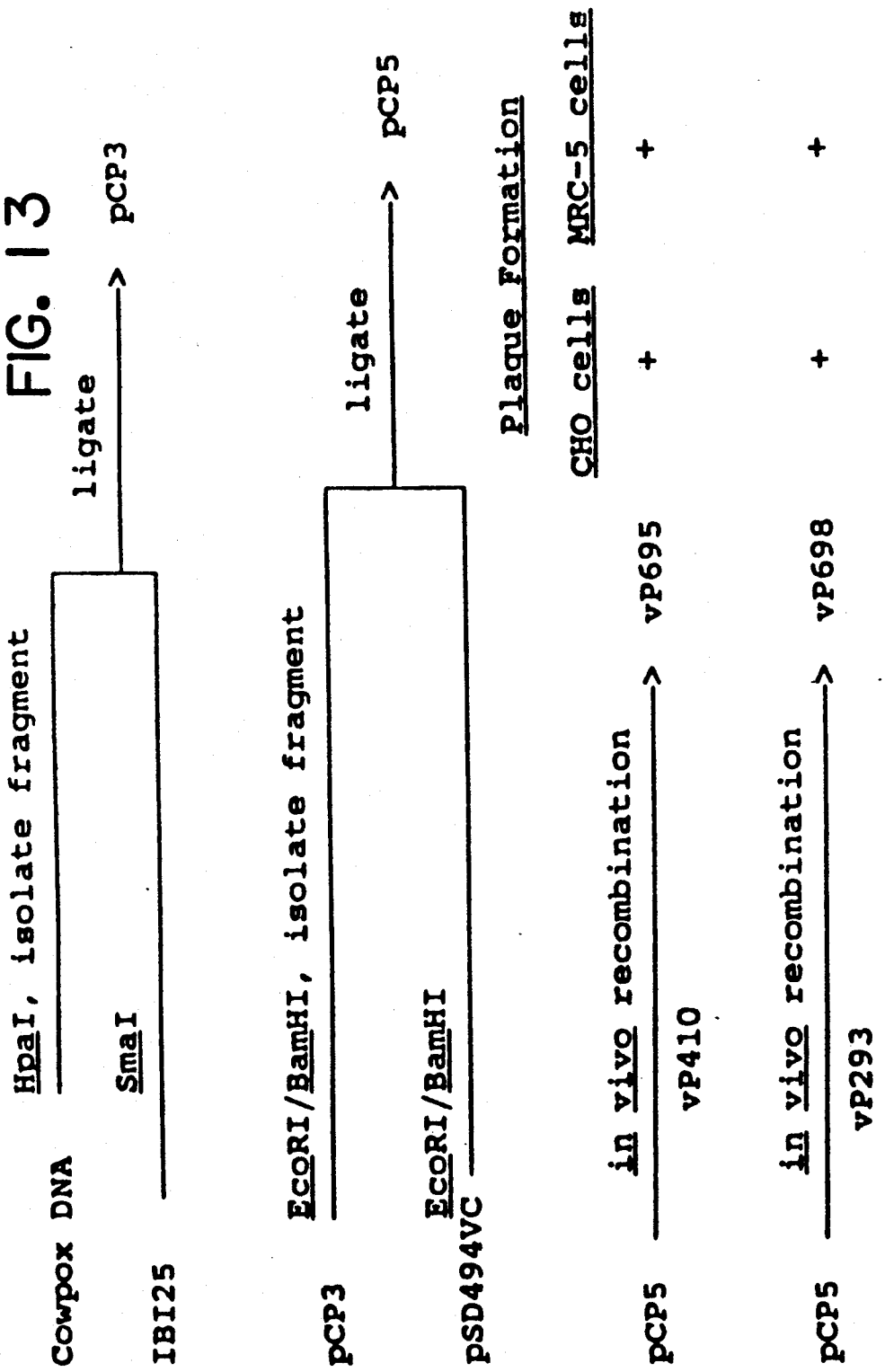
FIG. 13 schematically shows a method for the construction of plasmids pCP3 and pCP5 and for the testing of a potential cowpox host range gene in the vaccinia system.

Referring now to FIG. 13, as a preliminary to expressing the 77 kDa cowpox gene in the present vaccinia systems, cowpox DNA was digested with HpaI and the 2.3 kb fragment containing the gene and its promoter were isolated from an agarose gel. To flank the gene with polylinkers, the cowpox HpaI fragment was ligated into SmaI digested pIBI25 (International Biotechnologies, Inc., New Haven, Conn.), generating pCP3 (FIG. 13). For insertion into vaccinia, the cowpox gene was cloned into the ATI deletion region of the Copenhagen vector plasmid pSD494VC as described below.

The vaccinia equivalent of the cowpox ATI gene region in vaccinia WR strain was initially located by sequencing appropriate vaccinia WR clones using primers synthesized in accordance with the published DNA sequence at the 5' end of the cowpox ATI coding sequence (47). In contrast to cowpox, whose ATI gene encodes a 160 kDa protein, the WR vaccinia counterpart gene encodes a 94 kDa protein (see also 48). In contrast to WR, the Copenhagen strain of vaccinia virus contains a 4.1 kb deletion encompassing the 5' end of the ATI equivalent gene and the 3' end of the gene immediately preceding it. The remnants of the two ORFs are joined in frame to produce a hybrid ORF of 966 bp. Copenhagen vector plasmid pSD494VC is an XbaI/BpIII plasmid subclon of Copenhagen HindIII A in which the hybrid ORF formed by the fusion of the cowpox ATI counterpart gene in Copenhagen and its upstream neighbor are replaced by a polylinker region. The polylinker region consists of the sequence 5'A-GATCTCCCGGGAAGCTTGGATC-CGAGCTCCTCGAGGAATTCGTTAAC 3' specifying restriction sites BglII, SmaI, HindIII, BamHI, SstI, XhoI, EcoRI and HpaI. pSD494VC contains 0.7 kb of flanking vaccinia DNA to the left of the polylinker region and 1.3 kb of flanking vaccinia DNA to the right of the polylinker region.

A 2.3 kb EcoRI-BamHI fragment containing the cowpox 77 kDa gene and its promoter was isolated from pCP3. This fragment was ligated into the polylinker region of pSD494VC cut with EcoRI and BamHI, generating plasmid pCP5 (FIG. 13). As expected, recombination between pCP5 containing the 77 kDa cowpox gene and Copenhagen vaccinia virus vP410 produced a recombinant virus, vP695, which was able to plaque on CHO cells.

To test whether the 77 kDa cowpox CHO host range gene was also capable of specifying growth of vaccinia virus on human cells, recombination was performed between plasmid pCP5 containing the cowpox 77 kDa gene and vP293, the WR vaccinia host range deletion mutant which does not plaque on human cells. Recombinant progeny virus, vP698, plaqued on MRC-5 cells. This indicates that in addition to being a CHO host range gene, the 77 kDa cowpox gene, like the vaccinia genes K1L and C7L, is also a human host range gene (FIG. 13).

In light of the observation that the cowpox virus 77 kDa gene is capable of specifying the growth of vaccinia virus on both CHO and human MRC-5 cells, it was of interest to determine the roles of C7L and K1L, the two vaccinia human host range genes, on the ability of vaccinia virus to replicate in vitro on cells derived from other species. Also, it was of interest to determine whether other vaccinia-encoded genes were specifically required for growth of vaccinia virus on cells from other species. Initially, the series of Copenhagen vaccinia virus C7L and K1L deletion mutants were tested for their ability to plaque on LLC-PK1 cells, a cell line derived from pig kidney.

Confluent monolayers of VERO, MRC-5 and LLC-PK1 cells in 60 mm dishes were infected with 10-fold serial dilutions of virus in 200 ul volume Eagles MEM + 2% newborn calf serum. After a 1 h adsorption period the inoculum was removed and the monolayers were overlayed with 5 ml Eagles MEM containing 0.7% Seakem Le Agarose and 10% newborn calf serum. Dishes were incubated at 37° C. At 4 d post infection, the monolayers were stained by adding an additional layer consisting of 5 ml 0.6% agarose containing 0.04% neutral red. Plaques were observed 6 h after staining.

As shown in Table 3A, Copenhagen deletion mutants show identical plaquing abilities on pig kidney LLC-PK1 cells compared to human MRC-5 cells. Recombinant viruses which are deleted for either K1L (vP661)

or C7L (vP706), while retaining the other human host range gene, plaqued both on MRC-5 and LLC-PK1 cells. Recombinant virus deleted for both K1L and C7L (vP716) did not plaque on either MRC-5 or LLC-PK1 cells. Thus, based on the criterion of in vitro plaquing ability on the LLC-PK1 cell line, both vaccinia human host range genes K1L and C7L are also porcine host range genes. As was observed with the human cell line MRC-5, the presence of either K1L or C7L in the vaccinia genome is sufficient to allow plaquing of Copenhagen vaccinia virus on pig kidney LLC-PK1 cells. As in the case of vaccinia human host range genes, K1L and C7L are the only vaccinia porcine host range genes encoded in the Copenhagen strain of vaccinia virus since recombinant vaccinia virus vP716 (K1L−; C7L−) did not plaque on LLC-PK1 cells.

These results were confirmed using vaccinia virus recombinants containing the host range genes inserted into the WR vaccinia deletion mutant vP293 (Table 3B). As expected, vP293, which contains a large deletion spanning the C7L through K1L region, lacks the ability to plaque on LLC-PK1 cells. Insertion of the gene for K1L into vP293 is sufficient to permit growth of the resulting vaccinia recombinant (vP457) on LLC-PK1 cells. However, as was seen with human MRC-5 cells, insertion of the M1L gene into the WR deletion mutant, vP293, is not sufficient to permit plaquing of the resultant virus (vP596) on LLC-PK1 cells (Table 3B).

When either the vaccinia virus C7L or K1L gene or the cowpox virus 77 kDa gene is inserted into the WR deletion mutant vP293, the ability to plaque on human MRC-5 cells is restored (Table 3B). Similarly, the vP293-based vaccinia virus recombinants containing either C7L (vP638) or the cowpox 77 kDa gene (vP698) plaque on LLC-PK1 cells. Thus the cowpox 77 kDa gene, in addition to being a host range gene for Chinese hamster ovary (54) and human cells, is also a host range gene for porcine cells.

TABLE 3

| A. Copenhagen based deletion mutants | | | | |
|---|---|---|---|---|
| Virus | Deletion | VERO | MRC-5 | LLC-PK1 | CHO |
| vP410 | | + | + | + | − |
| vP661 | K1L | + | + | + | − |
| vP706 | C7L | + | + | + | − |
| vP716 | K1L, C7L | + | − | − | − |
| vP668 | [C7L-K1L] | + | − | − | − |

| B. WR vP293 based deletion mutants | | | | |
|---|---|---|---|---|
| Virus | Insert | VERO | MRC-5 | LLC-PK1 | CHO |
| vP293 | | + | − | − | − |
| vP457 | K1L | + | + | + | − |
| vP596 | M1L | + | − | − | − |
| vP638 | C7L | + | + | + | − |
| vP698 | cowpox 77kDa | + | + | + | + |

EXAMPLE 10

GROWTH OF COPENHAGEN DELETION MUTANTS ON HUMAN CELL LINES

Under customary conditions of growth (3 days, Noble Difco agar overlay), WR deletion mutant vP293 did not form plaques on human MRC-5 cell monolayers. However, with increased length of incubation or modification of the agar overlay vP293 can form small plaques on MRC-5 cell monolayers. Specifically, use of 0.6% to 1% Seakem agarose or low melting point agarose for the overlay instead of agar favors small plaque formation of vP293 virus on MRC-5 cells. Recombinant vaccinia progeny generated by recombination between vP293 and pHES-based plasmids containing the K1L gene (Example 3) form large plaques on an MRC-5 monolayer which are clearly distinguishable from the background of vP293 small plaques. Therefore, the ability of vP293 and the Copenhagen set of human host range deletion mutants to mount a restricted infection in MRC-5 and VERO cells under a liquid overlay was investigated.

Duplicate T-75 flasks were seeded with $5 \times 10^6$ MRC-5 or VERO cells as indicated. After two days confluent monolayers were infected at an moi of 0.01 pfu per cell (input titer $10^3$ pfu per flask) of vaccinia viruses as indicated in Table 3 in a volume of 0.5 ml MEM+newborn calf serum (NCS). After a 1 h adsorption period 10 ml of medium was added to each flask. One flask of each set was frozen immediately (1 hpi sample). The remaining flasks were incubated at 37° C. until 96 hpi and then frozen. Virus from all samples were harvested by 3 cycles of freezing and thawing and titered on VERO cells.

MRC-5 and VERO cells were infected at an moi of 0.01 pfu per cell. After 96 h incubation (96 hpi), virus was harvested and titered on VERO cells. Copenhagen mutants containing deletions of either human host range gene vP661 (C7L+, K1L−) and vP706 (C7L−, K1L+) displayed approximately equal multiplication (3 to 4 $\log_{10}$) on both MRC-5 and VERO cells, equivalent to the vP410 (C7L+, K1L+) control. Copenhagen mutants deleted for both human host range genes vP716 (C7L−, K1L−) and vP668 ([C7L through K1L]−) as well as WR deletion mutant vP293 (21.7 kb deletion) showed multiplication on VERO cells approximately equivalent to vP410, vP661 and vP706. Multiplication of deletion mutant viruses vP716, vP668 and vP293 was definitely positive on human MRC-5 cells, though drastically reduced compared to multiplication of these viruses on VERO cells. Under the conditions used here, all three vaccinia viruses, vP716, vP668 and vP293, which are deleted for both vaccinia human host range genes K1L and C7L are capable of productive but greatly restricted infection of human MRC-5 cells (approximately tenfold multiplication during 96 h infection). These results, shown in Table 4, are in agreement with earlier reports of a 2.3 fold multiplication during 36 h infection (6).

TABLE 4

Growth of vaccinia deletion mutants on VERO and MRC-5 cells

| | | Titer at 96 hpi[1] | | Multiplication of Virus[2] | |
|---|---|---|---|---|---|
| Virus | Deletions | VERO | MRC-5 | VERO | MRC-5 |
| vP410 | — | $1.9 \times 10^7$ | $1.0 \times 10^6$ | 5588 | 6250 |
| vP661 | K1L | $3.8 \times 10^7$ | $1.1 \times 10^7$ | 9268 | 3235 |
| vP706 | C7L | $2.3 \times 10^7$ | $8.6 \times 10^6$ | 10000 | 3440 |
| vP716 | C7L, K1L | $1.3 \times 10^7$ | $3.4 \times 10^4$ | 4375 | 11 |
| vP668 | [C7L-K1L] | $8.0 \times 10^6$ | $6.4 \times 10^4$ | 2857 | 21 |
| vP293 | [WR 21.7kb] | $6.9 \times 10^6$ | $6.4 \times 10^3$ | 3833 | 7 |

[1]Input titer equals $10^3$
[2]Ratio of titer at 96 hpi (hours post infection) to titer at 1 hpi (end of adsorption period)

To determine whether vaccinia virus deleted for the human host range genes C7L and K1L were capable of limited multiplication on human cell lines other than MRC-5, the multiplication of Copenhagen vaccinia virus mutant vP668 [C7L through K1L deletion] on three additional human cell lines compared to MRC-5 and VERO cells was assayed (Table 5).

Cells were seeded in 60 mm dishes at $1.5 \times 10^6$ cells per dish 2 days prior to infection. Vaccinia virus vP410 or vP668 at a moi of 0.01 pfu per cell in a volume of 0.5 m) of MEM+5% newborn calf serum (NCS) was added to duplicate dishes containing monolayers of each cell line. After an adsorption period of 1 h, 4 ml of medium was added to each dish and half of the dishes were frozen (1 hpi samples). The remaining dishes were incubated at 37° C. until 96 hpi, then frozen (96 hpi samples). All samples were harvested by 3 cycles of freezing and thawing, and virus titered on VERO cells. Two dishes were infected for each time point and the titers were averaged. Multiplication of each virus on each cell line is expressed as the ratio of titer obtained at 96 hpi over the titer at 1 hpi.

TABLE 5

Multiplication of Copenhagen vaccinia virus vP410 and vP668 on monkey and human cell lines[1]

| Cell line | virus | | % yield[2] |
|---|---|---|---|
| | vP410 | vP668 | vP668/vP410 |
| Monkey | | | |
| VERO | 70,212 | 13,103 | 18.6 |
| Human | | | |
| MRC-5 | 7,333 | 10 | 0.14 |
| WISH | 19,480 | 0.4 | 0.002 |
| HeLa | 50,000 | 0.4 | 0.0008 |
| Detroit | 9,660 | 2.8 | 0.03 |

[1]Cell lines used: VERO: Monkey kidney ATCC CCL 81; MRC-5: Human embryonal lung ATCC CCL 171; HeLa: Human cervix. epithelioid carcinoma ATCC CCL 2; WISH: Human amnion (HeLa markers) ATCC CCL 25; Detroit: Human foreskin ATCC CCL 54.
[2]% yield vP668/vP410 for each cell line is the ratio of the multiplication of vP668 (96 hpi/1 hip) divided by multiplication of vP410 (96 hpi/1 hpi) × 100.

vP668 virus shows a one log multiplication on MRC-5 cells during a 96 h incubation period. Yield of vP668 virus 96 h post infection (hpi) of Detroit (human foreskin) cell line is 2.8 times the titer following adsorption of the virus (1 hpi). For WISH (human amnion) and HeLa (human cervix epithelioid carcinoma) cell lines, yield of vP668 virus 96 hpi was less than that observed following adsorption at 1 hpi, indicating no viral replication of the Copenhagen vaccinia host-range deletion mutant vP668 on these cell lines. All cell lines were permissive for vaccinia virus, as shown by multiplication of control virus vP410. Others have also found differences in the ability of various human cell lines to support growth of their host range mutant (6).

EXAMPLE 11

HOST RANGE MUTANTS OF VACCINIA VIRUS AS VACCINE VECTORS

Host range mutants of vaccinia virus would provide advantages as recombinant vaccine vectors. Reduction or absence of replication should increase the perception of safety since the viral vector is replication defective in the subject species, for example man or swine as described above. This would advantageously reduce the opportunity of a runaway infection due to vaccination in the vaccinated individual and also diminish transmission from vaccinated to unvaccinated individuals or contamination of the environment.

To this end, these host range mutants are useful vaccine vectors. The vP293 deletion mutant (Example 3) harbors a foreign genetic element. Further to this end, recombinants containing pseudorabies virus genes (a pertinent swine vaccine) and recombinants expressing rabies virus glycoprotein (which has relevance for not only veterinary applications but also humans) also have been constructed and are described herein. One can readily appreciate that a variety of foreign genes can be utilized in these host range mutants. Furthermore, one can readily appreciate that additional species beyond those cited in this application can be scored for host range restriction of these vaccinia mutants by the present methods described herein.

Furthermore, one can readily appreciate that additional host range genes exist in poxvirus. For example, the vaccinia MVA vaccine strain is reported to be attenuated, particularly in immune suppressed animals. Recently it was reported that the K1L human host range gene is partially deleted in MVA (55). The present analysis of the MVA genome confirms the reported deletion in the K1L gene, but indicates that the second human host range gene, C7L, is present in MVA, even though the MVA vaccinia virus does not plaque on human cells. The promoter region upstream from the C7L gene in MVA is identical to the upstream region in Copenhagen presented here. The amino acid sequence of the putative C7L translation product for MVA is identical with that of Copenhagen. This indicates that the C7L human host range gene, which in both WR and Copenhagen appears to be functionally equivalent to the K1L human host range gene, is incapable, by itself, of specifying growth of MVA vaccinia virus on human cells. Further, replacement of the defective K1L gene in MVA with the intact K1L gene from Copenhagen does not confer to the hybrid vaccinia virus recombinant the ability to grow on human cells.

MVA vaccinia virus is also impaired in its ability to grow on monkey cells, suggesting the existence of other, as yet unidentified, host range gene(s). Utilizing approaches similar to those used here it should be possible to define the genes necessary for these restrictions.

Furthermore, it is well appreciated that other poxviruses such as avipox and swinepox are host restricted in regards replication to avian and swine species, respectively. These host restrictions clearly suggest the existence of a number of host range genes in the poxviruses. Definition of these genes by approaches defined in this specification can increase the repertoire of host range constructed poxvirus vectors.

EXAMPLE 12

INSERTION OF RABIES GLYCOPROTEIN GENE INTO THE TK DELETION LOCUS OF VARIOUS COPENHAGEN VACCINIA DELETION MUTANTS

The rabies glycoprotein was chosen as a model foreign antigen for insertion into various Copenhagen vaccinia deletion mutants to allow comparative analysis of the relative effects of these deletions. The gene for the rabies glycoprotein (18,42) was placed under the control of the synthetic vaccinia H6 promoter. This expression cassette was inserted into the Copenhagen TK deletion vector plasmid pSD513VC. pSD513VC is a subclone of Copenhagen vaccinia HindIII J fragment in which the coding sequences for the thymidine kinase (TK) gene (56) are replaced by a polylinker region. The polylinker region consists of the sequence 5' CCCGGGAGATCTCTCGAGCTGCAGGGCGCC-GGATCC 3' specifying restriction sites SmaI, BglII, XhoI, PstI, NarI and BamHI. The resulting plasmid containing the rabies glycoprotein gene was designated pRW842. In pRW842, coding sequences for the vaccinia TK gene are replaced by the H6 promoter/rabies glycoprotein gene cassette which is oriented in a left to right orientation relative to vaccinia flanking arms. Recombination between pRW842 and any vaccinia virus results in a TK minus virus which contains the rabies glycoprotein gene under the control of the H6 promoter.

Recombination was performed between pRW842 and the set of Copenhagen vaccinia viruses containing deletions of one or both of the human host range genes. The resulting set of vaccinia recombinants containing the rabies glycoprotein gene are listed in Table 6. Monkey (VERO) cells were infected with the set of vaccinia recombinants containing the rabies gene. Immune precipitations were performed using a monoclonal antibody specific for the rabies glycoprotein (42). All recombinants express the gene.

TABLE 6

| Copenhagen deletion mutants containing rabies glycoprotein gene | | | | |
|---|---|---|---|---|
| Parental Virus | Plasmid Donor | Recombinant Virus | Deletions | Rabies Glycoprotein Expression |
| vP410 | pRW842 | vP744 | TK | + |
| vP661 | pRW842 | vP745 | TK, K1L | + |
| vP706 | pRW842 | vP746 | TK, C7L | + |
| vP716 | pRW842 | vP750 | TK, C7L, K1L | + |
| vP668 | pRW842 | vP752 | TK, [C7L-K1L] | + |

Vaccinia recombinant vP750 contains the rabies glycoprotein gene in a C7L−, K1L− background. vP752 contains the rabies gene in a [C7L through K1L] deletion background. Since both of the human host range genes are missing in both of these vaccinia recombinants, productive infection of human cells by these recombinants would not be expected. To test whether the rabies gene can be expressed in human cells in the absence of the human host range genes, MRC-5 cells were infected with the entire set of vaccinia rabies recombinants, including vP750 and vP752. In all members of the set, immunofluorescence was detected on the surface of infected cells.

EXAMPLE 13

CLONING AND EXPRESSION OF PSEUDORABIES (PRV) GENES IN A VP668 BACKGROUND vP668, the Copenhagen vaccinia deletion mutant which contains a deletion spanning the region encompassing the human and porcine host range genes [C7L through K1L] was chosen as the basic vector. vP668 does not plaque on human MRC-5 cells or pig kidney LLC-PK1 cells (see Table 3). Pseudorabies genes gII, gIII and gp50, which contain homology to herpes simplex virus (HSV) genes gB (57), gC (58) and gD (59), respectively, were inserted into the vP668 vector as detailed below.

A. Insertion of the PRV glycoprotein gII gene into the HA deletion locus of Copenhagen vaccinia virus PRV DNA was digested with BamHI and the resulting fragments were cloned into pBR322 cut with BamHI. Plasmid pPR9.25, containing PRV BamHI fragment 1 (60) contains the entire gene for PRV glycoprotein gII. Portions of pPR9.25 containing the gene for gII (57) were subcloned into pBR322, pUC18 and M13 phage. The nucleotide sequence for the gII gene was determined (46).

The coding sequences for the PRV gII gene were inserted into the Copenhagen vaccinia vector plasmid pTP15 (50). In the resulting plasmid, pPR18, the gII gene is located in the Copenhagen vaccinia hemagglutinin (HA) deletion locus under the control of the H6 vaccinia promoter. Recombination between plasmid pPR18 and Copenhagen vaccinia deletion mutant vP668 resulted in vaccinia recombinant vP726. In vP726 the PRV gII gene is inserted in the HA deletion locus under the control of the vaccinia H6 early/late promoter. All extraneous PRV DNA 5′ and 3′ to the gene has been removed. A sequence specifying termination of early vaccinia transcription (39) has been inserted downstream from PRV gII coding sequences.

B. Insertion of the PRV gp50 gene into the ATI deletion locus of Copenhagen vaccinia virus DNA encoding the gene for the PRV glycoprotein gp50 is located on the BamHI fragment 7 of the PRV genome (61). Plasmid pPR7.1 contains the PRV BamHI fragment 7 cloned into the BamHI site of pBR322. A StuI/NdeI subfragment of pPR7.1 containing the entire gene for PRV gp50 was subcloned into pIBI25 generating plasmid pPR22. The nucleotide sequence for the gp50 gene was determined (46).

The coding sequences for PRV gp50 were placed under the control of the early/intermediate vaccinia promoter equivalent to the immediate upstream sequences of I3L (62,63). This promoter element has been used previously to express foreign genes in vaccinia virus recombinants (31,64). DNA corresponding to promoter sequences upstream from the I3L open reading frame (62) was synthesized by a polymerase chain reaction (65) using synthetic oligonucleotide primers P50PPBAM (5′ ATCATCGGATCCCGGTGGTTTGCGATTCCG 3′) and P50PPATG (5′ GATTAAACCTAAATAATTG 3′) and pMP1VC, a subclone of Copenhagen HindIII I, as template. The resulting fragment was digested with BamHI to generate a BamHI cohesive end at the 5′ end of the promoter sequence. The 3′ end remained blunt ended.

The PRV gp50 coding sequences were excised from plasmid pPR22. Plasmid pPR22 was digested with NsiI, which cuts 7 bp upstream from the ATG and results in a 3′ overhang. The 3′ overhang was blunt ended with T4 DNA polymerase in the presence of 2 mM dNTPs. The resulting DNA was partially digested with BglII, and a 1.3 kb blunt/BglII fragment containing the PRV gp50 gene was isolated.

The 126 bp I3L promoter fragment (BamHI/blunt) and the 1.3 kb gp50 gene containing fragment (blunt/BglII) were ligated into a pBS-SK plasmid (Stratagene, La Jolla, Calif.) vector digested with BamHI. The resulting plasmid was designated pBSPRV50I3. The expression cassette containing the I3L promoter linked to the PRV gp50 gene was removed by BamHI digestion followed by partial SmaI digestion. A 1.4 kbp fragment containing the I3L promoter/PRVgp50 gene was isolated and blunt ended using Klenow fragment of *E. coli* polymerase.

pSD541 is a Copenhagen deletion plasmid in which flanking arms for the ATI deletion region (see pSD494VC) were generated by polymerase chain reaction (PCR) (65) using subclones of Copenhagen HindIII A as template. Synthetic oligonucleotides MPSYN267

(5' GGGCTGAAGCTTGCGGCCGCTCAT-TAGACAAGCGAATGAGGGAC 3') and MPSYN268 (5' AGATCTCCCGGGCTCGAG-TAATTAATTAATTTTTATTACAC-CAGAAAAGACGGCTTGAGATC 3') were used as primers to make the 420 bp vaccinia arm to the right of the deletion. Synthetic oligonucleotides MPSYN269 (5' TAATTACTCGAGCCCGGGAGATCTAATT-TAATTTAATTTATATAACTCATTTTTT-GAATATAC T 3') and MPSYN270 (5' TATCT-CGAATTCCCGCGGCTTTAAATGGACG-GAACTCTTTTCCCC 3') were used as primers to make the 420 bp vaccinia ar to the left of the deletion. The left and right vaccinia arms generated above were mixed together and extended by a further polymerase chain reaction to generate a DNA fragment consisting of both left and right flanking vaccinia arms separated by a polylinker region specifying restriction sites BglII, SmaI and XhoI. The PCR-generated fragment was cut with HindIII and EcoRI to yield sticky ends, and ligated into pUC8 cut with HindIII and EcoRI. The resulting plasmid is pSD541.

Figure 14:
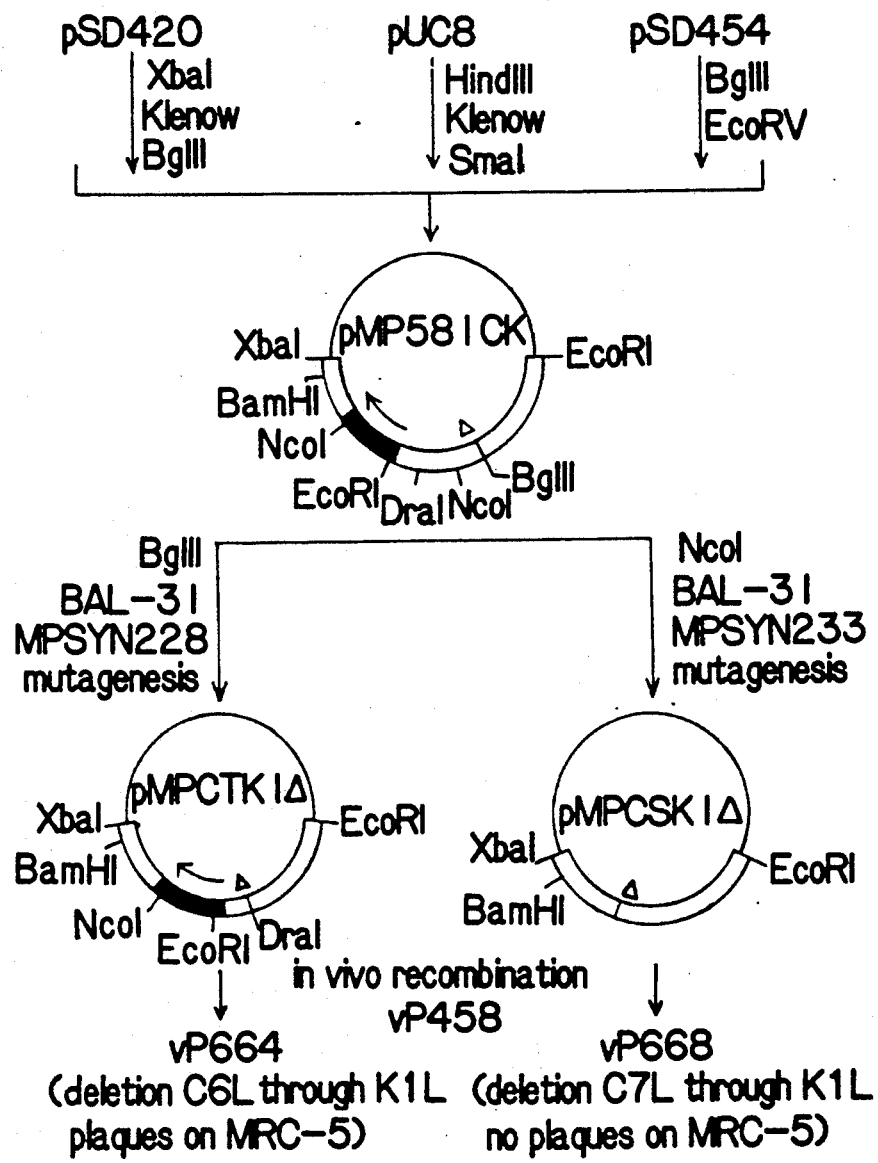
FIG. 14 schematically shows a method for the construction of recombinants vP66 and vP668.

The 1.4 kb blunt ended fragment containing the I3L promoter/PRVgp50 gene was inserted into Copenhagen vector plasmid pSD541 digested with SmaI. In the resulting plasmid, pATIp50, the PRV gp50 gene is located in the Copenhagen vaccinia ATI deletion locus under the control of a 126 bp vaccinia I3L promoter element. In pATIp50 all extraneous PRV DNA 3' to the gene has been removed. 7 bp of extraneous PRV sequences remain immediately upstream of the PRV gp50 ATG. An early vaccinia transcriptional termination sequence (39) is located downstream from PRV gp50 coding sequences. Recombination between plasmid pATIp50 and Copenhagen vaccinia deletion mutant vP668 was performed.

C. Insertion of the PRV glycoprotein gIII gene into the TK deletion locus of Copenhagen vaccinia virus The coding sequences for PRV glycoprotein gIII map to BamHI fragments 2 and 9 of the PRV genome (58). Plasmids pPR9.9 and pPR7.35 contain PRV BamHI fragments 2 and 9, respectively, cloned into the BamHI site of pBR322. An SphI/BamHI fragment containing the 5' end of the PRV gIII gene was isolated from pPR9.9. An NcoI/BamHI fragment containing the remainder of the gIII gene was isolated from pPR7.35. The entire PRV gIII gene was assembled by ligating the two fragments into pIBI25, resulting in plasmid pPR17. The nucleotide sequence for the gIII gene was determined (46).

The PRV gIII gene was placed under the control of a Copenhagen vaccinia u promoter element resulting in plasmid pPR24 (vaccinia u promoter sequence is described in Example 5, FIG. 5). An expression cassette containing a 120 bp vaccinia u promoter element and the entire PRV gpIII gene was excised from plasmid pPR24 by digestion with SnaBI (at position −120 upstream from the initiation codon and with DraI downstream from the PRV gIII gene. The 1.5 kb blunt ended fragment containing the u promoter/PRV gpIII gene was isolated and ligated into SmaI digested Copenhagen vector plasmid pSD513VC to yield pPRVIIIVCTK. In pPRVIIIVCTK, vaccinia TK coding sequences are replaced by the PRV gIII gene inserted in a right to left orientation under the control of the 120 bp Copenhagen vaccinia u promoter element. All extraneous PRV sequences 5' and 3' to the gIII gene have been removed. Recombination between plasmid pPRVIIIVCTK and Copenhagen vaccinia deletion mutant vP668 was performed.

D. Expression of PRV gII in vaccinia recombinant vP726

Expression of PRV gII in Copenhagen vaccinia recombinant vP726 was tested in VERO, LLC-PK1 and MRC-5 cells. vP726 contains PRV gII in a vP668 background [C7L through K1L deletion], and thus would not be expected to mount a productive infection in pig kidney LLC-PK1 and human MRC-5 cells. Nevertheless, immunofluorescence analysis using a monoclonal antibody specific to PRV gpII surprisingly demonstrated the expression of the PRV gpII gene product in pig, monkey and human cells.

E. Construction of double and triple PRV recombinants in the vP668 Copenhagen vaccinia virus background Recombination was performed to construct vaccinia recombinants containing multiple PRV genes. Recombinations have been performed using donor plasmids pATIp50 (PRV gp50, ATI deletion locus) and pPRVIIIVCTK (PRV gIII, TK deletion locus) and rescuing virus vP726, the Copenhagen vaccinia recombinant which contains PRV gII in the HA deletion locus in a [C7L through K1L] deletion background. These recombinations generate vaccinia recombinants containing double insertions of PRV genes gII+gp50 and gII+gIII, respectively. One of these vaccinia double PRV recombinants is used as rescuing virus for recombination with the appropriate plasmid to generate the triple recombinant containing PRV genes gII+gp50+gIII.

EXAMPLE 1

CONSTRUCTION OF A COPENHAGEN STRAIN VACCINIA VIRUS BASED HOST RANGE SELECTION SYSTEM

To construct a Copenhagen vaccinia virus based host range selection system (COPCS), plasmids were constructed to delete DNA encompassing the region encoding the genes from C7L on the left through K1L on the right (FIG. 8). Vaccinia viruses containing this deletion would not be expected to grow on human cells since both host range genes C7L (Example 7) and K1L (15) were deleted. Plasmids were also constructed to delete the region extending from C6L through K1L. Since the C6L through K1L deletion does not remove the human host range gene, C7L, vaccinia viruses containing this deletion would be expected to grow on human cells.

Referring now to FIG. 14, a plasmid pSD420 (FIG. 14) containing a SalI clone of Copenhagen vaccinia virus DNA (FIG. 8,10) was prepared. A fragment from the HindIII C region of Copenhagen strain vaccinia virus was derived from pSD420 by cleavage with XbaI (pos. 685) followed by blunt ending with Klenow fragment of *E. coli* polymerase and cleavage with BglII (pos. 1764). The resulting 1079 bp fragment was isolated from an agarose gel. pSD451 (FIG. 9,14) is a plasmid containing Copenhagen vaccinia DNA between the SphI site in HindIII M (pos. 9478) and the KpnI site in HindIII K (pos. 12998). A fragment from the HindIII K region of Copenhagen strain vaccinia virus was derived from pSD451 by cleavage with BglII (pos. 11116) and EcoRV (pos. 11834). The 718 bp restriction fragment was isolated from an agarose gel. Both fragments were ligated into pUC8 which had been cleaved with HindIII, blunt ended with Klenow fragment of *E. coli* polymerase, and cleaved with SmaI (FIG. 14). The resulting plasmid was designated pMP581CK. pMP581CK (FIG. 14) contains the C7L gene (solid block, direction of transcription indicated by arrow). pMP581CK contains a unique BglII site flanked by a left vaccinia arm (pos. 685-1764) derived from Hind III C and by a right vaccinia arm (pos. 11116-11834) derived from Hind III K. The left vaccinia arm contains the entire gene for C7L (coding sequences pos. 1314-863). Relative to the Copenhagen vaccinia genome, the two arms are separated by a 9351 bp deletion (pos. 1315-11115). The site of deletion between HindIII C sequences and HindIII K sequences is indicated by a triangle in FIG. 14.

To remove excess DNA at the deletion junction, pMP581CK was cut with BglII, followed by digestion with Bal 31 exonuclease. Mutagenesis (53) was performed on the double stranded template using a synthetic 49mer oligonucleotide MPSYN228. (5' TTTCTTAATAAATATTATTTTTATT-TAAATTCGTAGCGATATATAAAAC 3') The resulting plasmid, pMPCTK1Δ retains the vaccinia human host range gene, C7L. It is deleted between positions 1513-11165, and is deleted for eleven genes C6L through K1L (FIG. 8). Recombination between plasmid pMPCTK1Δ and vP458, a recombinant Copenhagen vaccinia virus containing the *E. coli* lacZ gene in the M2L deletion locus, generated vaccinia recombinant vP664. As expected, vP664 is able to plaque on human cells since it retains an intact C7L gene.

To remove the coding sequences pos. 1314–863) for C7L and excess DNA at the deletion junction, pMP581CK was cut with NcoI, followed by digestion with Bal31 exonuclease. Mutagenesis (53) was performed on the double stranded template using a synthetic 44mer oligonucleotide MPSYN233. (5' TGTCATTTAACACTATACTCATAT-TAATAAAAATAATATTTATT 3'). The resulting plasmid, pMPCSK1Δ, is deleted between positions 862–11163 and is deleted for twelve genes C7L through K1L. Recombination between plasmid pMPCSK1Δ and vP458 generated vaccinia recombinant vP668. As expected, vP668 is unable to plaque on human cells since both host range genes K1L and C7L have been deleted.

A series of plasmids were derived from pMPCTK1Δ by addition of synthetic polylinker DNA at the deletion junction. Construction of plasmids in the COPCS series is summarized in FIGS. 15–7. DNA sequence for all synthetic oligonucleotides used in the construction of these plasmids are presented in FIGS. 15–17.

Plasmid pMPCTK1Δ (FIG. 14) was subjected to partial DraI digestion and linear DNA was isolated from an agarose gel. Synthetic oligonucleotides MPSYN238/MPSYN239 were annealed and ligated into pMPCTK1Δ in a right to left orientation at the deletion junction, resulting in plasmid pMPCS-1.

To add a stop codon to a small open reading frame entering the polylinker region from the left (ATG pos. 1485), pMPCS-1 was cut with PstI. Mutagenesis was performed (53) using a synthetic 72 mer oligonucleotide MPSYN249. (5' GTTTGTTTTATATATCGCTAC-GAATTTAAATAAAAATTATTTATT-TATAGATCTAGAGTCGAC CCGGGTACC 3'). The resulting plasmid, pCOPCS-4 (referred to in FIG. 17 by its alternate designation, pMPCS-4), has no open reading frames entering or leaving the polylinker region.

To add the vaccinia H6 promoter to the polylinker region, pMPCS-1 was cut with HindIII and Asp718. A synthetic HindIII/Asp718 DNA fragment consisting of the modified H6 promoter (Example 3) was inserted, resulting in plasmid pCOPCS-3H (promoter sequence given in FIG. 17). All subsequent plasmids, pCOPCS-5H through pCOPCS-10H, derived from pCOPCS-3H contain the H6 promoter region which is indicated in FIG. 17 for pCOPCS-3H. The bracketed sequence following the promoter region in pCOPCS-3H is replaced by the bracketed sequences indicated for pCOPCS-5H through pCOPCS-10H. The ATG initiation codons for plasmids pCOPCS-6H through pCOPCS-10H are underlined. Note that pCOPCS-3H and pCOPCS-5H do not contain ATG initiation codons upstream from the polylinker region. Translational frame beginning from the ATG in plasmids pCOPCS-6H through pCOPCS-10H is indicated. To add a stop codon to the small open reading frame from pMPCS-1 referred to above, the equivalent mutagenesis using MPSYN249 was performed on pCOPCS-3H, resulting in plasmid pCOPCS-5H.

To add an ATG initiation codon to plasmid pCOPCS-5H downstream from the H6 promoter in all reading frames relative to the polylinker restriction sites, pCOPCS-5H was cut at the NruI site in the H6 promoter and at the BglII site in the polylinker region. Vector fragment was isolated from an agarose gel. Synthetic oligonucleotides MPSYN250/MPSYN251 were annealed and inserted into the pCOPCS-5H vector, resulting in plasmid pCOPCS-6H Synthetic oligonucleotides MPSYN252/MPSYN253 were annealed and inserted into the pCOPCS-5H vector, resulting in plasmid pCOPCS-7H.

Synthetic oligonucleotides MPSYN254/MPSYN255 were annealed and inserted into the pCOPCS-5H vector, resulting in plasmid pCOPCS-8H.

pCOPCS-6H, pCOPCS-7H and pCOPCS-8H contain the H6 promoter with ATG initiation codon followed by restriction sites in the three different reading frames. The first and second amino acids encoded in these plasmids are as follows: pCOPCS-6H met/val; pCOPCS-7H met/gly and pCOPCS-8H met/gly. Since the met/gly motif in some contexts (66) can specify myristylation of the translated polypeptide, plasmid pCOPCS-6H was modified to generate plasmids containing ATG initiation codons in the other two reading frames which, like pCOPCS-6H, do not begin translation with the met/gly motif. pCOPCS-6H was cut with NruI and Asp718 and vector fragment was isolated from an agarose gel. Synthetic oligonucleotides MPSYN271/MPSYN272 were annealed and inserted into the pCOPCS-6H vector, resulting in plasmid pCOPCS-9H.

Synthetic oligonucleotides MPSYN273/MPSYN274 were annealed and inserted into the pCOPCS-6H vector, resulting in plasmid pCOPCS-10H. The first two amino acids encoded in these plasmids is as follows: pCOPCS-9H met/ser and pCOPCS-10H met/thr.

In the final COPCS series, DNA consisting of coding sequence with a promoter are inserted for expression into pCOPCS-4; coding sequences containing an ATG are inserted for expression into pCOPCS-5H; and coding sequences without an ATG initiation codon are inserted for expression in the appropriate reading frame into one or more of the pCOPCS-6H through pCOPCS- 10H series. The resulting plasmids are recombined into Copenhagen vaccinia virus deletion mutant vP668, restoring the ability of vaccinia virus to plaque on human cells.

EXAMPLE 15

UTILITY OF THE COPCS SYSTEM FOR ANALYZING PROMOTER STRENGTH

The ability of recombinant vaccinia progeny generated by recombination using the Copenhagen vaccinia virus vP668/COPCS plasmid host range selection system to plaque on human MRC-5 cells permits rapid identification of recombinants. The vP668/COPCS system can be used to generate vaccinia recombinants for a variety of purposes.

Plasmid pCOPCS-4, a member of the COPCS series which does not contain a promoter upstream from its polylinker region, was cut with BglII. A BglII fragment containing the complete coding sequence for the rabies glycoprotein gene (18,42) was inserted into pCOPCS-4 in a right to left orientation, resulting in plasmid pCOPCS-RAB. In pCOPCS-RAB the polylinker region is located upstream from the rabies gene. A variety of synthetic promoter regions and promoters derived from vaccinia virus or other poxviruses have been inserted into the polylinker region of pCOPCS-RAB, upstream from the rabies glycoprotein gene. The resulting plasmids are used in recombination with vaccinia virus Copenhagen deletion mutant vP668. Recombinant progeny are selected by their ability to plaque on MRC-5 cells. Relative promoter strength can be assayed by quantitating expression of the rabies glycoprotein gene in the recombinant progeny virus using monoclonal antibody. Additional utilities are comparable to the vP293 host range selection system.

EXAMPLE 16

DELETION OF THE INVERTED TERMINAL REPEATS OF VACCINIA VIRUS

Large amounts of DNA can be deleted from vaccinia virus without destroying its ability to grow in tissue culture. To increase stability of the vaccinia genome and remove nonessential genes which may be associated with virulence, a deletion within a single vaccinia virus recombinant of 32.7 kb of DNA from the left terminus and 14.9 kb of DNA from the right terminus was engineered.

The genome of vaccinia virus is composed of double stranded DNA. At each terminus, the DNA of complementary strands is crosslinked by a DNA strand which forms an incompletely base-paired terminal loop (67). Immediately internal to the terminal loop the genome contains sets of tandem repeats. A cloned version of the WR genome has been reported to contain 13 tandem copies of a 70 bp repeat unit near each end of the genome, separated by 435 bp of non-repetitive DNA from an additional block of 17 tandem copies of the 70 bp repeat unit (68). The terminal loop and repetitive DNA form the distal portions of the vaccinia inverted terminal repetition. The inverted terminal repetition, Which has been estimated at 10 kb for the cloned version of WR (69), contains a number of genes which, since they are contained in both the left and right copies of the inverted terminal repetition, are present in two copies in the vaccinia genome.

When DNA extracted from the plaque-cloned stock of Copenhagen vaccinia virus (VC-2) utilized here is digested with restriction endonucleases and analyzed on an agarose gel, the terminal fragments exhibit heterogeneity. Rather than running as a single band, terminal fragments appear as a ladder, the rungs of which are separated in size by about 1 kb. About 80% of the vaccinia virus recombinants derived as plaque isolates from VC-2 or its derivatives which themselves contain heterogeneous termini are found by restriction analysis to contain heterogeneous termini. In the remaining 20% of vaccinia recombinants, heterogeneity of termini has been lost, and the terminal DNA restriction fragments appear as discrete bands. When new recombinants are derived from virus with discrete termini, these recombinants are always observed to contain discrete termini.

Since the termini of stock virus VC-2 were heterogeneous, we chose to clone into a plasmid the terminal fragment from recombinant virus vP452, a VC-2 derivative which contains discrete termini. vP452 is deleted for vaccinia genes TK (thymidine kinase) and HA (hemagglutinin) (50). DNA was extracted from vP452 and digested with XhoI, and the 2 molar terminal band of approximately 7 kb was isolated from an agarose gel. Isolated fragment was subjected to limited digestion with BAL-31 exonuclease, followed by blunt ending with Klenow fragment of *E. coli* polymerase. The blunt ended fragment was cloned into the SmaI site of pUC8, producing pSD522VC (FIG. 18).

DNA sequencing of pSD522VC reveals that, as in the case of WR vaccinia, the termini of Copenhagen vaccinia recombinant vP452 contain tandem repeat units. In addition to the blocks of 70 bp tandem repeat units reported for the plaque cloned WR isolate, the termini of vP452, unlike the WR isolate, contain tandem repeat units composed of 54 bp located internal to the 70 bp tandem repeat units and proximal to coding sequences. FIG. 19 lists the sequence of a portion of the Copenhagen genome, beginning with the most internal copy of the 54 bp tandem repeat unit (pos.1–54). The 13978 bp sequence presented in FIG. 19 was derived from pSD522VC and various clones of VC-2 Copenhagen DNA in pUC-based plasmids. It includes coding sequences in HindIII C rightward of the final block of tandem repeats. The sequence presented in FIG. 19 ends at the SalI site which is the beginning of the sequence of Copenhagen DNA presented in FIG. 8.

To generate a plasmid containing the vaccinia repetitive DNA derived from the terminus of vP452 but deleted for vaccinia coding sequences, pSD522VC was digested with ClaI and HindIII, and a 7 kb fragment isolated. Synthetic oligonucleotides MPSYN261 (5' CGATTCAGACACACGCTTTGAGTTTTGTT-GAATCGAGATCTA 3') and MpSYN262 (5' AGCT-TAGATCTCGATTCAACAAAACT-CAAAGCGTGTGTCTGAAT 3') were annealed and ligated into the pSD522VC vector fragment, generating pMPVCEND. pMPVCEND contains vaccinia DNA from the end of pSD522VC (approximately 50 bp from the end of the genome) through all blocks of tandem repeats, ending at the ClaI site at position 338 of FIG. 19. A small ORF (positions 292–336) which crossed the ClaI site at position 305 was reconstructed in the synthetic oligonucleotides MPSYN261/MPSYN262, which also introduce a BglII site for ease of future cloning steps. pMPVCEND, which contains no ORFs proceeding from internal vaccinia DNA toward the terminus, was used as the plasmid vector and external arm in the creation of plasmids designed to delete genes from both the left and right termini of vaccinia.

Near the left terminus, all genes through the gene encoding the small subunit of ribonucleotide reductase, which resides in HindIII F (70), were deleted. The sequence for Copenhagen HindIII F was determined, and is presented in FIG. 20. Vaccinia HindIII F is located immediately to the right of HindIII K. The DNA sequence presented in FIG. 20 is contiguous with the sequence presented in FIG. 8, which includes the entire sequence for HindIII K. The small subunit for ribonucleotide reductase is encoded by ORF F4 (positions 3506-2547, FIG. 20).

To test whether the 10 genes (K2L through F4L) immediately to the right of the vP668 deletion (C7L through K1L) were nonessential, a plasmid, pMLPCTFRΔ, was constructed as follows. pSD521VC is a subclone of Copenhagen HindIII F, containing sequences from the HindIII K/F junction (junction of FIG. 8/FIG. 20) Appendices A/C through the unique BamHI site of HindIII F (FIG. 20, position 5663). To obtain a flanking arm to the right of F4, pSD521VC was cut with ClaI at position 3576, upstream from F4 coding sequences, and with BglII at position 2841, within F4L coding sequences. Synthetic oligonucleotides MPSYN256 (5' CGATGTACAAAAATCCAAGTACAGGCATATAGATAACTGA 3') and MPSYN257 (5' GATCTCAGTTATCTATATGCCTGTACTTGGATTTTTTGTACAT 3') were annealed and ligated into the vector plasmid pSD521VC between the ClaI and BglII sites. In the resulting plasmid, pMP256/257, the promoter region upstream from the F4 ORF is recreated, linked to a BglII site. To obtain a right vaccinia flanking arm, pMP256/257 was cut with BglII nd EcoRI, and a 2.3 kb fragment containing vaccinia sequences upstream from the F4 gene was isolated. The left vaccinia flanking arm from HindIII C was obtained from plasmid pCOPCS-4 (Example 14), which contains the gene for C7L and a further 140 bp of vaccinia DNA to the left. pCOPCS-4 was cut with BglII and EcoRI, and the 3.5 kb vector fragment ligated with the 2.3 kb fragment containing the right arm from HindIII F. The resulting plasmid, pMPCTFRΔ, contains a left vaccinia arm from HindIII C and a right arm from HindIII F flanking a deletion of 20 genes [C6L-F4L]. pMPCTFRΔ was used as donor plasmid for recombination with vP668 (Example 9), and recombinant virus selected by growth on MRC-5 cells. Viable vaccinia progeny vP749 (C6L-F4L deletion) was recovered, proving that all genes in the deleted region are nonessential.

Figure 18:
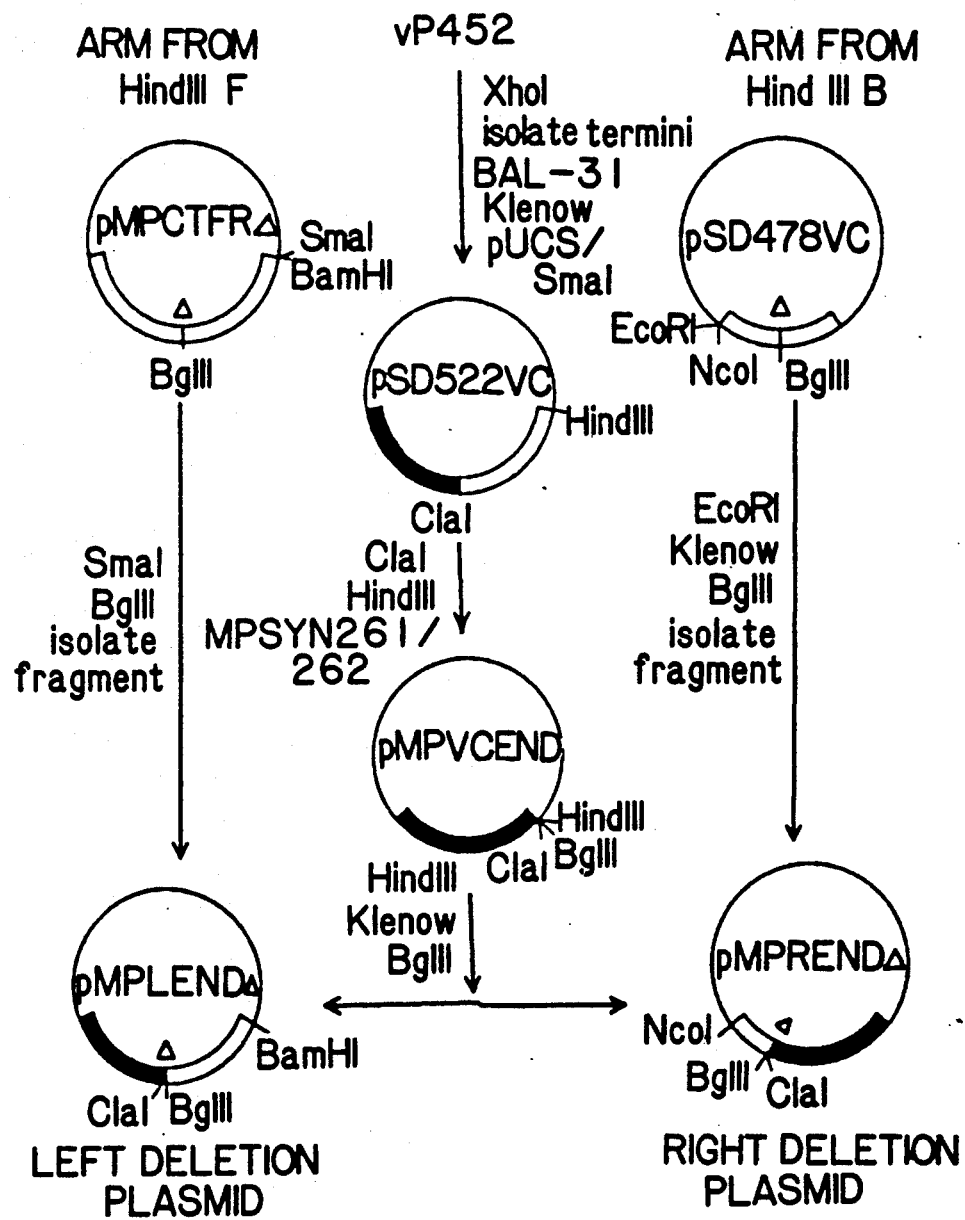
FIG. 18 schematically shows a method for the construction of plasmids pMPLENDΔ and pMPRENDΔ.
Figure 19A:
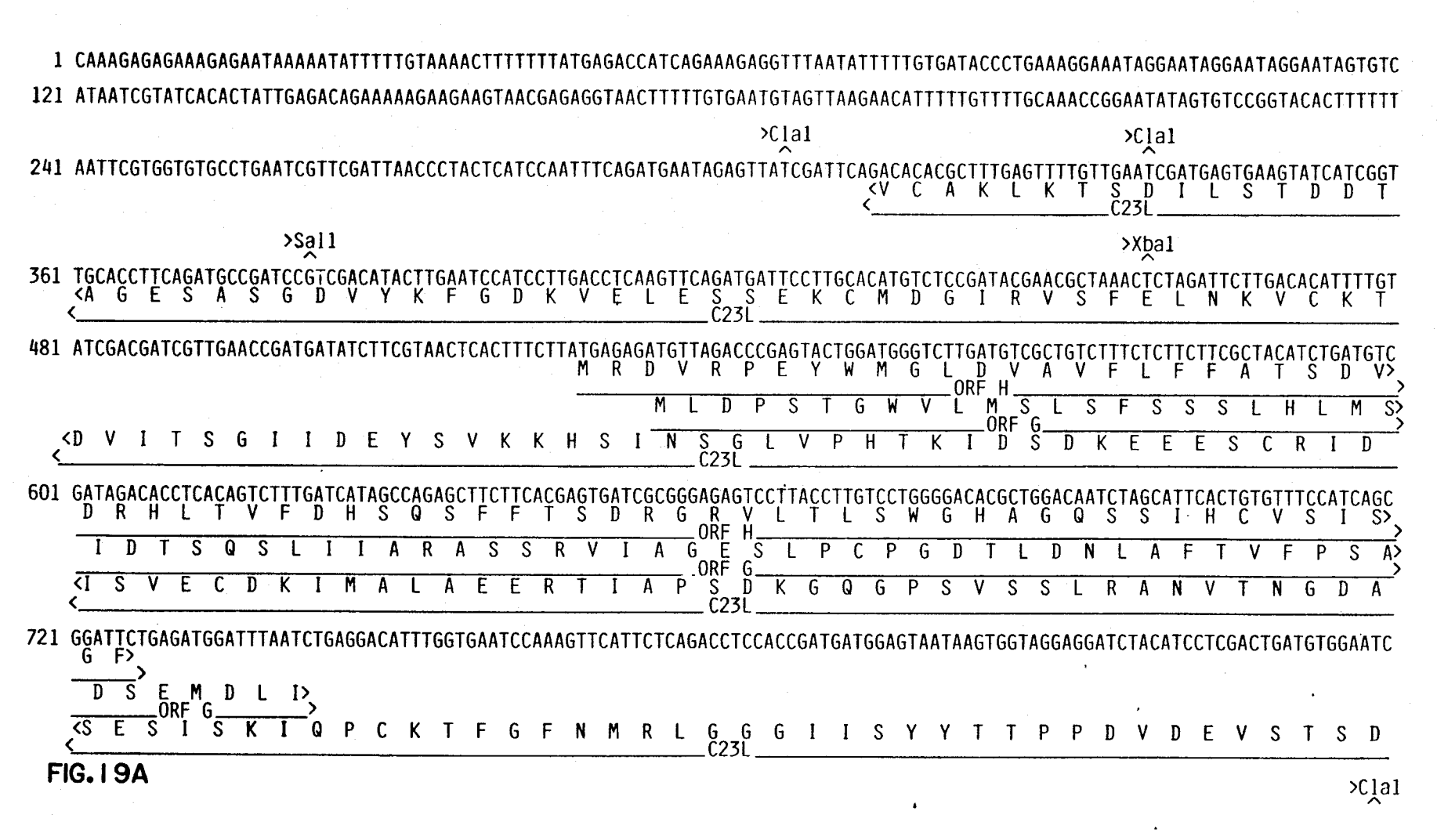
Figure 19B:
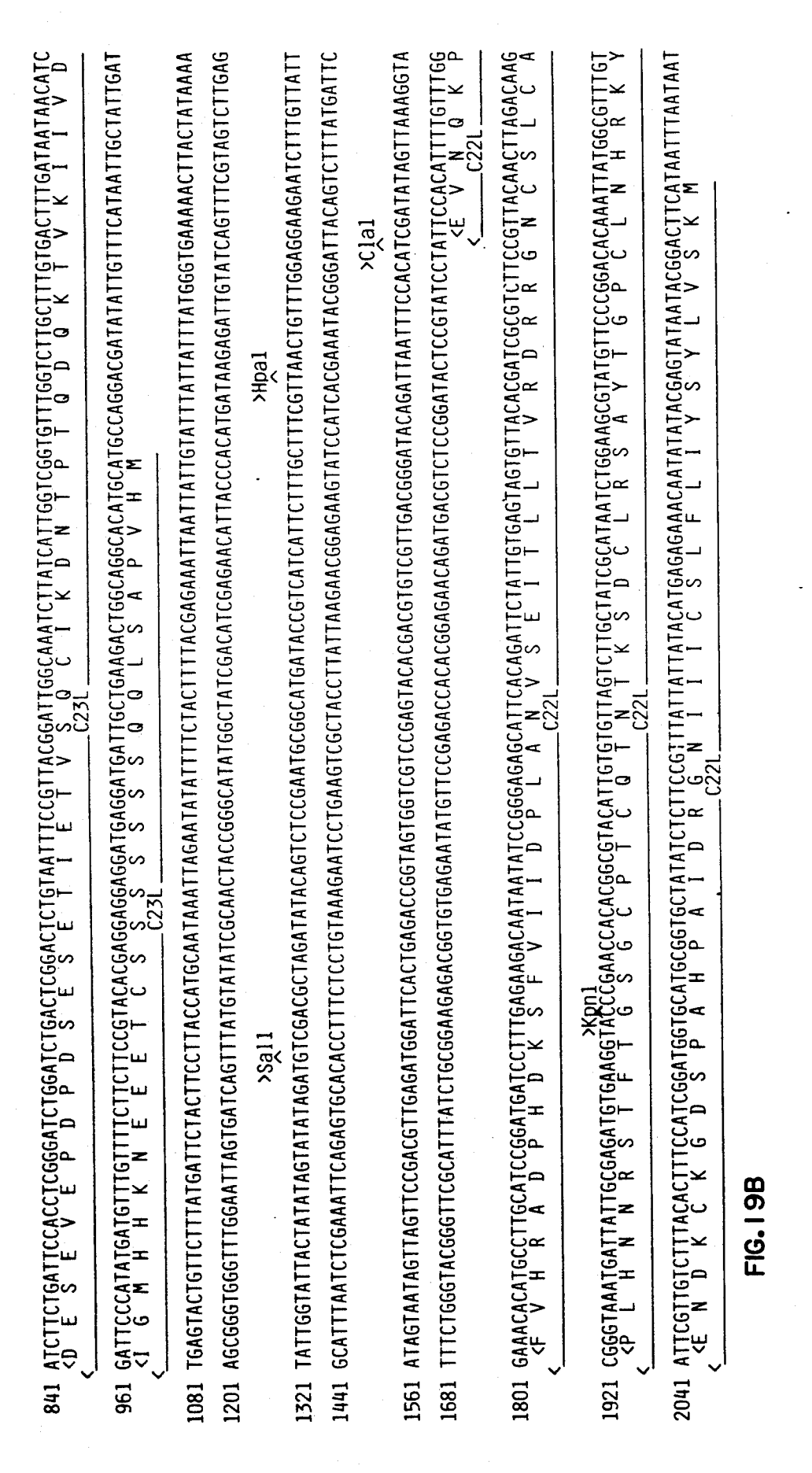
Figure 19C:
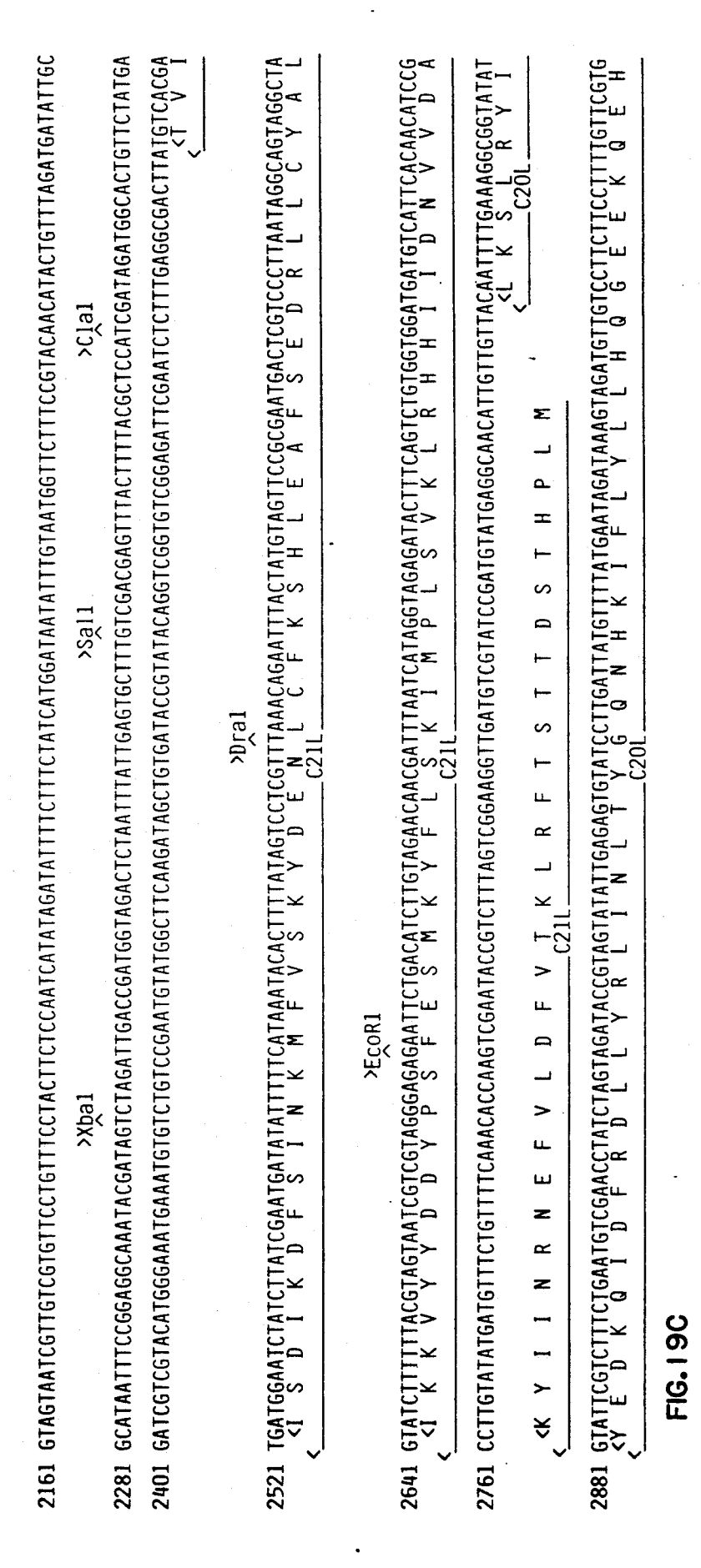
Figure 19D:
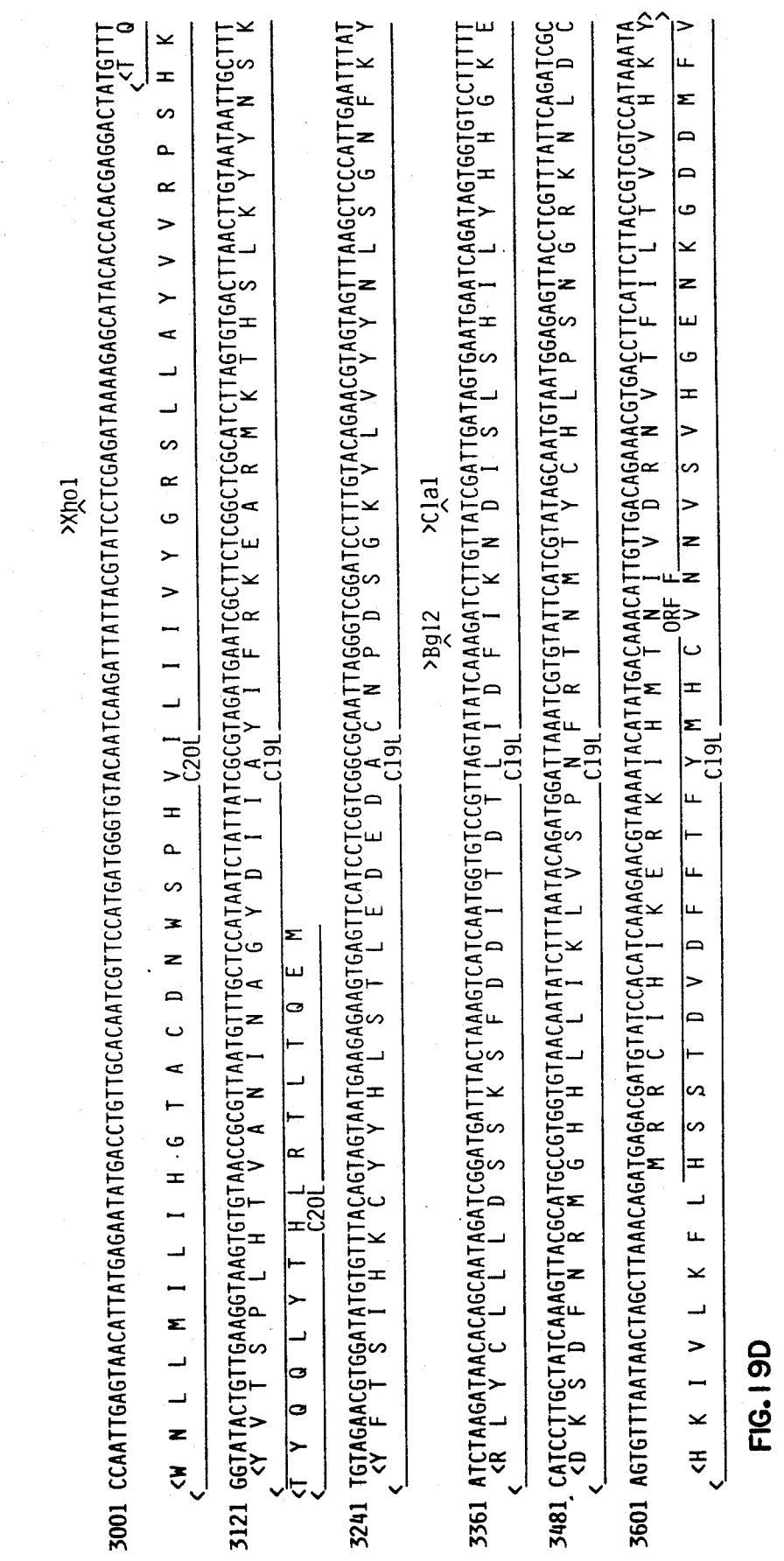
Figure 19E:
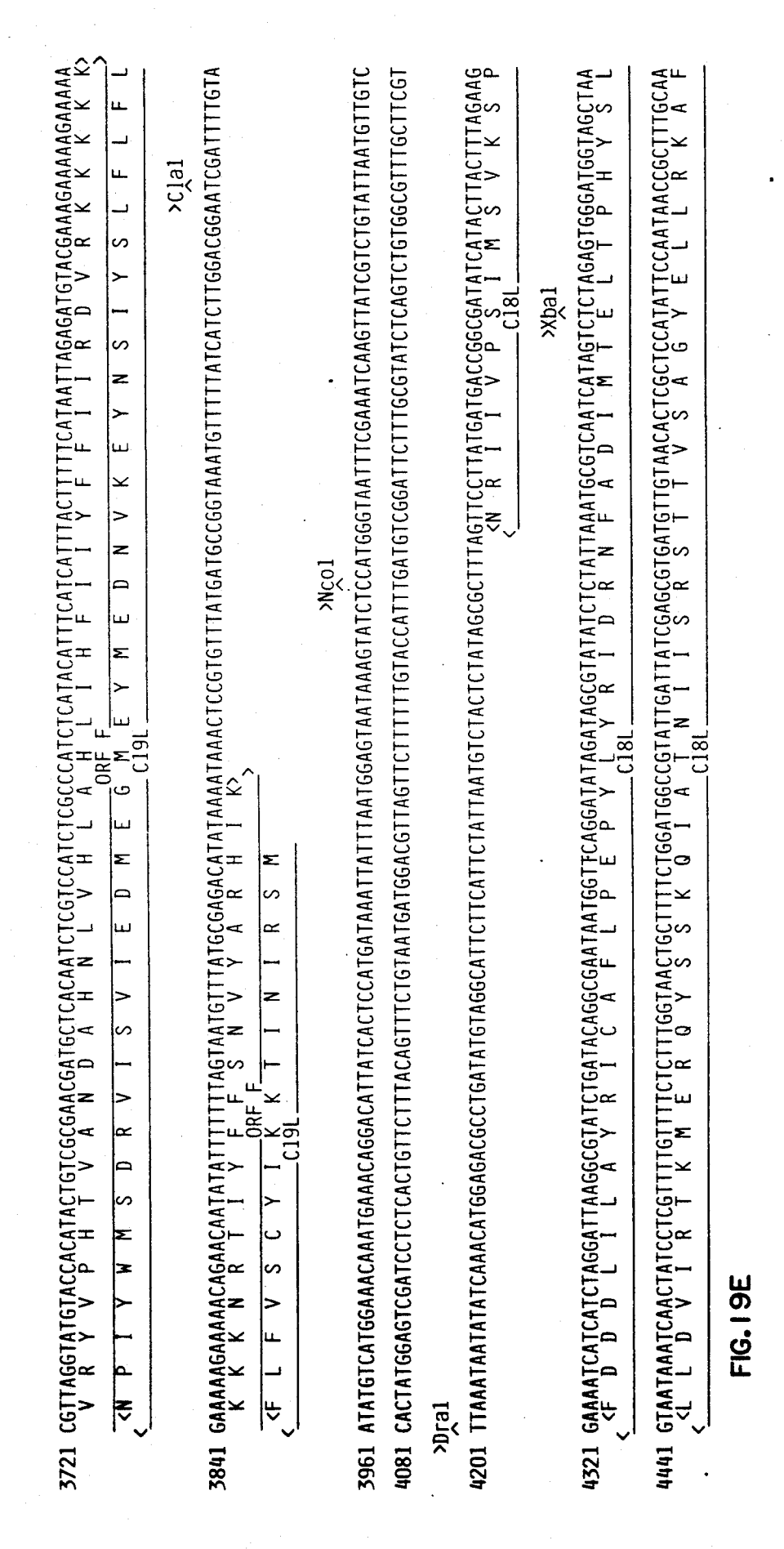
Figure 19F:
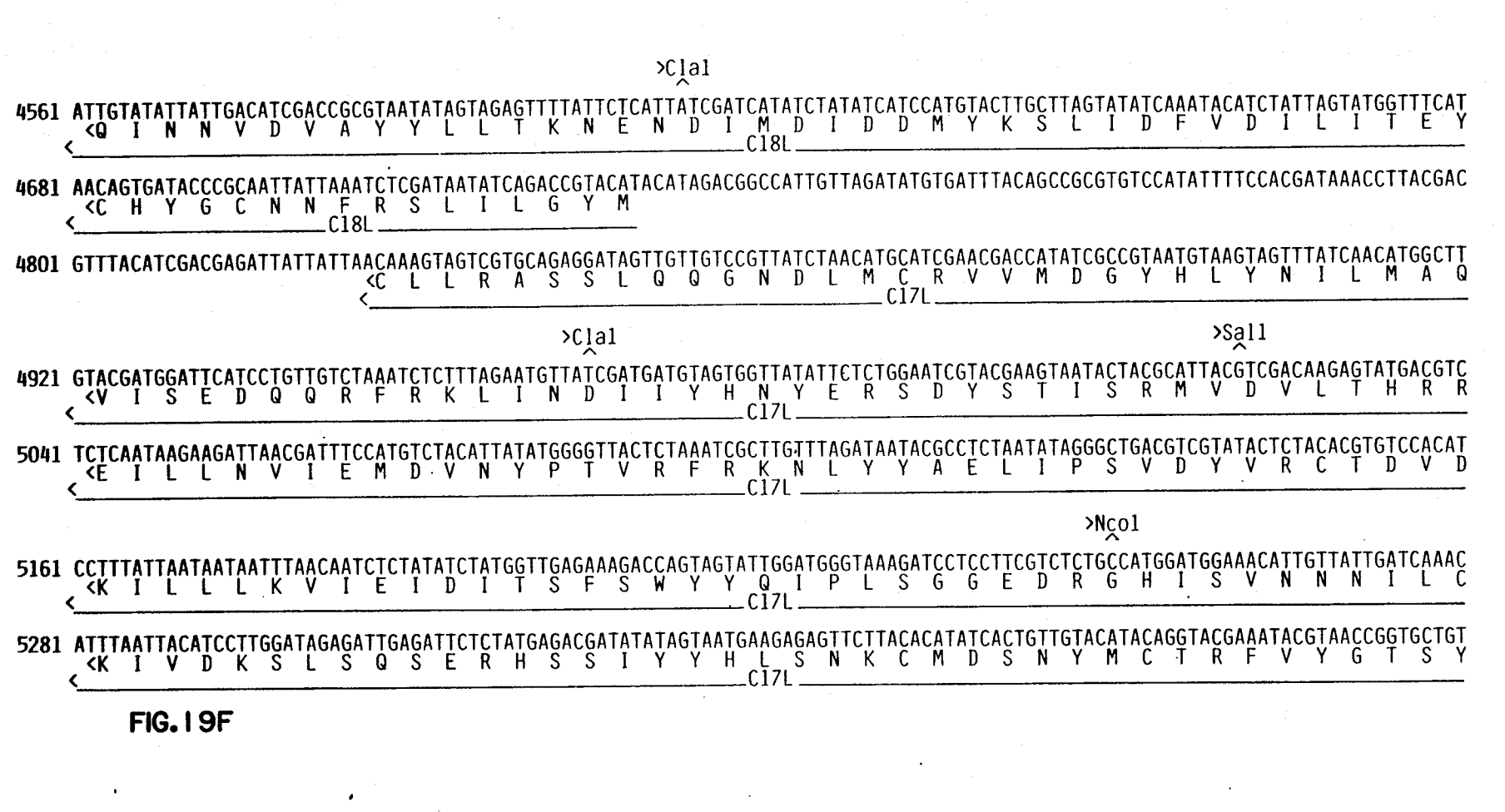
Figure 19G:
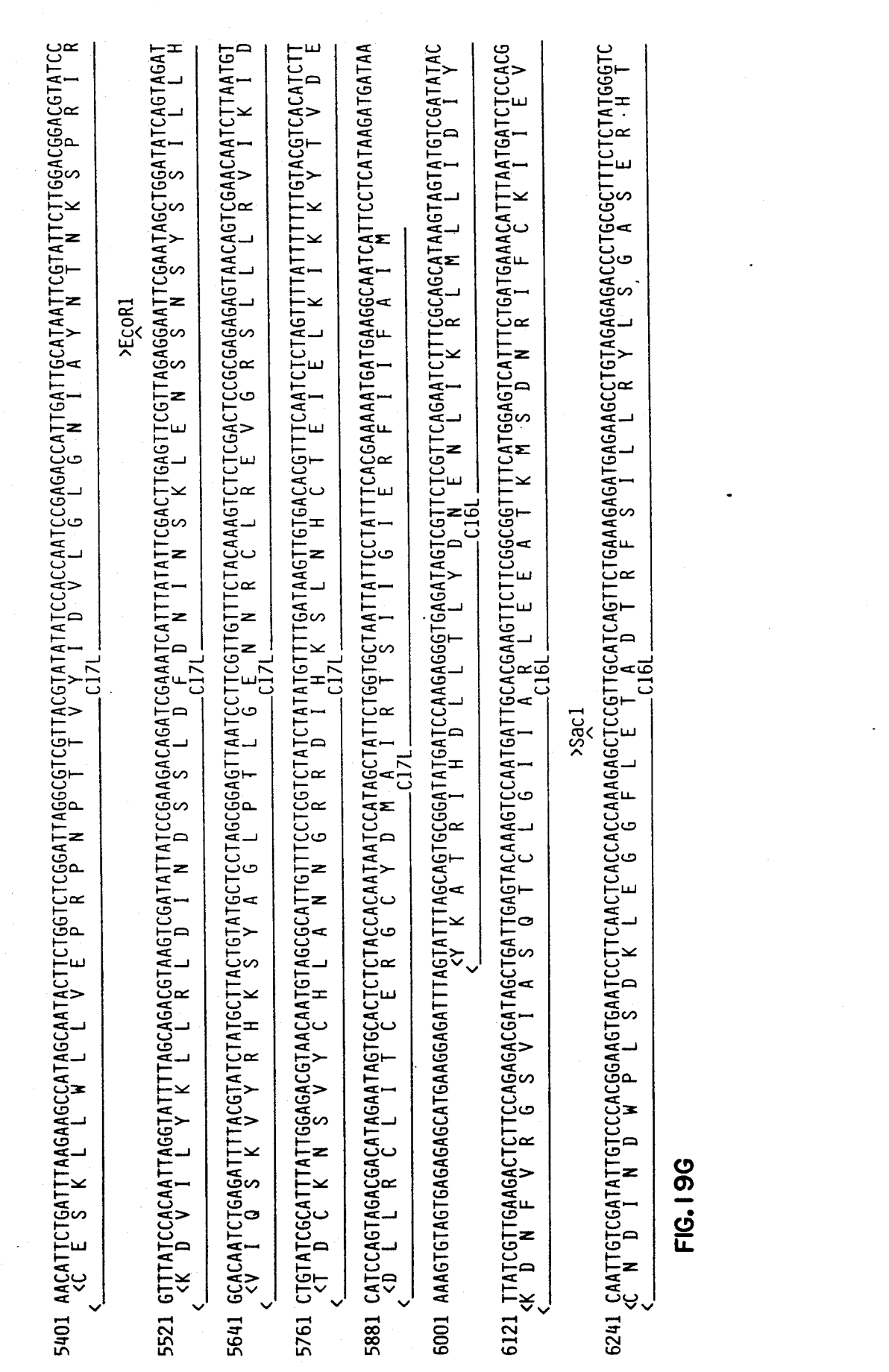
Figure 19H:
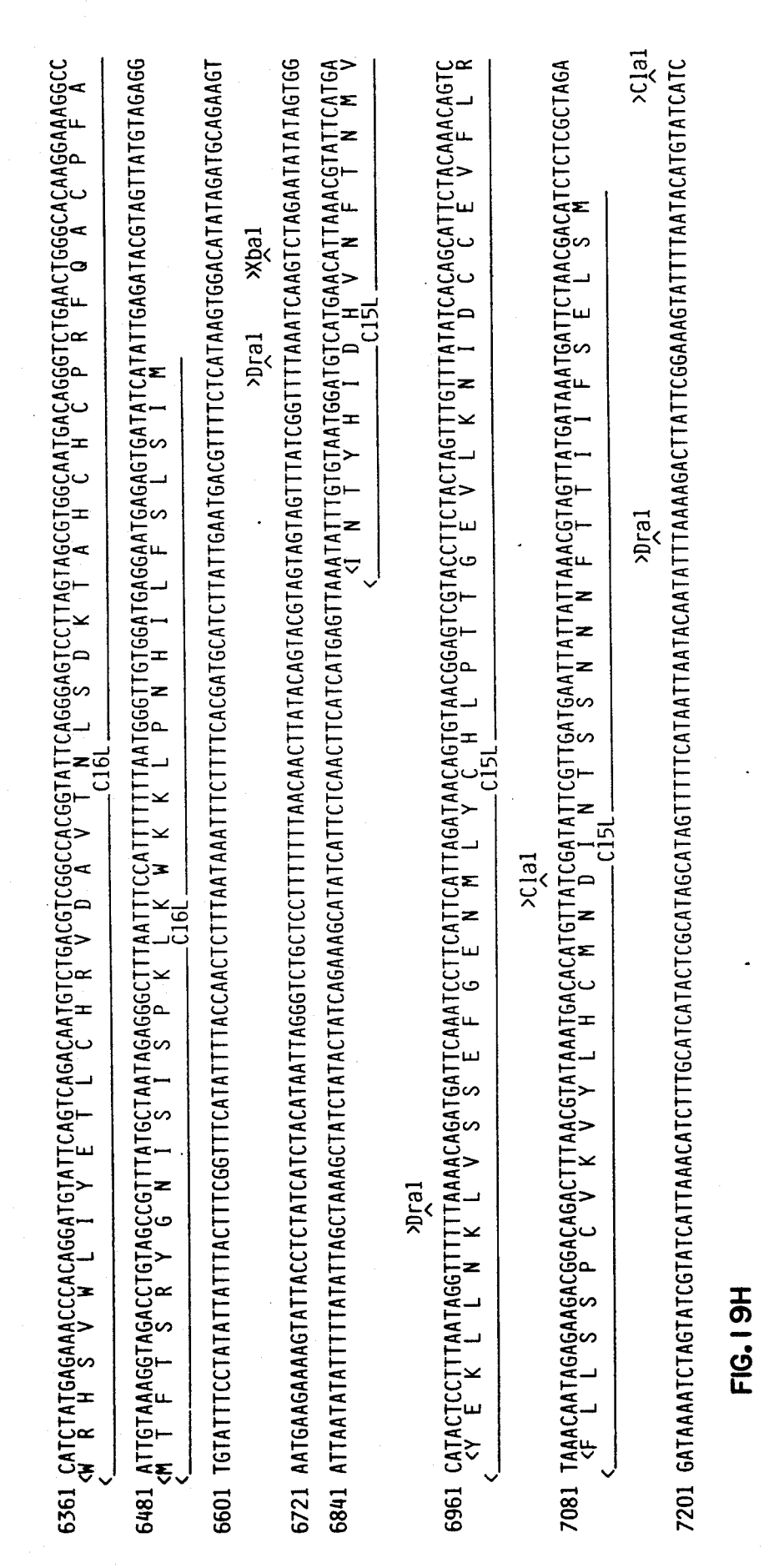
Figure 19I:
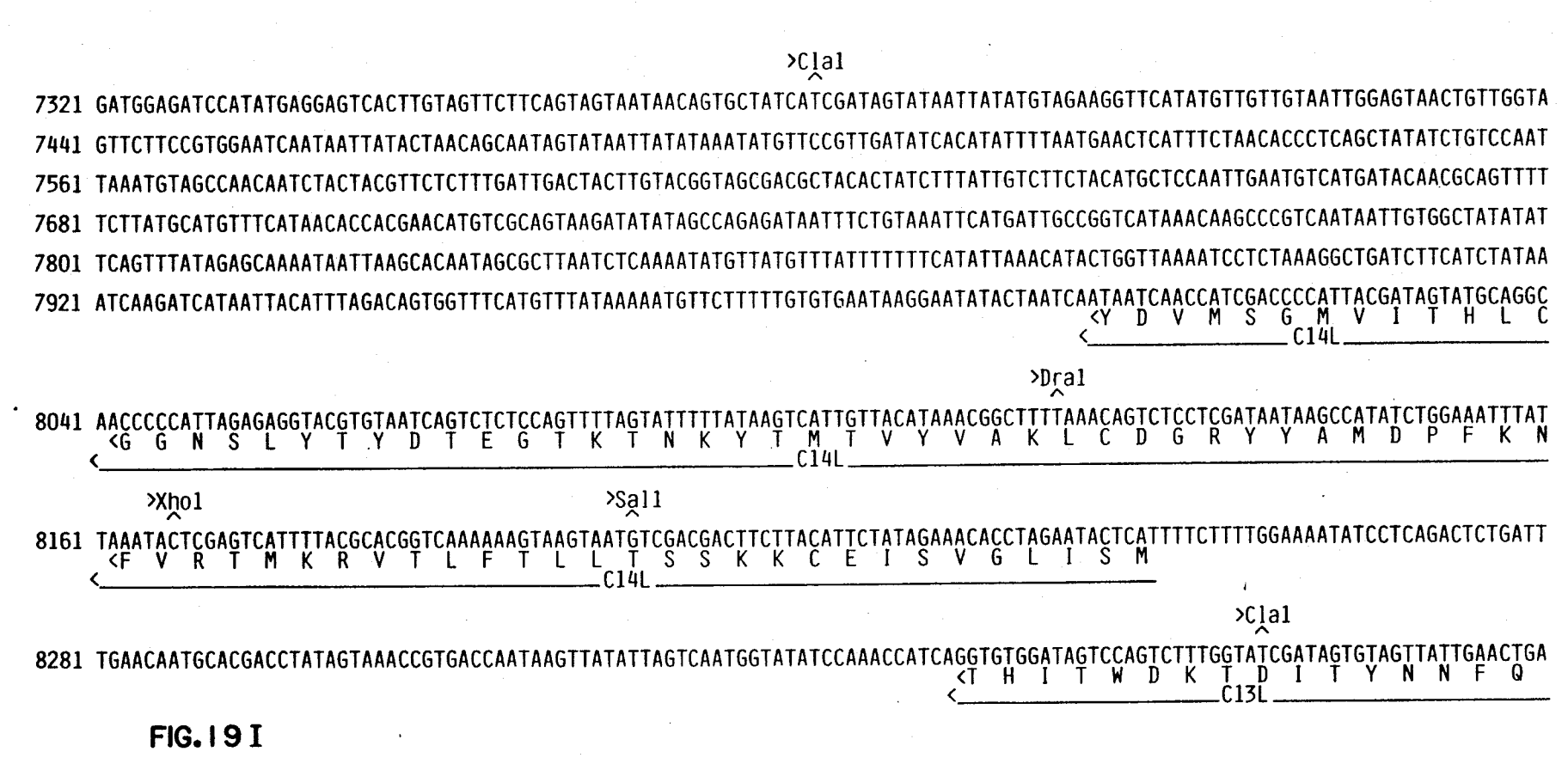
Figure 19J:
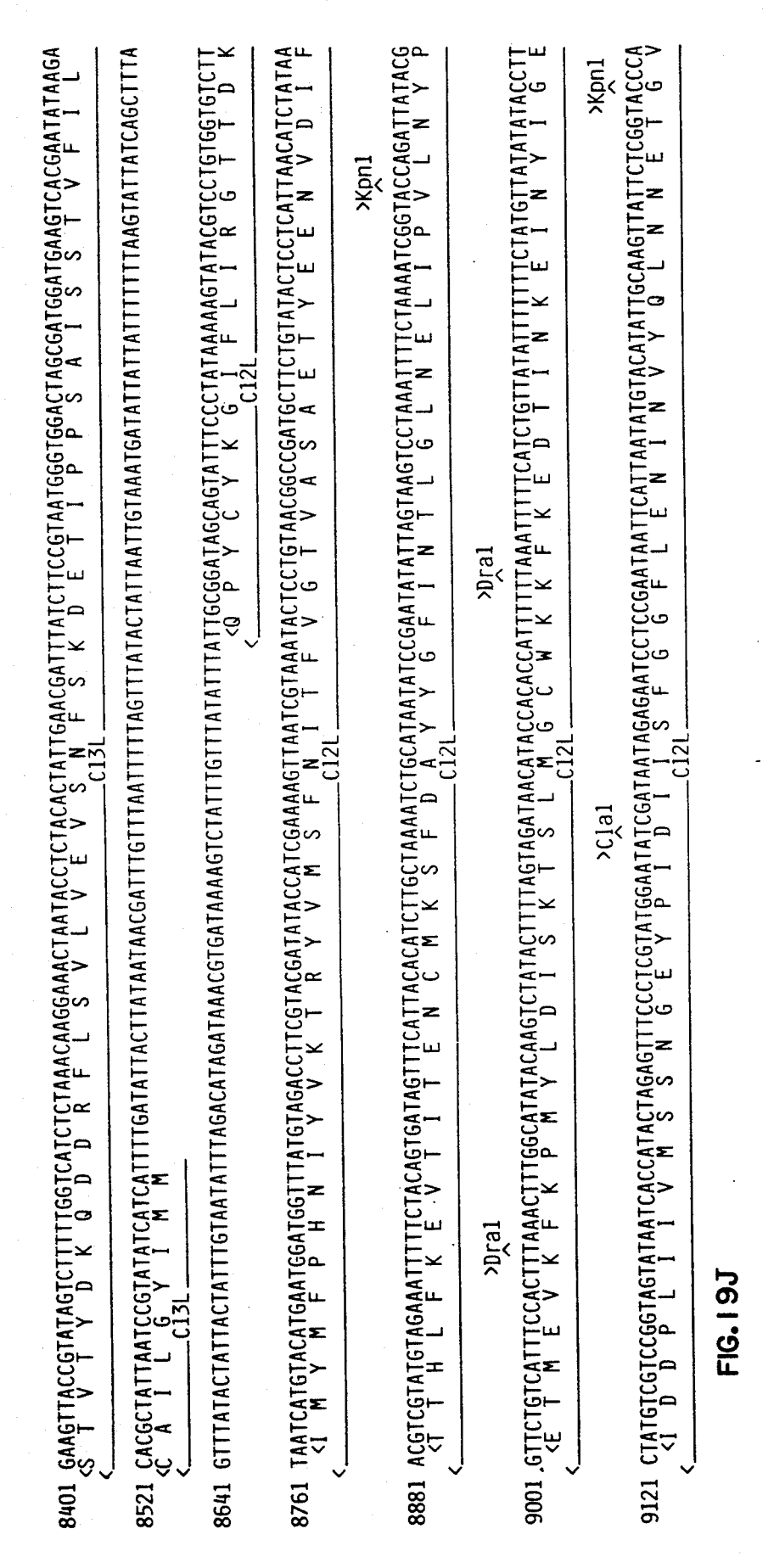
Figure 19K:
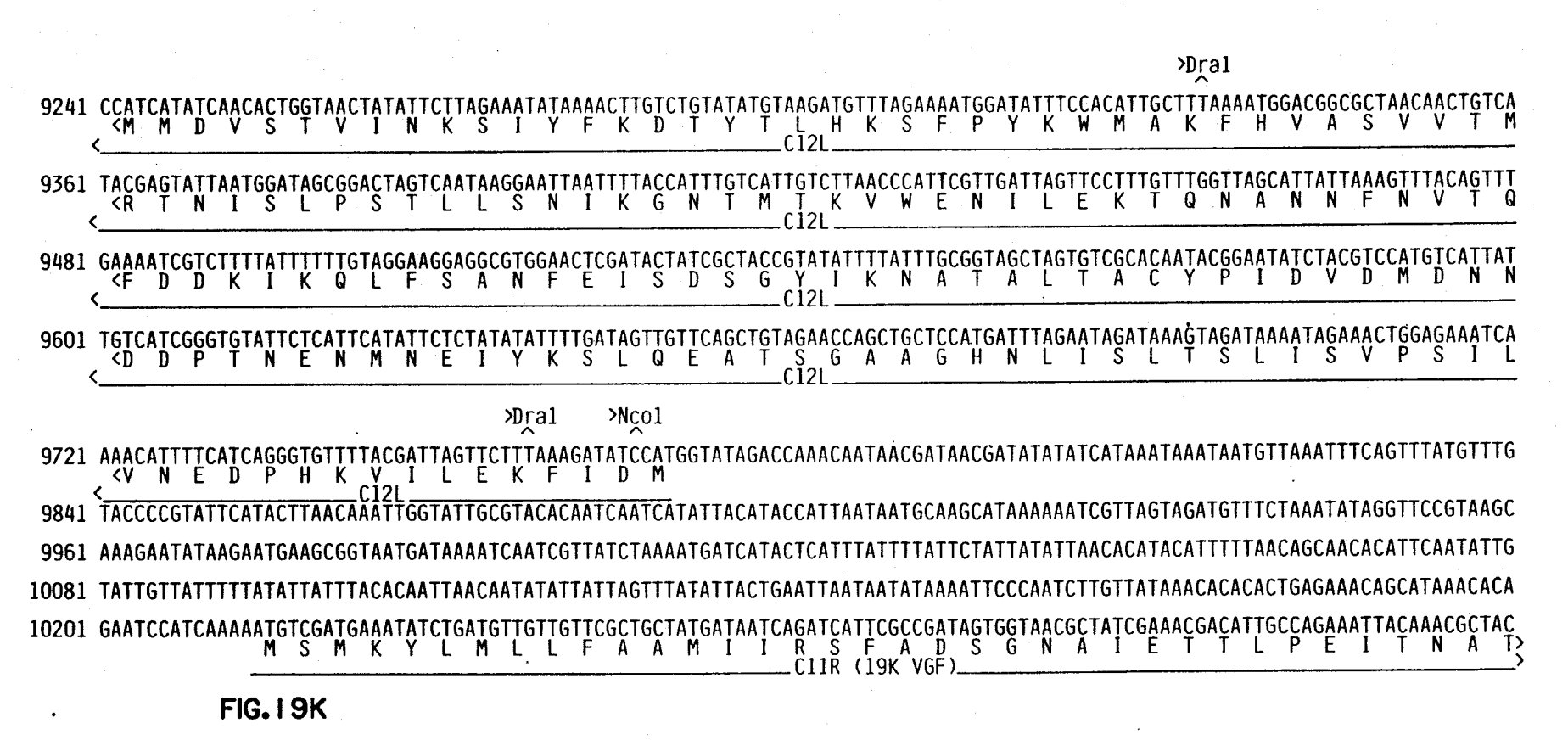
Figure 19N:
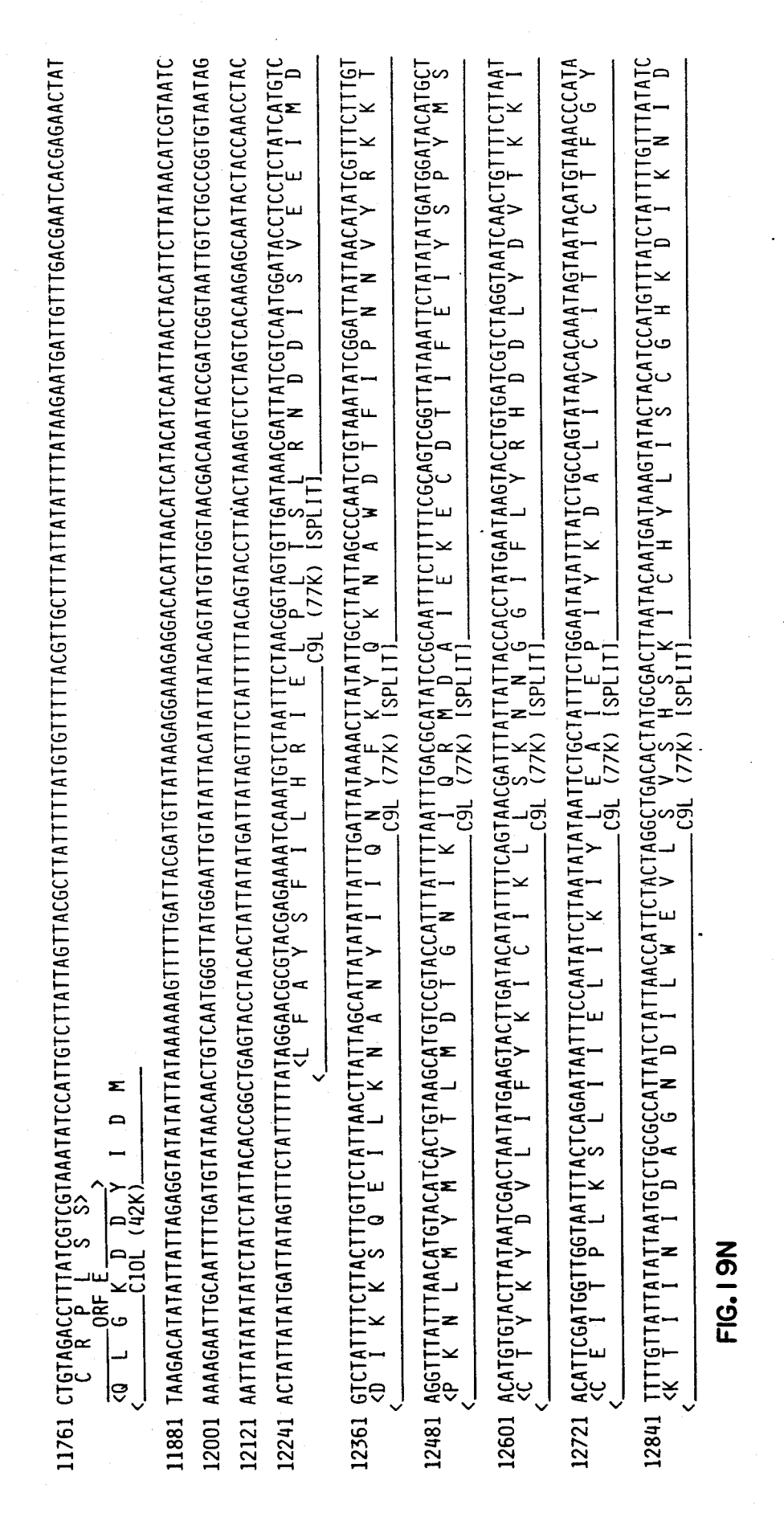
Figure 20B:
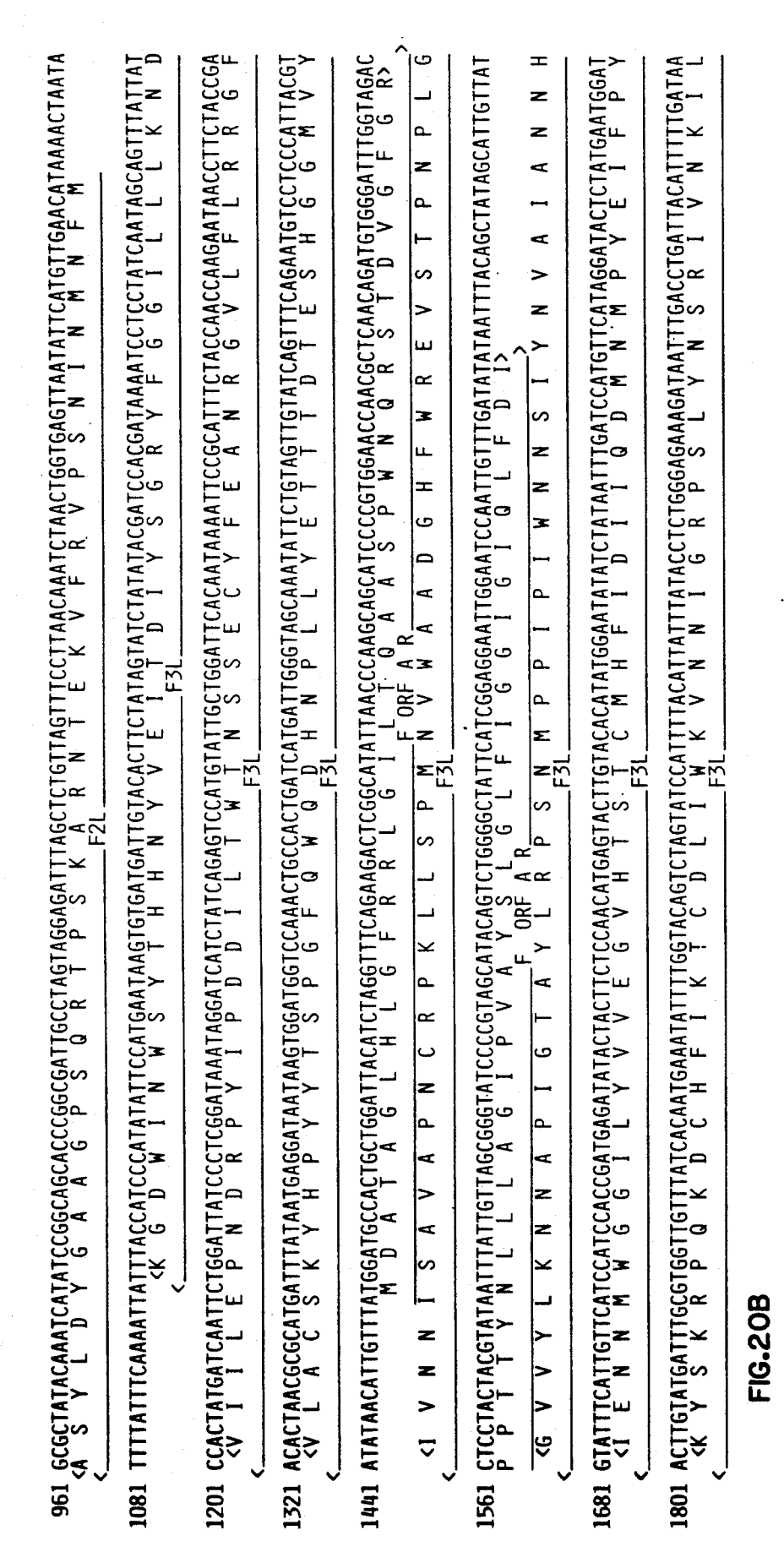
Figure 20C:
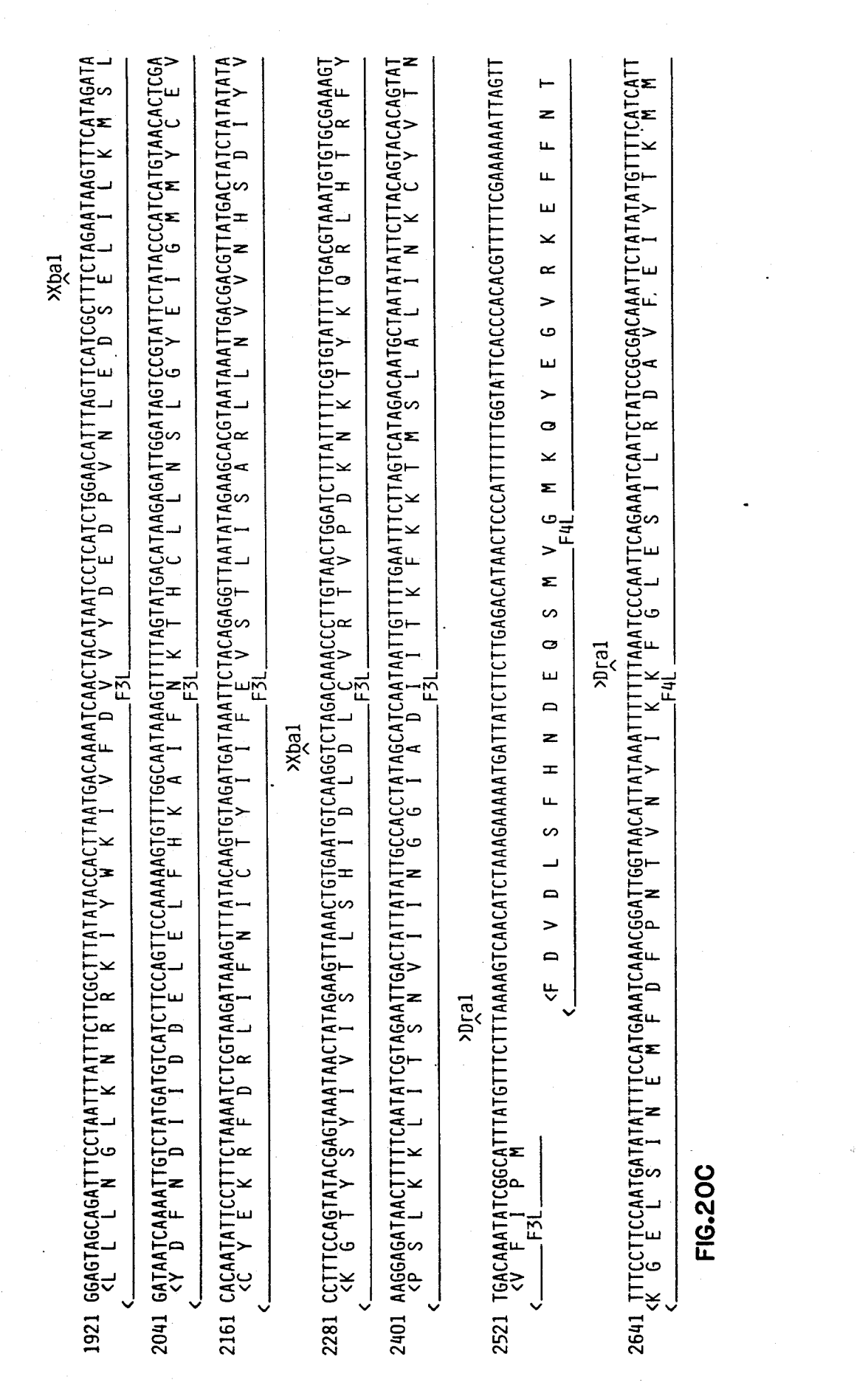
Figure 20D:
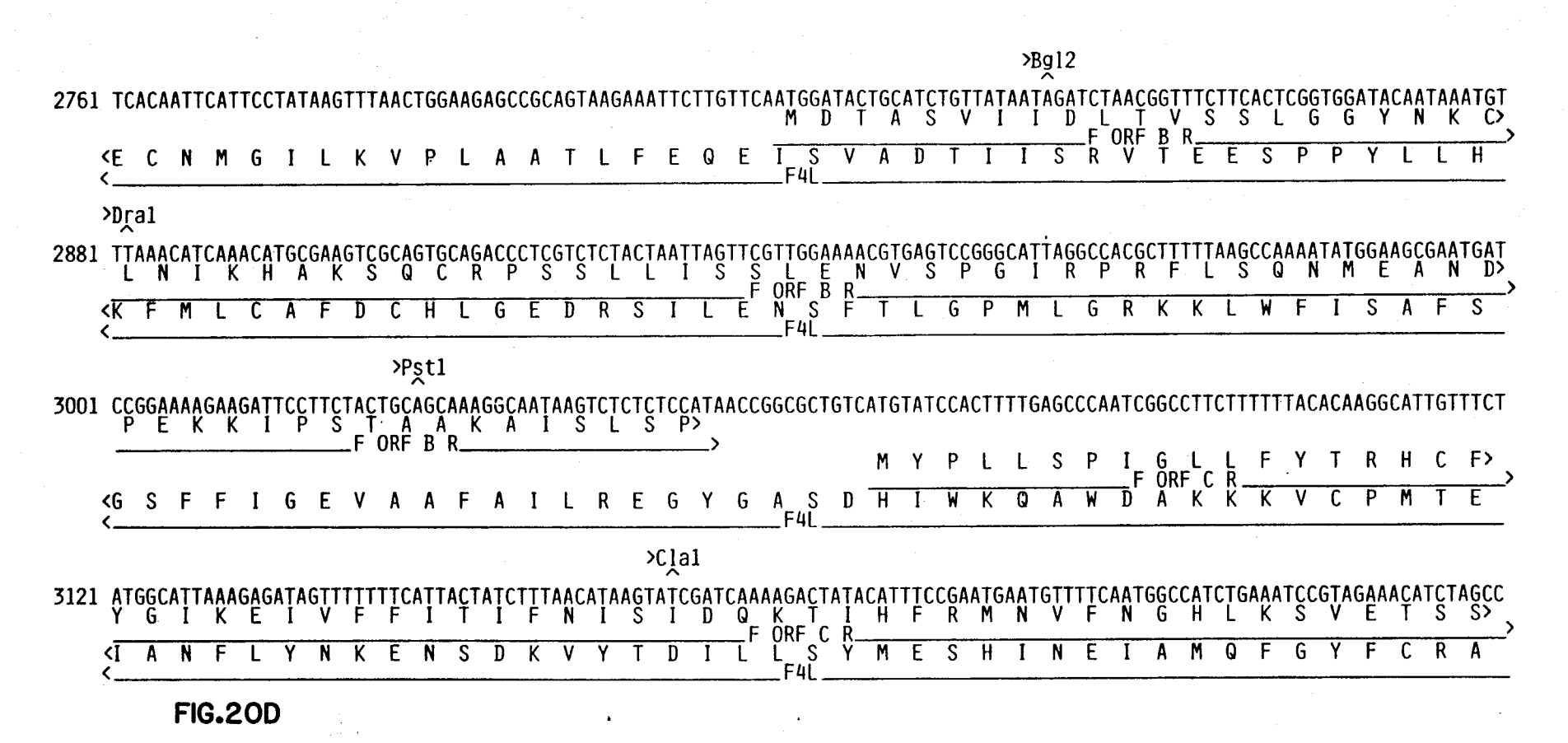
Figure 20E:
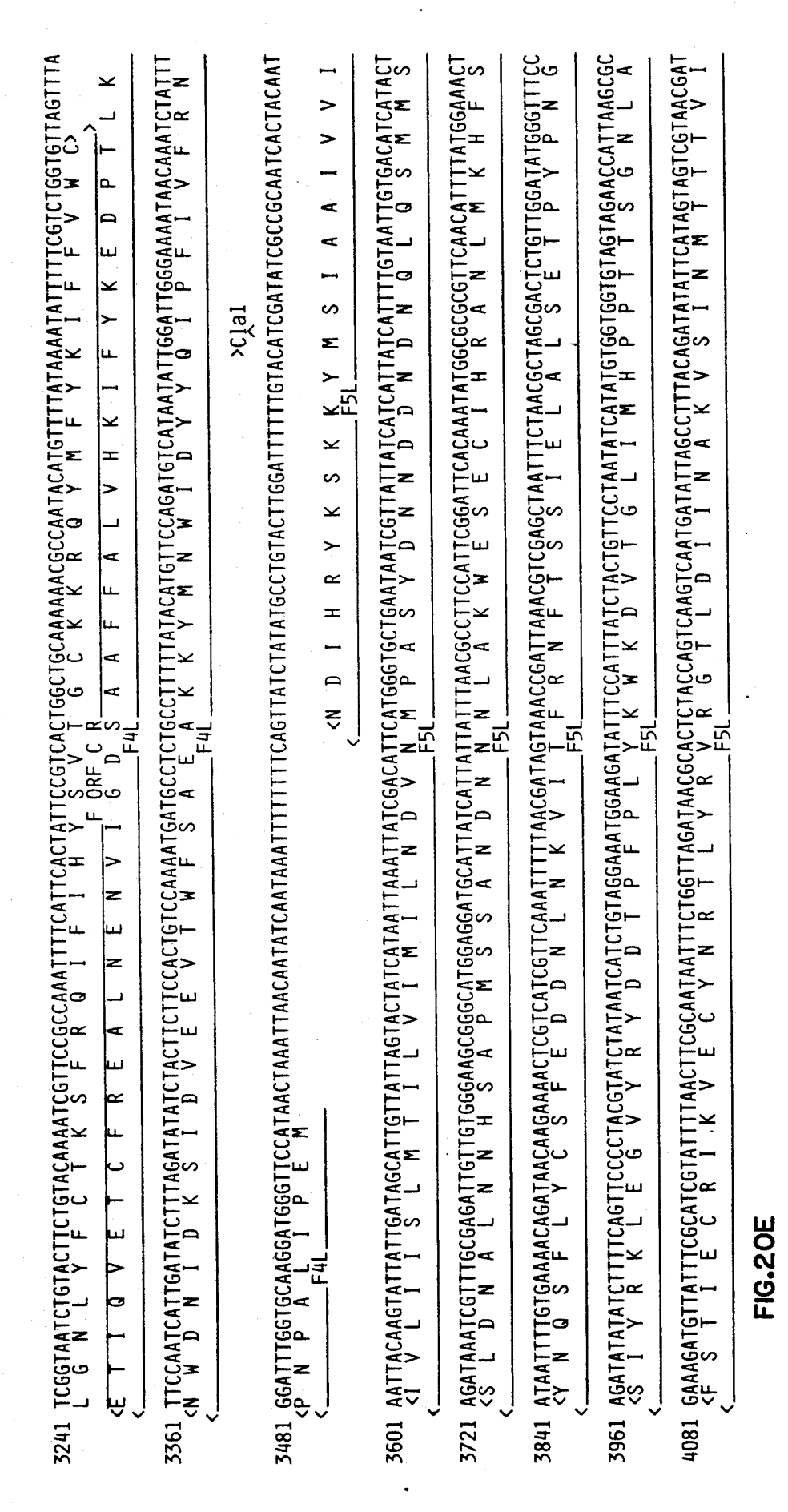

To delete all genes from the left end of vaccinia up to and including F4L, plasmid pMPLENDΔ (FIG. 18) was constructed as follows. A right flanking arm from HindIII F was obtained by digestion of pMPCTFRΔ with SmaI and BglII, followed by isolation of the 2.3 kb fragment. pMPVCEND (FIG. 18), which contains DNA tandem repeats from the terminus of vP452, was digested with HindIII followed by blunt ending with Klenow fragment E. coli polymerase and cutting with BglII. The two fragments were ligated together, generating pMPLENDΔ. In pMPLENDΔ the left vaccinia arm is composed of tandem repeat units and the right vaccinia arm is composed of DNA derived from HindIII F. In plasmid pMPLENDΔ, the leftmost 38 genes [C23L-F4L] of the Copenhagen genome are deleted, totalling 32,681 bp (from HindIII C: FIG. 19, position 340 through end (13,638 bp deleted); from HindIII C, M, N and K: all of FIG. 8 (15,537 bp) and from HindIII F: FIG. 20 positions 1-3506).

To delete genes from the right end of the genome, plasmid pMPRENDΔ was constructed to provide flanking vaccinia arms for the deletion of the vaccinia hemorrhagic (u) region (Example 5) and all genes to the right of this region. The sequence of HindIII B, the rightmost HindIII fragment in the genome was determined by sequencing various pUC-based clones of this region (FIG. 21). Comparison of the sequences derived from the left and right regions of the genome reveals that the terminal repetition extends to position 8104 of FIG. 19. Thus the inverted terminal repetition of the Copenhagen strain of vaccinia virus analyzed here is composed of 8.1 kb of coding region in addition to the blocks of tandem repeats. The leftmost 9 ORFs in HindIII C, ORFs C23L through C15L, correspond to the rightmost 9 ORFs in HindIII B, ORFs B29R through B21R. FIG. 21 contains the sequence for Copenhagen HindIII B beginning at the HindIII A/B junction and continuing rightward through the rightmost ORF which begins in unique DNA sequences (B20R). The right copy of the terminal repetition begins at position 17,132 of FIG. 21, 14 bp before the end of the B20R ORF.

pSD477VC is a pUC-based NcoI NruI subclone of Copenhagen vaccinia HindIII B (FIG. 21, positions 9713-11299) which contains the hemorrhagic (u) region (ORFs B13R and B14R). pSD478VC (FIG. 18) is a derivative of pSD477VC in which the entire u region (positions 10,024-11,014, FIG. 21, is replaced by a multiple cloning region including a BglII site. The pair of synthetic oligonucleotides which were annealed for this purpose were SD41mer (5' CGATTACTAGATCTGAGCTCCCCGGGCTCGAGGGATCCGTT 3') and SD39mer (5' AACGGATCCCTCGAGCCCGGGGAGCTCAGATCTAGTAAT 3'). To obtain a flanking vaccinia arm to the left of the u region, pSD478VC was cut with EcoRI at the junction of pUC/vaccinia sequences, blunt ended by Klenow fragment of E. coli polymerase, and cut with BglII. A 0.3 kb fragment containing the vaccinia u promoter region and flanking sequences to the left of the u region was isolated. This fragment was ligated with a vector fragment obtained by cutting pMPVCEND with HindIII, blunt ending with Klenow fragment of E. coli polymerase, and cutting with BglII. The resulting plasmid, pMPRENDΔ, contains a left vaccinia arm derived from HindIII B DNA upstream from the B13R ORF, and including the B13R (u) promoter region. The right vaccinia arm in pMPRENDΔ consists of blocks of tandem repeats, and is identical to the left vaccinia arm present in the left end deletion plasmid, pMPLENDΔ. The two arms of pMPRENDΔ flank a deletion of 17 ORFs [B13R-B29R]. The total size of the deletion between the flanking vaccinia arms in the right end deletion plasmid, pMPRENDΔ is 14,873 bp, all from HindIII B (sequence presented in FIG. 21 positions 10,024 through 17,145; continuing in the inverted terminal repetition, with deleted sequence equivalent to that presented in FIG. 19, positions 8090 through 340). The strategy for the construction of deletion plasmids pMPLENDΔ and pMPRENDΔ is presented schematically in FIG. 18. Filled blocs indicate Copenhagen vaccinia DNA consisting of the tandem repeats derived from the terminus of vP452; open blocs indicate other Copenhagen vaccinia DNA. The location of the deletions in plasmids pMPCTFRΔ, pSD478VC, pMPLENDΔ and pMPRENDΔ is indicated by triangles.

To take advantage of selective pressure in generating recombinant vaccinia virus deleted for large amounts of DNA at both ends of the genome, two selectable markers were used. The first is the vaccinia C7L human host range gene (Example 7) with selection of recombinant virus progeny on human MRC-5 cells. The second is the *E. coli* gene encoding the gene for guanine phosphoribosyl transferase (Ecogpt gene) with selection of recombinant vaccinia virus progeny using mycophenolic acid (2,8).

To create a moveable fragment containing only the vaccinia C7L gene and its promoter, pCOPCS-4 was cut with NcoI near the 3' end of the C7L gene (position 870, FIG. 8) and with BamHI 48 bp downstream from the C7L coding sequences. The end of the C7L gene was reconstructed using synthetic oligonucleotides, MPSYN258 (5' CATGGATTAATTAATTTTTTTG 3') and MPSYN259 (5' GATCCAAAAAAATTAATTAATC 3'), which were annealed and ligated with the vector fragment, producing plasmid pMP258/259. pMP258/259 was cut with BglII and BamHI, and a 660 bp fragment containing the C7L gene and its promoter was isolated for insertion into the left and right end deletion plasmids, pMPLENDΔ and pMPRENDΔ, respectively.

A 670 bp BglII/BamHI fragment containing the Ecogpt gene was derived from plasmid pSV2gpt (ATCC #37145) (71) by the addition of a BamHI linker at the AhaIII site downstream from coding sequences (72).

Plasmids pMPLENDΔ and pMPRENDΔ, containing vaccinia deletions near the left and right ends of the vaccinia genome, respectively, were cut with BglII. The BglII/BamHI fragments containing the C7L gene and the Ecogpt gene were inserted into the plasmid vectors, producing a total of four plasmids (Table 7). Note that the C7L gene is under the control of its own promoter in both pMPLΔC7 and pMPRΔC7. The Ecogpt gene is under the control of the F4L promoter in pMPLgpt and under the control of the B13R (u) promoter in pMPRgpt. Recombination was performed between these plasmids and rescuing virus as listed in Table 7. Recombinant vaccinia virus progeny from recombinations introducing the C7L gene were selected by plating on MRC-5 cells; progeny from recombinations introducing the Ecogpt gene were selected by growth in the presence of mycophenolic acid. Note that selection for growth on MRC-5 cells is advantageously carried out using a rescuing virus, such as vP668, which is deleted for both C7L and K1L.

TABLE 7

A. Construction of plasmids for deletions near Copenhagen termini

| Plasmid Substrate | Selectable Marker | Plasmid Product | Deletion |
|---|---|---|---|
| pMPLENDΔ | C7L | pMPLΔC7 | C23L-F4L |
| pMPLENDΔ | Exogpt | pMPLgpt | C23L-F4L |
| pMPRENDΔ | C7L | pMPRΔC7 | B13R-B29R |
| pMPRENDΔ | Ecogpt | pMPRgpt | B13R-B29R |

B. In vivo recombinations using deletion plasmids with Copenhagen vaccinia virus

| Rescuing Virus | Plasmid | Vaccinia Deletion Mutant |
|---|---|---|
| vP668 (TK⁻, [C7L-K1L]⁻) | pMPLΔC7 ([C23L-F4L]⁻, C7L⁺) | vP789 |
| vP668 (TK⁻, [C7L-K1L]⁻) | pMPRΔC7 ([B13R-B29R]⁻, C7L⁺) | vP774 |
| vP617 (TK⁻, ATI⁻, HA⁻) | pMPRgpt ([B13R-B29R]⁻, Exogpt⁺) | vP759 |
| vP617 (TK⁻, ATI⁻, HA⁻) | pMPLgpt ([C23L-F4L]⁻, Ecogpt⁺) | vP791 |
| vP723 (TK⁻, ATI⁻, HA⁻, u⁻) | pMPLgpt ([C23L-F4L]⁺, Ecogpt⁺) | vP796 |
| vP796 (TK⁻, ATI⁻, HA⁻, [C23L-F4L]⁻, Ecogpt⁺) | pMPRΔC7 ([B13R-B29R]⁻ + C7L) | vP811 |

Recombinant vaccinia virus deletion mutant, vP796, was generated by recombination between the left end deletion plasmid carrying the selectable Ecogpt marker, pMPLgpt, and rescuing virus vP723, which is additionally deleted for the TK and HA genes, as well as the ATI and u equivalent regions. By DNA restriction analysis, vP796 is deleted for the [C23L through F4L] region, as well as the TK, HA, ATI and u regions. Since the 38 gene deletion near the left end of vP796 encompasses both C7L and K1L, vP796 was used as rescuing virus for recombination with pMPRΔC7, the right end deletion plasmid containing C7L. The resulting vaccinia recombinant containing deletions near both termini, vP811, was selected by growth on MRC-5 cells.

REFERENCES

1. Beck, E., Ludwig, G., Auerswald, E. A., Reiss, B., and H. Schaller, Gene 19, 327–336 (1982).
2. Boyle, D. B. and B. E. H. Coupar, Gene 65, 123–128 (1988).
3. Chakrabarti, S., Brechling, K., and B. Moss, Mol. Cell. Biol. 5, 3403–3409 (1985).
4. Clewell, D. B., J. Bacteriol. 110, 667–676 (1972).
5. Clewell, D. B. and D. R. Helinski, Proc. Natl. Acad. Sci. U.S.A. 62, 1159–1166 (1969).
6. Drillien, R., Koehren, F., and A. Kirn, Virology 111, 488–499 (1981).
7. Drillien, R., Spehner, D., and A. Kirn, J. Virol. 28, 843–850 (1978).
8. Falkner, F. G. and B. Moss, J. Virol. 62, 1849–1854 (1988).
9. Fathi, Z., Sridhar, P., Pacha, R. F., and R. C. Condit, Virology 155, 97–105 (1986).
10. Fenner, F. and J. F. Sambrook, Virology 28, 600–609 (1966).
11. Franke, C. A., Rice, C. M., Strauss, J. H., and D. E. Hruby, Mol. Cell. Biol. 5, 1918–1924 (1985).
12. Gangemi, J. D. and D. G. Sharp, Virology 85, 262–270 (1978).
13. Gemmell, A. and F. Fenner, Virology 11, 219–235 (1960).
14. Gillard, S., Spehner, D., and R. Drillien, J. Virol. 53, 316–318 (1985).
15. Gillard, S., Spehner, D., Drillien, R., and A. Kirn, Proc. Natl. Acad. Sci. U.S.A. 83, 5573–5577 (1986).
16. Graham, F. L. and A. J. Van der Eb, Virology 54, 536–539 (1973).
17. Hruby, D. E., Lynn, D. L., Condit, R., and J. R. Kates, J. gen Virol. 47, 485–488 (1980).
18. Kieny, M. P., Lathe, R., Drillien, R., Spehner, D., Skory, S., Schmitt, D., Wictor, T., Koprowski, H., and J. P. Lecocq, Nature (London) 312 163–166 (1984).
19. Lake, J. R. and P. D. Cooper, J. gen Virol. 48, 135–147 (1980).
20. Mackett, M., Smith, G. L. and B. Moss, Proc. Natl. Acad. Sci. U.S.A. 79, 7415–7419 (1982).

21. Mackett, M. and J. R. Arrand, EMBO 4, 3229-3235 (1985).
22. Maniatis, T., Fritsch, E. F., and J. Sambrook, Molecular Cloning: A Laboratory Manual, (Cold Spring Harbor Laboratory, New York) (1982).
23. Mayr, A., Hochstein-Mintzel, V., and H. Stickl, Infection 3, 6-14 (1975).
24. McClain, M. E., Aust. J. exp. Biol. med. Sci. 43, 31-44 (1965).
25. Moyer, R. W. and C. T. Rothe, Virology 102, 119-132 (1980).
26. Nakano, E., Panicali, D., and E. Paoletti, Proc. Natl. Acad. Sci. U.S.A. 79, 1593-1596 (1982).
27. Panicali, D., Davis, S. W., Mercer, S. R., and E. Paoletti, J. Virol. 37, 1000-1010 (1981).
28. Panicali, D. and E. Paoletti, Proc. Natl. Acad. Sci. U.S.A. 79, 4927-4931 (1982).
29. Panicali, D., Grzelecki, A., and C. Huang, Gene 47, 193-199 (1986).
30. Perkus, M. E., Panicali, D., Mercer, S., and E. Paoletti, Virol. 152, 285-297 (1986).
31. Perkus, M. E., Piccini, A., Lipinskas, B. R., and E. Paoletti, Science 229, 981-984 (1985).
32. Piccini, A., Perkus, M. E., and E. Paoletti, In: Methods in Enzymology, Vol. 153, ed. Wu, R. and L. Grossman (Academic Press), pp. 545-563 (1987).
33. Rosel, J. L., Earl, P. L., Weir, J. P., and B. Moss, J. Virol. 60 436-449 (1986).
34. Shapira, S. K., Chou, J., Richaud, F. V., and M. J. Casadaban, Gene 25, 71-82 (1983).
35. Southern, P. H. and P. Berg, J. Mol. Appl. Genet. 1, 327-341 (1982).
36. Tagaya, I., Kitamura, T., and Y. Sano, Nature (London) 192, 381-382 (1961).
37. Wachsman, M., Aurelian, L., Smith, C. C., Lipinskas, B. R., Perkus, M. E., and E. Paoletti, J. Inf. Dis. 155, 1188-1197 (1987).
38. Wilson, E. M., Hodges, W. M., and D. E. Hruby, Gene 49, 207-213 (1986).
39. Yuen, L. and B. Moss, Proc. Natl. Acad. Sci. U.S.A. 84, 6417-6421 (1987).
40. Kotwal, G. J. and B. Moss, Virology 167, 524-537 (1988).
41. Taylor, J., Weinberg, R., Kawaoda, Y., Webster, R. G., and E. Paoletti, Vaccine 6, 504-508 (1988).
42. Taylor, J., Weinberg, R., Languet, B., Desmettre, P., and E. Paoletti, Vaccine 6, 497-503 (1988).
43. Pickup, D. J., Ink, B. S., Hu, W., Ray, C. A., and W. K. Joklik, Proc. Natl. Acad. Sci. U.S.A. 83, 7698-7702 (1986).
44. Southern, E. M., J. Mol. Biol. 98, 503-517 (1975).
45. Kotwal, G. J. and B. Moss, J. Virol. 63, 600-606 (1989).
46. Tabor, S. and C. C. Richardson, Proc. Natl. Acad. Sci. U.S.A. 84, 4767-4771 (1987).
47. Patel, D. D. and D. J. Pickup, EMBO 6, 3787-3794 (1987).
48. Patel, D. D., Ray, C. A., Drucker, R. P., and D. J. Pickup, Proc. Natl. Acad. Sci. U.S.A. 85, 9431-9435 (1988).
49. Bertholet, C., Drillien, R., and R. Wittek, Proc. Natl. Acad. Sci. U.S.A. 82, 2096-2100 (1985).
50. Guo, P., Goebel, S., Davis, S., Perkus, M. E., Languet, B., Desmettre, P., Allen, G., and E. Paoletti, J. Virol. 63, 4189-4198 (1989).
51. Tamin, A., Villarreal, E. C., Weinrich, S. L., and D. E. Hruby, Virology 165, 141-150 (1988).
52. Boursnell, M. E. G., Foulds, I. J., Campbell, J. I., and M. M. Binns, J gen Virol. 69, 2995-3003 (1988).
53. Mandecki, W., Proc. Natl. Acad. Sci. U.S.A. 83, 7177-7181 (1986).
54. Spehner, D., Gillard, S., Drillien, R., and A. Kirn, J. Virol. 62, 1297-1304 (1988).
55. Altenburger, W., Suter, C.-P., and J. Altenburger, Arch. Virol. 105, 15-27 (1989).
56. Hruby, D. E., Maki, R. A., Miller, D. B., and L. A. Ball, Proc. Natl. Acad. Sci. U.S.A. 80, 3411-3415 (1983).
57. Robbins, A. K., Dorney, D. J., Wathen, M. W., Whealy, M. E., Gold, C., Watson, R. J., Holland, L. E., Weed, S. D., Levine, M., Glorioso, J. C., and L. W. Enquist, J. Virol. 61, 2691-2701 (1987).
58. Robbins, A. K., Watson, R. J., Whealy, M. E., Hays, W. W., and L. W. Enquist, J. Virol. 58, 339-347 (1986).
59. Wathen, M. W. and L. M. K. Wathen, J. Virol. 51, 57-62 (1984).
60. Mettenleiter, T. C., Lukacs, N., Thiel, H. -J., Schreurs, C., and H. J. Rziha, Virology 152, 66-75 (1986).
61. Petrovskis, E. A., Timmins, J. G., Armentrout, M. A., Marchioli, C. C., Yancey, Jr., R. J., and L. E. Post, J. Virol. 59, 216-223 (1986).
62. Schmitt, J. F. C. and H. G. Stunnenberg, J. Virol. 62, 1889-1897 (1988).
63. Vos, J. C. and H. G. Stunnenberg, EMBO 7, 3487-3492 (1988).
64. Bucher, D., Popple, S., Baer, M., Mikhail, A., Gong, Y. -F., Whitaker, C., Paoletti, E., and A. Judd, J. Virol. 63, 3622-3633 (1989).
65. Saiki, R. K., Gelfand, D. H., Stoffel, S., Scharf, S. J., Higuchi, R., Horn, G. T., Mullis, K. B., and H. A. Erlich, Science 239, 487-491 (1988).
66. Kaplan, J. M., Mardon, G., Bishop, J. M., and H. E. Varmus, Mol. Cell. Biol. 8, 2435-2441 (1988).
67. Baroudy, B. M., Venkatesan, S., and B. Moss, Cell 28, 315-324 (1982).
68. Wittek, R. and B. Moss, Cell 21, 277-284 (1980).
69. Wittek, R., Muller, H. K., Menna, A., and R. Wyler, FEBS Letters 90, 41-46 (1978).
70. Slabaugh, M., Roseman, N., Davis, R., and C. Mathews, J. Virol. 62, 519-527 (1988).
71. Mulligan, R. C. and P. Berg., Science 209, 1422-1427 (1980).
72. Pratt, D. and S. Subramani, Nuc. Acids Res. 11, 8817-8823 (1983).

What is claimed is:

1. A method of expressing a gene product in a cell cultured in vitro, which method comprises introducing into the cell a modified recombinant vaccinia virus, said modified recombinant vaccinia virus having host range genes deleted therefrom so that the virus has restricted replication in the cell and said modified recombinant virus comprising DNA which codes for and expresses the gene product in the cell with restricted replication of the virus in the cell.

2. A modified recombinant vaccinia virus for expressing a gene product in a host, said modified recombinant vaccinia virus having host range genes deleted therefrom so that the virus has restricted replication in the host and said modified recombinant vaccinia virus comprising DNA which codes for and expresses the gene product in the host with restricted replication of the virus in the host.

3. A virus as claimed in claim 2, wherein the gene product is an antigen.

4. A virus as claimed in claim 3, wherein the host is a vertebrate and the antigen induces an immunological response in the vertebrate.

5. A virus as claimed in claim 4, wherein the antigen is selected from the group consisting of rabies glycoprotein antigen and pseudorabies glycoprotein antigen.

6. A virus as claimed in claim 2, wherein the host is a cell cultured in vitro.

* * * * *